United States Patent [19]

Keana et al.

[11] Patent Number: 5,708,168

[45] Date of Patent: Jan. 13, 1998

[54] AZEPINE COMPOUNDS

[75] Inventors: John F. W. Keana; Anthony P. Guzikowski, both of Eugene, Oreg.; Daniel F. Nogales, Nampa, Id.; Sui Xiong Cai, Irvine, Calif.

[73] Assignees: State of Oregon, Acting by and through The Oregon State Board of Higher Education, Acting for and on behalf of The Oregon Health Sciences University and The University of Oregon, Eugene Oregon, Eugene, Oreg.; ACEA Pharmaceuticals, Inc., Irvine, Calif.

[21] Appl. No.: 544,107

[22] Filed: Oct. 17, 1995

Related U.S. Application Data

[62] Division of Ser. No. 341,154, Nov. 16, 1994, Pat. No. 5,476,933.

[51] Int. Cl.$^6$ .................... C07D 223/16; C07D 223/32; A61K 31/55

[52] U.S. Cl. .................... 540/520; 540/521; 540/522; 540/523; 514/220; 514/221

[58] Field of Search .................... 540/520, 521, 540/522, 523

[56] References Cited

U.S. PATENT DOCUMENTS

| | | | |
|---|---|---|---|
| 5,254,683 | 10/1993 | Chapdelaine et al. | 540/523 |
| 5,446,039 | 8/1995 | Chapdelaine et al. | 514/213 |
| 5,492,905 | 2/1996 | Harris et al. | 514/213 |

FOREIGN PATENT DOCUMENTS

| | | | |
|---|---|---|---|
| 1 340 334 | 12/1973 | United Kingdom | 540/523 |
| WO 92/11854 | 7/1992 | WIPO . | |
| WO 92/22297 | 12/1992 | WIPO . | |
| WO 93/25534 | 12/1993 | WIPO . | |
| WO 94/07500 | 4/1994 | WIPO . | |
| WO 94/29275 | 12/1994 | WIPO . | |

OTHER PUBLICATIONS

Alberola et al., "Derivados de Ciclopentanohidrofenantreno. La reducción del cis,sin-1,4,4a,4b,5,6,7,8,10,10a-dodecahidro-2-metoxi-1,4-dioxofenantreno," *Anales de Física y Química* 62:691–698 (1966).

Birchall, G.R., and Rees, A.H., "Some Derivatives of 1–Benzazepine. Part II," *Can. J. Chem.* 52:610–615 (1974).

Bohlmann, et al., "Über die Regioselektivität von Diensynthesen substituierter Chinone," *Chem. Ber.* 110:2028–2045 (1977).

Boisvert, L., and Brassard, P., "Regiospecific Additions of Some Simple Dienes to Haloquinones," *Tetrahedron Letts.* 24(24):2453–2456 (1983).

Donaldson, et al., "Model Studies Toward the Synthesis of Leukotrienes: Hetero–Diels–Alder Reactivity of Tricarbonyl(diene)iron Complexes," *J. Org. Chem.* 56(14):4563–4566 (1991).

Giles, R.G.F., and Roos, G.H.P., "Regiospecific Addition of Methoxycyclohexa-1,3-Dienes to 2-Methoxy-1,4-Benzoquinone. Application to the Synthesis of 3-Methoxy-7-Methyljuglone and α-Caryopterone," *Tetrahedron Letts.* 47:4159–4160 (1975).

Giles, R.G.F., and Roos, G.H.P., "Syntheses of the Naturally Occurring Naphtho[2,3–b]pyran-5,10-quinones α-Caryopterone, Dihydro-α-caryopterone, and O-Methyldihydro-α-caryopterone," *J. Chem. Soc. Perkin Trans.* 1:1632–1635 (1976).

Giles, R.G.F., and Roos, G.H.P., "Syntheses of Substituted 1,4-Naphthoquinones by Diels-Alder Addition of Methoxycyclohexadienes to Substituted 1,4-Benzoquinones," *J. Chem. Soc. Perkin Trans.* 1:2057–2060 (1976).

Horn, et al., "Orthogonal Connection of Acenes via Two-Fold Diels-Alder Reactions," *Tetrahedron Letts.* 34(37):5889–5892 (1993).

Hughes, et al., "Azatropolones. Part II. The Schmidt Reaction of 2–Methoxy–5–methylbenzoquinone," *Can. J. Chem.* 52:3327–3330 (1974).

Kamabuchi, et al., "Synthesis and Cycloaddition of 2–(Dialkoxyboryl)–1,3–butadiene," *Tetrahedron Letts.* 34(30):4827–4828 (1993).

Mikami et al., "Chiral Titanium Complex-Catalyzed Diels-Alder Reaction: A Practical Route to Anthracycline Intermediates," *Tetrahedron: Asymmetry* 2(7):643–646 (1991).

Okamoto, et al., "Lewis Acid Catalyzed [2σ+2σ] Cycloreversion Reaction of Strained Cage Ketones to Triquinane Skeletons: Kinetic Evidence for a Large Acceleration of the Reaction Owing to Stereoelectronic Requirement," *Chem. Pharm. Bull.* 32(11):4593–4599 (1984).

Reich, et al., "Synthesis of 2,3–Disubstituted 1,3–Butadienes from Organotin Precursors and Butadienyllithium Reagents. Diels–Alder Reactivity," *J. Am. Chem. Soc.* 115(15):6625–6635 (1993).

Sha, C.–K., and Yang, J.–F., "Total Syntheses of Ellipticine Alkaloids and Their Amino Analogues," *Tetrahedron* 48(48):10645–10654 (1992).

(List continued on next page.)

*Primary Examiner*—Robert T. Bond
*Attorney, Agent, or Firm*—Sterne, Kessler, Goldstein & Fox P.L.L.C.

[57] ABSTRACT

Disclosed are methods of preparing azepines by a multistep synthesis including a Diels-Alder reaction. Also disclosed are methods of treating or preventing neuronal loss associated with stroke, ischemia, CNS trauma, hypoglycemia and surgery, as well as treating neurodegenerative diseases including Alzheimer's disease, amyotrophic lateral sclerosis, Huntington's disease and Down's syndrome, treating or preventing the adverse consequences of the hyperactivity of the excitatory amino acids, as well as treating anxiety, chronic pain, convulsions, inducing anesthesia and treating or preventing opiate tolerance are disclosed by administering to an animal in need of such treatment an azepine which has high binding to the NMDA glycine site.

13 Claims, No Drawings

OTHER PUBLICATIONS

Swartz, et al., "Competitive Antagonism of Glutamate Receptor Channels by Substituted Benzazepines in Cultured Cortical Neurons," *Molec. Pharmacol.* 41:1130–1141 (1992).

James, R.A., et al., "Some Derivatives of Benz[f]azepine. Part III," *J. Heterocyclic Chem.* 26:793–795 (May–Jun. 1989).

A copy of the International Search Report for the corresponding PCT Application, International Application No. PCT/US95/14572.

AZEPINE COMPOUNDS

This application is a division of application Ser. No. 08/341,154, filed Nov. 16, 1994, now U.S. Pat. No. 5,476,933.

The present invention was made with U.S. government support under NIDA grant No. DAO 6726 awarded by the National Institutes of Health. Therefore, the U.S. Government has certain rights in the invention.

FIELD OF THE INVENTION

The present invention is in the field of medicinal chemistry. In particular, the present invention relates to a process for the production of azepine compounds and the use of certain novel azepine compounds to treat or prevent neuronal degeneration associated with ischemia, pathophysiologic conditions associated with neuronal degeneration, convulsions, anxiety, chronic pain and to induce anesthesia.

BACKGROUND OF THE INVENTION

Glutamate is thought to be the major excitatory neurotransmitter in the brain. There are three major subtypes of glutamate receptors in the CNS. These are commonly referred to as kainate, AMPA and N-methyl-D-aspartate (NMDA) receptors (Watkins and Olverman, *Trends in Neurosci.* 7:265–272 (1987)). NMDA receptors are found in the membranes of virtually every neuron in the brain. NMDA receptors are ligand-gated cation channels that allow $Na^+$, $K^+$ and $Ca^{++}$ to permeate when they are activated by glutamate or aspartate (non-selective, endogenous agonists) or by NMDA (a selective, synthetic agonist) (Wong and Kemp, *Ann. Rev. Pharmacol. Toxicol.* 31:401–425 (1991)).

Glutamate alone cannot activate the NMDA receptor. In order to become activated by glutamate, the NMDA receptor channel must first bind glycine at a specific, high affinity glycine binding site which is separate from the glutamate/NMDA binding site on the receptor protein (Johnson and Ascher, *Nature* 325:329–331 (1987)). Glycine is therefore an obligatory co-agonist at the NMDA receptor/channel complex (Kemp, J. A., et al., *Proc. Natl. Acad. Sci. USA* 85:6547–6550 (1988)).

Besides the binding sites for glutamate/NMDA and glycine, the NMDA receptor carries a number of other functionally important binding sites. These include binding sites for $Mg^{++}$, $Zn^{++}$, polyamines, arachidonic acid and phencyclidine (PCP) (Reynolds and Miller, *Adv. in Pharmacol.* 21:101–126 (1990); Miller, B., et al., *Nature* 355:722–725 (1992)). The PCP binding site—now commonly referred to as the PCP receptor—is located inside the pore of the ionophore of the NMDA receptor/channel complex (Wong, E. H. F., et al., *Proc. Natl. Acad. Sci. USA* 83:7104–7108 (1986); Huettner and Bean, *Proc. Natl. Acad. Sci. USA* 85:1307–1311 (1988); MacDonald, J. F., et al., *Neurophysiol.* 58:251–266 (1987)). In order for PCP to gain access to the PCP receptor, the channel must first be opened by glutamate and glycine. In the absence of glutamate and glycine, PCP cannot bind to the PCP receptor although some studies have suggested that a small amount of PCP binding can occur even in the absence of glutamate and glycine (Sircar and Zukin, *Brain Res.* 556:280–284 (1991)). Once PCP binds to the PCP receptor, it blocks ion flux through the open channel. Therefore, PCP is an open channel blocker and a non-competitive glutamate antagonist at the NMDA receptor/channel complex.

One of the most potent and selective drugs that bind to the PCP receptor is the anticonvulsant drug MK-801. This drug has a $K_d$ of approximately 3 nM at the PCP receptor (Wong, E. H. F., et al., *Proc. Natl. Acad. Sci. USA* 83:7104–7108 (1986)).

Both PCP and MK-801 as well as other PCP receptor ligands [e.g. dextromethorphan, ketamine and N,N,N'-trisubstituted guanidines] have neuroprotective efficacy both in vitro and in vivo (Gill, R., et al., *J. Neurosci.* 7:3343–3349 (1987); Keana, J. F. W., et al., *Proc. Natl. Acad. Sci. USA* 86:5631–5635 (1989); Steinberg, G. K., et al., *Neuroscience Lett.* 89:193–197 (1988); Church, J., et al., In: *Sigma and Phencyclidine-Like Compounds as Molecular Probes in Biology*, Domino and Kamenka, eds., Ann Arbor: NPP Books (1988), pp. 747–756). The well-characterized neuroprotective efficacy of these drugs is largely due to their capacity to block excessive $Ca^{++}$ influx into neurons through NMDA receptor channels which become over activated by excessive glutamate release in conditions of brain ischemia (e.g. in stroke, cardiac arrest ischemia etc.) (Collins, R. C., *Metabol. Br. Dis.* 1:231–240 (1986); Collins, R. C., et al., *Annals Int. Med.* 110:992–1000 (1989)).

However, the therapeutic potential of these PCP receptor drugs as ischemia rescue agents in stroke has been severely hampered by the fact that these drugs have strong PCP-like behavioral side effects (psychotomimetic behavioral effects) which appear to be due to the interaction of these drugs with the PCP receptor (Tricklebank, M. D., et al., *Eur. J. Pharmacol.* 167:127–135 (1989); Koek, W., et al., *J. Pharmacol. Exp. Ther.* 245:969 (1989); Willets and Balster, *Neuropharmacology* 27:1249 (1988)). These PCP-like behavioral side effects appear to have caused the withdrawal of MK-801 from clinical development as an ischemia rescue agent. Furthermore, these PCP receptor ligands appear to have considerable abuse potential as demonstrated by the abuse liability of PCP itself.

The PCP-like behavioral effects of the PCP receptor ligands can be demonstrated in animal models: PCP and related PCP receptor ligands cause a behavioral excitation (hyperlocomotion) in rodents (Tricklebank, M. D., et al., *Eur. J. Pharmacol.* 167:127–135 (1989)) and a characteristic katalepsy in pigeons (Koek, W., et al., *J. Pharmacol. Exp. Ther.* 245:969 (1989); Willets and Balster, *Neuropharmacology* 27:1249 (1988)); in drug discrimination paradigms, there is a strong correlation between the PCP receptor affinity of these drugs and their potency to induce a PCP-appropriate response behavior (Zukin, S. R., et al., *Brain Res.* 294:174 (1984); Brady, K. T., et al., *Science* 215:178 (1982); Tricklebank, M. D., et al., *Eur. J. Pharmacol.* 141:497 (1987)).

Drugs acting as competitive antagonists at the glutamate binding site of the NMDA receptor such as CGS 19755 and LY274614 also have neuroprotective efficacy because these drugs—like the PCP receptor ligands—can prevent excessive $Ca^{++}$ flux through NMDA receptor/channels in ischemia (Boast, C. A., et al., *Brain Res.* 442:345–348 (1988); Schoepp, D. D., et al., *J. Neural. Trans.* 85:131–143 (1991)). However, competitive NMDA receptor antagonists also have PCP-like behavioral side-effects in animal models (behavioral excitation, activity in PCP drug discrimination tests) although not as potently as MK-801 and PCP (Tricklebank, M. D., et al., *Eur. J. Pharmacol.* 167:127–135 (1989)).

An alternate way of inhibiting NMDA receptor channel activation is by using antagonists at the glycine binding site of the NMDA receptor. Since glycine must bind to the glycine site in order for glutamate to effect channel opening (Johnson and Ascher, *Nature* 325:329–331 (1987); Kemp, J.

A., et al., *Proc. Natl. Acad. Sci. USA* 85:6547–6550 (1988)), a glycine antagonist can completely prevent ion flux through the NMDA receptor channel-even in the presence of a large amount of glutamate.

Recent in vivo microdialysis studies have demonstrated that in the rat focal ischemia model, there is a large increase in glutamate release in the ischemic brain region with no significant increase in glycine release (Globus, M. Y. T., et al., *J. Neurochem.* 57:470–478 (1991)). Thus, theoretically, glycine antagonists should be very powerful neuroprotective agents, because they can prevent the opening of NMDA channels by glutamate non-competitively and therefore—unlike competitive NMDA antagonists—do not have to overcome the large concentrations of endogenous glutamate that are released in the ischemic brain region.

Furthermore, because glycine antagonists act at neither the glutamate/-NMDA nor the PCP binding sites to prevent NMDA channel opening, these drugs might not cause the PCP-like behavioral side effect seen with both PCP receptor ligands and competitive NMDA receptor antagonists (Tricklebank, M. D., et al., *Eur. J. Pharmacol.* 167:127–135 (1989); Koek, W., et al., *J. Pharmacol. Exp. Ther.* 245:969 (1989); Willets and Balster, *Neuropharmacology* 27:1249 (1988); Tricklebank, M. D., et al., *Eur. J. Pharmacol.* 167:127–135 (1989); Zukin, S. R., et al., *Brain Res.* 294:174 (1984); Brady, K. T., et al., *Science* 215:178 (1982); Tricklebank, M. D., et al., *Eur. J. Pharmacol.* 141:497 (1987)). That glycine antagonists may indeed be devoid of PCP-like behavioral side effects has been suggested by recent studies in which available glycine antagonists were injected directly into the brains of rodents without resulting in PCP-like behaviors (Tricklebank, M. D., et al., *Eur. J. Pharmacol.* 167:127–135 (1989)).

However, there have been two major problems which have prevented the development of glycine antagonists as clinically useful neuroprotective agents:

A. Most available glycine antagonists with relatively high receptor binding affinity in vitro such as 7-Cl-kynurenic acid (Kemp, J. A., et al., *Proc. Natl. Acad. Sci. USA* 85:6547–6550 (1988)), 5,7-dichorokynurenic acid (DCK) (McNamara, D., et al., *Neuroscience Lett.* 120:17–20 (1990)) and indole-2-carboxylic acid (Gray, N. M., et al., *J. Med. Chem.* 34:1283–1292 (1991)) cannot penetrate the blood/brain barrier and therefore have no utility as therapeutic agents;

B. The only widely available glycine antagonist that sufficiently penetrates the blood/brain barrier—the drug HA-966 (Fletcher and Lodge, *Eur. J. Pharmacol.* 151:161–162 (1988))—is a partial agonist with micromolar affinity for the glycine binding site. A neuroprotective efficacy for HA-966 in vivo has not been demonstrated nor has it been demonstrated for the other available glycine antagonists because they lack bioavailability in vivo.

One recent success in identifying orally active glycine receptor antagonists was reported by Kulagowski et al., *J. Med. Chem.* 37:1402–1405 (1994), who disclose that 3-substituted 4-hydroxyquinoline-2(1H)-ones are selective glycine antagonism possessing potent in vivo activity.

A need continues to exist for potent and selective glycine/NMDA antagonists which can penetrate the blood/brain barrier and which:

lack the PCP-like behavioral side effects common to the PCP-like NMDA channel blockers such as MK-801 or to the competitive NMDA receptor antagonists such as CGS 19755;

show potent anti-ischemic efficacy because of the non-competitive nature of their glutamate antagonism at the NMDA receptor;

have utility as novel anticonvulsants with fewer side-effects than the PCP-like NMDA channel blockers or the competitive NMDA antagonists;

help in defining the functional significance of the glycine binding site of the NMDA receptor in vivo. International Application No. PCT/US93/09288 discloses that compounds having the formula:

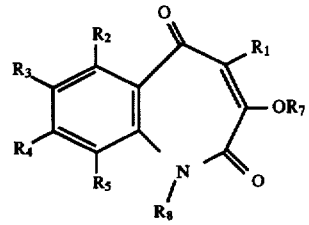

or a tautomer thereof;
wherein:

$R_1$ is hydrogen, halo, haloalkyl, alkyl, aryl, a heterocyclic group, a heteroaryl group, nitro, amino, hydroxy, alkoxy or azido;

$R_2$, $R_3$, $R_4$ and $R_5$ are hydrogen, halo, haloalkyl, aryl, fused aryl, a heterocyclic group, a heteroaryl group, alkyl, nitro, amino, cyano, acylamido, hydroxy, thiol, acyloxy, azido, alkoxy, carboxy, carbonylamido or alkylthiol;

$R_6$ is hydrogen, aryl, a heterocyclic group, a heteroaryl group, alkyl, amino, —$CH_2CONHAr$, —$NHCONHAr$, —$NHCOCH_2Ar$, —$COCH_2Ar$, hydroxy, alkoxy, aryloxy, aralkyloxy, cycloalkylalkoxy or acyloxy, wherein Ar is an aryl group or a heteroaryl group; and $R_7$ is hydrogen, acyl or alkyl;

are useful for treating or preventing neuronal loss associated with stroke, ischemia, CNS trauma, hypoglycemia and surgery, as well as treating neurodegenerative diseases including Alzheimer's disease, amyotrophic lateral sclerosis, Huntington's disease and Down's syndrome, treating or preventing the adverse consequences of the overstimulation of the excitatory amino acids, as well as treating anxiety, convulsions, chronic pain and inducing anesthesia.

International Application Publication No. WO93/25534 discloses that compounds having the Formula:

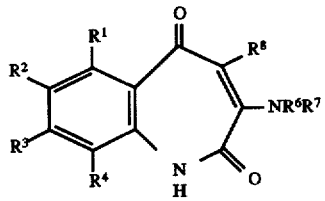

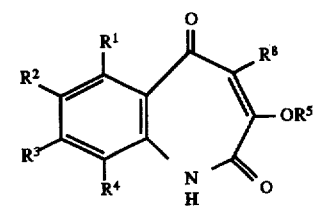

wherein $R^1$, $R^2$, $R^3$, and $R^4$ are independently selected from hydrogen, perfluoroalkyl, halo, nitro and cyano; $R^5$ is selected from hydrogen and alkyl; $R^6$ and $R^7$ are independently selected from hydrogen, alkyl, alkenyl, cycloalkyl, cycloalkylalkyl, aryl, arylalkyl, heteroaryl, heteroarylalkyl and $CH_2Y$ wherein Y is selected from $(CHOH)_nCH_2OH$ and $(CH_2)_mR^c$ wherein m is 0 to 5, n is 1 to 5 and $R^c$ is selected rom hydroxy, alkoxy, alkoxycarbonyl, carboxy, cycloalkyl, and $NR^dR^e$ in which $R^d$ and $R^e$ are independently selected from hydrogen and alkyl or $R^d$ and $R^e$, together with the nitrogen atom to which they are attached, form a 5-, 6- or 7-membered heterocyclic ring which optionally contains one additional heteroatom selected from nitrogen, oxygen and sulfur; or $R^6$ or $R^7$, together with the nitrogen atom to which they are attached, form a 5-, 6- or 7-membered heterocyclic ring which is bonded to said compound through said nitrogen atom, said heterocyclic ring optionally containing one additional heteroatom selected from nitrogen, oxygen and sulfur; $R^8$ is selected from hydrogen, halo, alkyl which may optionally bear a substituent selected from amino, acylamino, carboxy and carboxamido, arylalkyl and heteroarylalkyl; and wherein each aryl or heteroaryl moiety may be optionally substituted; and pharmaceutically acceptable salt thereof, are useful in treating neurological disorders.

Swartz et al. report that 3-hydroxy-1H-1-benzazepine-2, 5-dione (1, Table I), its 7-methyl (2) and 8-methyl (3) derivatives, act as antagonists at the strychnine insensitive glycine site associated with the NMDA receptor complex (Swartz et al., *Molecular Pharmacol.* 41:1130–1141 (1992)). In addition, U.S. Pat. No. 5,254,683 describes the synthesis and biological activities of a series of halo-substituted analogs of 1, i.e. 4–10.

TABLE I

Published Aromatic Ring Substituted Derivatives of 3-hydroxy-1H-1-benzazepine-2,5-dione

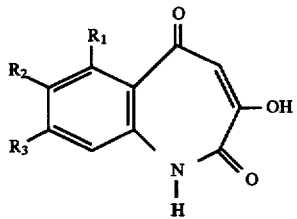

| Compound # | $R_1$ | $R_2$ | $R_3$ | $IC_{50}$ (μM) |
|---|---|---|---|---|
| 1 | H | H | H | 7.8[a] |
| 2 | H | $CH_3$ | H | See Footnote[d] |
| 3 | H | H | $CH_3$ | 3.4[a] |
| 4 | H | Cl | H | No Data[e] |
| 5 | H | H | F | 1.7[a] |
| 6 | H | H | Cl | 2.5[a]/0.030[b]/0.11[c] |
| 7 | H | H | Br | 1.3[a]/0.097[b]/1.0[e] |
| 8 | F | H | F | No Data[e] |
| 9 | Cl | H | Cl | No Data[e] |
| 10 | Br | H | Br | No Data[e] |
| 46 | H | $CH_3$ | $CH_3$ | 7.3[a,f] |

[a]Experiments described herein utilizing rat brain homogenates and a [$^3$H]-MK-801 binding assay.
[b]U.S. Pat. No. 5,254,683, utilizing rat brain homogenates and a [$^3$H]-glycine binding assay.
[c]U.S. Pat. No. 5,254,683, utilizing a guinea pig ileum contraction method.
[d]Swartz et al., Mol. Pharmacol. 41:1130–1141 (1992) lists a $K_B$ of 9.5 μM versus a value of 3.0 μM for compound 1 and 0.47 μM for compound 3.
[e]Compound described in U.S. Pat. No. 5,254,683.
[f]Compound described in Birchell et al., Can. J. Chem. 52:610–615 (1974).

Recently, efforts have been initiated to confirm the above mentioned findings and, more importantly, to improve the desired pharmacological properties of this class of compounds. To this end, compound 1 and a series of analogs were prepared and tested for biological activity (compounds 5–7, compounds 11–15, Table II and compound 16 (8-trifluoromethyl). The $IC_{50}$ for 16 was determined to be 3.4 μM utilizing rat brain homogenates and a [$^3$H]-MK-801 binding assay.) Compounds 11 and 15, which possess a substituent at position 7, were readily prepared via direct electrophilic nitration or bromination of the methyl ether of 1 (formed in situ by the ring expansion of 2-methoxynaphthalene-1,4-dione) followed by demethylation. Compounds 12 through 14 were the result of performing standard chemistry on the nitro group of the methyl ether of compound 11 (reduction with subsequent derivatization of the resulting amine) followed by demethylation. Unfortunately, all of these 7-substituted compounds, though readily prepared, proved to be ineffective glycine receptor antagonists.

TABLE II

7-Substituted Derivatives of 3-hydroxy-1H-1-benzazepine-2,5-dione Derived from Electrophilic Substitution Reactions

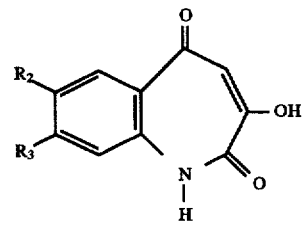

| Compound # | $R_2$ | $R_3$ | $IC_{50}$ (μM) |
|---|---|---|---|
| 11 | $NO_2$ | H | 300 |
| 12 | AcNH | H | 92.5 |
| 13 | TFAcNH | H | Inactive |
| 14 | $N^3$ | H | Inactive |
| 15 | Br | H | Inactive |
| 16 | H | $CF_3$ | 3.4 |

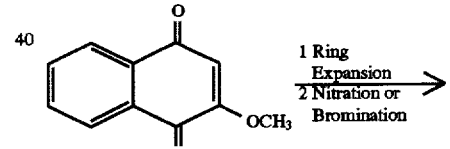

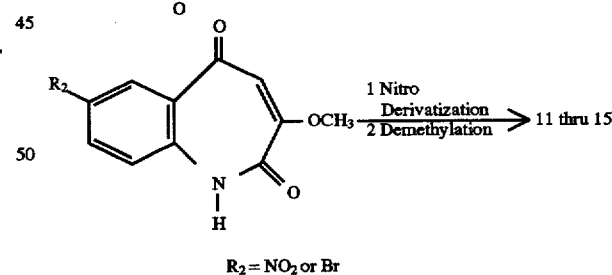

$R_2 = NO_2$ or Br

Since the direct electrophilic substitution of these benzazepines resulted in relatively inactive 7-substituted derivatives, it was desirable to prepare benzazepines with substitution at the other three available aromatic positions or at a combination of some or all of the available aromatic positions. To accomplish this required the availability of appropriately substituted 2-methoxynaphthalene-1,4-diones. Subjecting such quinones to ring expansion conditions followed by demethylation generally yield the desired benzazepines (Birchall et al., *Can. J. Chem* 52:610–615 (1974)).

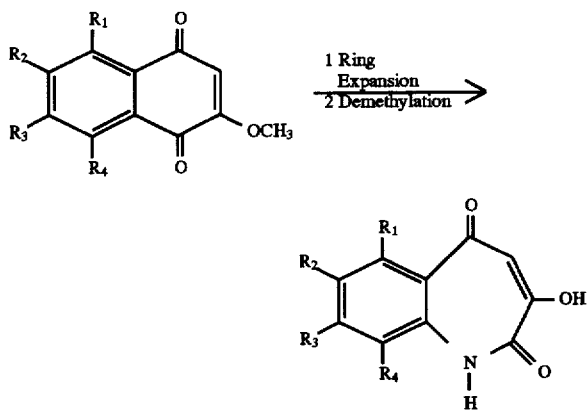

Substituted 2-methoxynaphthalene-1,4-diones are generally prepared by the methylation of the corresponding 2-hydroxy compounds (Fieser, L. J., *J. Am. Chem. Soc.* 48:2922–2937 (1926)). These enols may be obtained, for example, by the oxidation of appropriately substituted 1- or 2-tetralones, (Baillie et al., *J. Chem. Soc. (C)*:2184–2186 (1966)) by the hydrolysis of 2-anilinonaphthalene-1,4-diones (Lyons et al., *J. Chem. Soc.* 2910–2915 (1953)) or by the hydrolysis and oxidation of 1,2,4-triacetoxynaphthalenes (Thiele et al., *Ann. Chem.* 311:341–352 (1900)). Another general method to 2-methoxynaphthalene-1,4-diones involves a 6 step synthesis starting from 3,4-diisopropoxy-3-cyclobutene-1,2-dione incorporating an appropriately substituted aryl lithium compound (U.S. Pat. No. 5,254,683). These various methods are outlined in Scheme I.

All of these methods have inherent disadvantages. The cyclobutenedione method involves six steps (four from a common intermediate) and involves the use of various highly reactive lithium reagents. The anilinonaphthoquinone and triacetoxynaphthalene methods require substituted naphthalene-1,4-diones as precursors. These, like substituted 2-methoxynaphthalene- 1,4-diones, are not readily available. In addition, the oxidation reaction of 7-halo or 7-perfluoroalkyl-1-tetralones processed in only moderate yield (25–40%). Oxidations of 1-tetralones possessing nitrogen substituents, such as nitro, amino, acetamido or azido, failed to yield any desired product. Attempted oxidations of 5-halo-1-tetralones failed in our hands. Also, the preparation of substituted tetralones is, in general, laborious. Direct electrophilic substitution of 1-tetralone gives an isomeric mixture, which must be separated chromatographically. Other methods of synthesizing 1-tetralones generally involve the cyclization of substituted 4-phenylbutyric acids. Such butyric acids may be prepared by the succinylation of substituted benzenes followed by the reduction of the resulting γ-ketopropionic acid (Blatt, A. H., *Organic Syntheses*, John Wiley & Sons, Inc., New York, Collect. Vol. 2, pp 81 and 499 (1943)) or via multistep syntheses such as those starting from substituted benzaldehydes (Beugelmans et al., *J. Org. Chem.* 50:4933–4938 (1985) or aryltributylstannanes (Owton et al., *Synth. Commun.* 21:981–987 (1991)). Some of these cumbersome methods have been used by us for the preparation of a variety 8-substituted 3-hydroxy-1H-1-benzazepine-2,5-diones (5, 6, 7 and 16, see Scheme II).

Finally, the cyclobutenedione method involves the use of highly reactive lithium reagents which cannot be used to prepare analogs of 3-hydroxy-1H-1-benzazepine-2,5-diones having one or more nitrogens in the benzene ring. This method requires the reaction of a substituted orthobromopyridine with n-butyllithium. The reaction between halopyridines and n-butyllithium is known to proceed by either the addition of n-butane to the 4-position or metalation at the 3-position, but not metalation at the 2-position (Gubble and Saulnier, *Tet. Lett.* 21:4137 (1980); Foulgner and Wakefield, *J. Organ. Met. Chem.* 69:161 (1974)). These metalation reactions are not specific and usually give a variety of products.

Scheme I

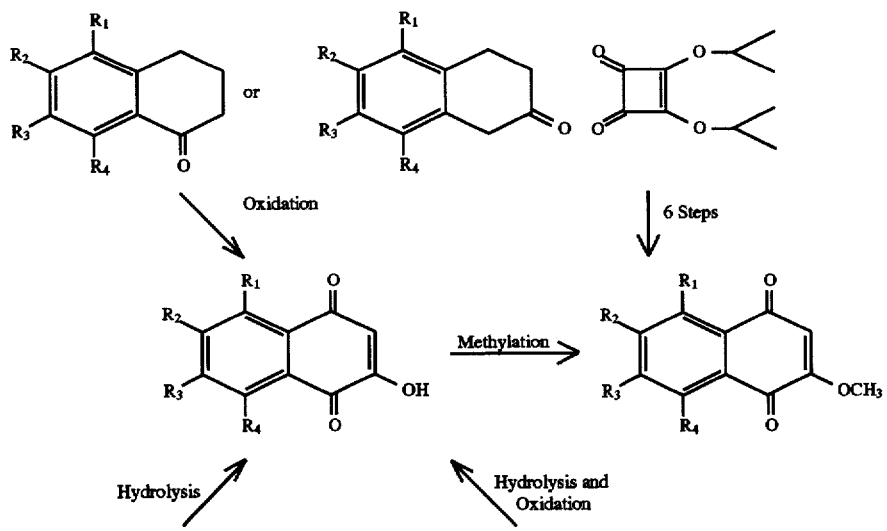

-continued
Scheme I
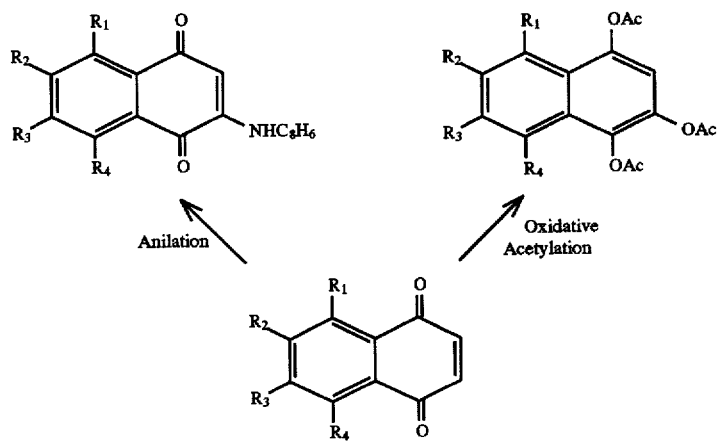
Scheme II
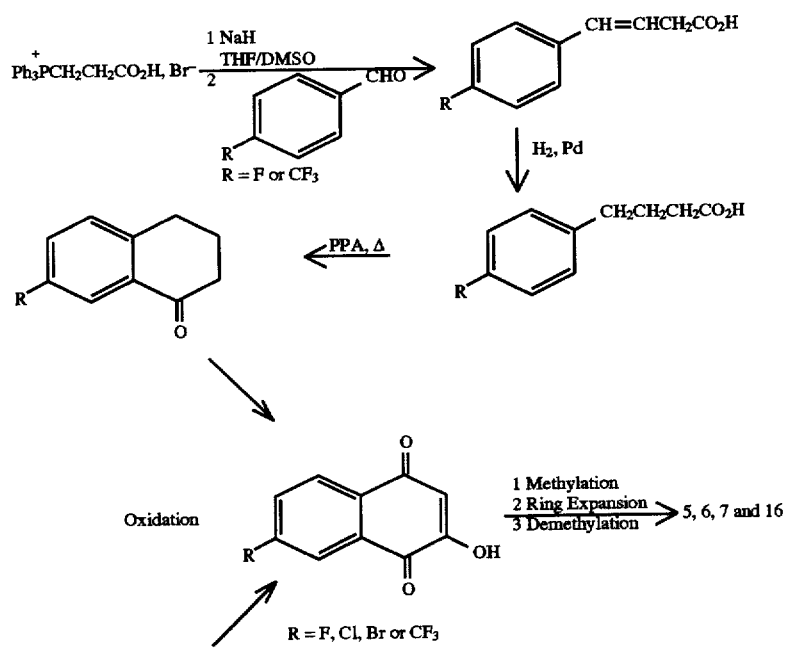

-continued
Scheme II

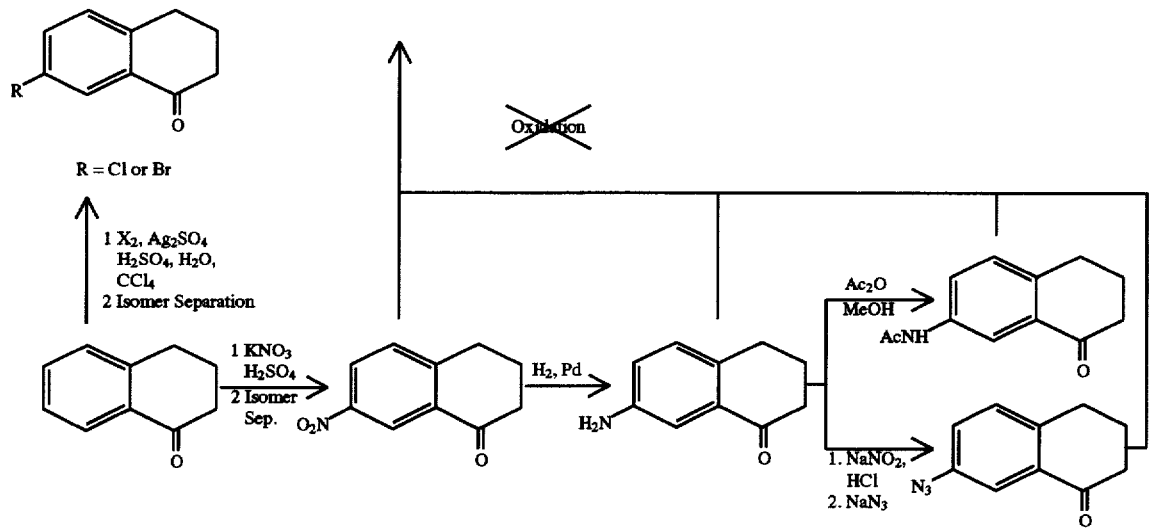

SUMMARY OF THE INVENTION

In order to find a more efficacious method of preparing the needed 2-methoxynaphthalene-1,4-diones, we began to investigate the applicability of Diels-Alder chemistry. The Diels-Alder reaction has been extensively utilized as a powerful synthetic tool for the preparation of a variety of complex organic compounds. Some recent examples include the synthesis of analogs of the antifungal agent sampangine (Clark et al., Int. Pat. Appl. WO 92/22297 (1992)), the total synthesis of ellipticine alkaloids and their amino analogs (Sha et al., Tetrahedron 48:10645–10654 (1992)), potential synthetic intermediates for tetracycline antibiotics (Mikami et al., Asymmetry 2:643–646 (1991)), and the synthesis of leukotrienes (Donaldson et al., J. Org. Chem. 56:4563–4566 (1991)). For our application, Bohlmann et al. (Bohlmann et al., Chem. Ber. 110:2028–2045 (1977)) reported the preparation of three substituted 2-methoxynaphthalene-1,4-diones in 2 steps from a common intermediate, i.e., 2-methoxynaphthalene-1,4-dione (17).

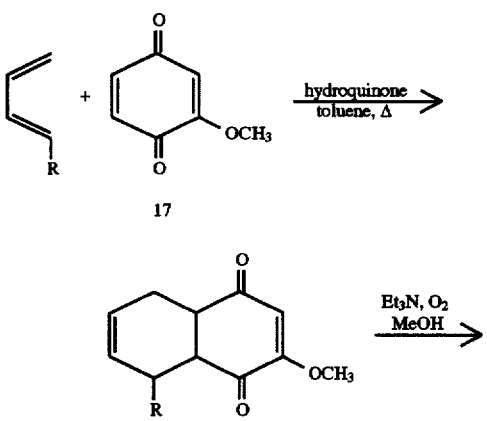

Also, Giles et al. (Giles et al., J. Chem. Soc. Perkin Trans. 1:2057–2060 (1976); Giles et al., J. Chem. Soc. Perkin Trans. 1:1632–1635 (1976); Giles et al., Tetrahedron Lett.:4159–4160 (1975)) reported the preparation of 2,8-dimethoxynapthalene-1,4-dione in four steps from this same intermediate.

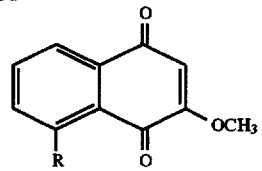

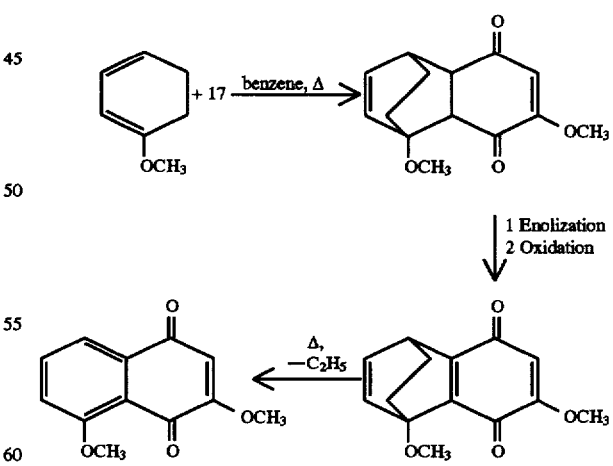

Finally Boisvert et al. (Boisvert, L. et al. Tetrahedron Lett. 24:2453–3456 (1983)) described the synthesis of methyl substituted 2-methoxynaphthalene-1,4-diones utilizing a Diels-Alder reaction of 1-acetoxybutadienes with 2-chloro-4-methoxybenzoquinone.

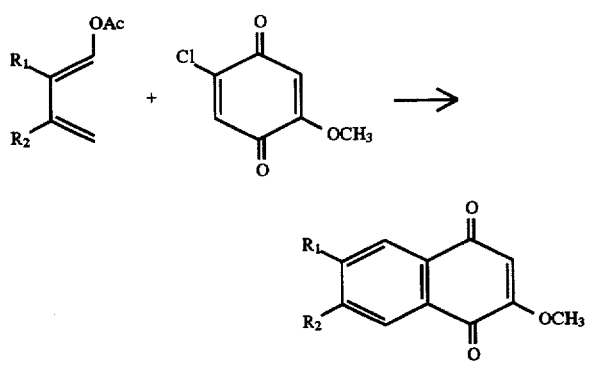

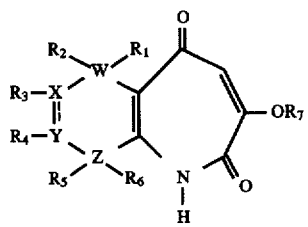

$R_1 = CH_3\ R_2 = H$
or
$R_1 = H\ R_2 = CH_3$

The invention relates to a process for the preparation of a compound having the Formula (I):

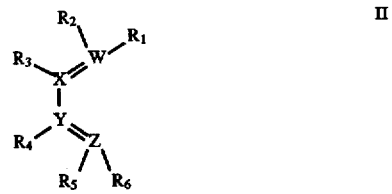

or a tautomer thereof;

W is carbon, nitrogen, oxygen or sulfur;

X is carbon or nitrogen;

Y is carbon or nitrogen; and

Z is carbon, nitrogen, oxygen or sulfur;

the bond between X and Y is single;

$R_1$–$R_6$ are hydrogen, halo, haloalkyl, aryl, fused aryl, a heterocyclic group, a heteroaryl group, alkyl, alkenyl, alkynyl, arylalkyl, arylalkenyl, arylalkynyl, hydroxyalkyl, nitro, amino, cyano, acylamido, hydroxy, thiol, acyloxy, azido, alkoxy, carboxy, carbonylamido, alkylthiol, trialkylsilyloxy, or phenyldialkylsilyloxy; or $R_1$ and $R_2$ or $R_5$ and $R_6$ are an unshared electron pair where W and Z, respectively, are oxygen or sulfur; or one of $R_1$ and $R_2$, or $R_3$, or $R_4$, or one of $R_5$ and $R_6$ is an unshared electron pair when W, X, Y or Z respectively is nitrogen; or where $R_1$ and $R_6$ together are a $C_{1-4}$ alkylene bridge, a substituted $C_{1-4}$ alkylene bridge, an oxygen bridge, or an amine bridge, wherein the substituent is a halo, haloalkyl, aryl, fused aryl, a heterocyclic group, a heteroaryl group, alkyl, acyl, nitro, amino, cyano, acylamido, alkoxy, carboxy, carbonylamido or alkylthiol group; and $R_7$ is alkyl, alkanoyl, trialkylsilyl, phenyldialkylsilyl or tetrahydropyranyl; with the proviso that X and Y are not other than carbon at the same time and that when one of W and Z is oxygen or nitrogen, then the other of W and Z is carbon;

by the Diels-Alder reaction of an compound having the Formula (II):

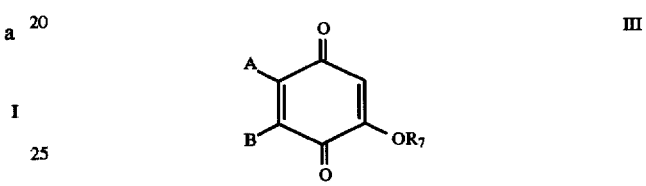

where $R_1$–$R_6$ are defined above and, in addition, $R_1$ and $R_6$ may be an oxygen bridge, a sulfur bridge, an amino bridge (N—$R_8$, where $R_8$ is alkyl, or acyl), a methamino bridge or a substituted methamino bridge where the substituent is a halo, haloalkyl, aryl, fused aryl, a heterocyclic group, a heteroaryl group, alkyl, nitro, amino, cyano, acylamido, alkoxy, carboxy, carbonylamido or alkylthio group; and where the compound having Formula II may exist as a mixture of cis and trans isomers;

with a dienophile having the Formula (III):

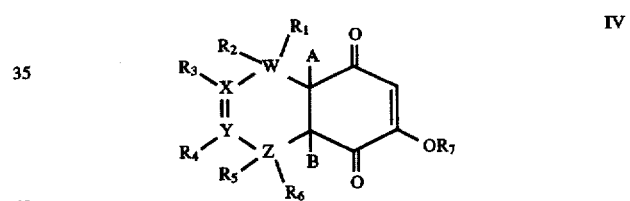

wherein at least one of A and B is hydrogen and the other of A and B is hydrogen, alkoxy, chloro, bromo, iodo, tosyl or mesityl; and $R_7$ is alkyl, alkanoyl, trialkylsilyl, phenyldialkylsilyl or tetrahydropyranyl;

to give a compound having the Formula (IV):

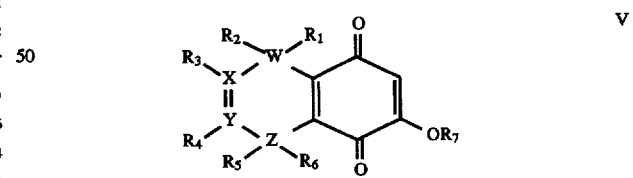

It is to be understood that a mixture of regioisomers and/or diasteriomers may be obtained by this reaction which may be separated chromatographically or by crystallization at this or a later stage of the process.

If one of A and B is other than hydrogen, then the compound having Formula IV is an intermediate which eliminates A—B to give a compound having Formula (V):

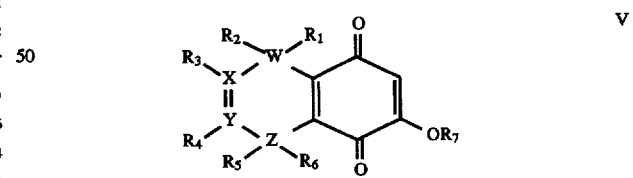

Where $R_1$ and $R_6$ together are not a $C_{1-4}$ alkylene bridge, a substituted $C_{1-4}$ alkylene bridge, an oxygen bridge, a sulfur bridge, an amino bridge, a methanimino bridge or a substituted methanimino bridge, and where A and B are hydrogen, the compound having Formula IV can be converted into the quinone having formula V by a two-step process involving enolization then oxidation of the hydroquinone intermediate. Further oxidation is often possible, resulting in the corresponding aromatic quinone. The X=Y double bond of formula V may be removed by hydrogenation, a process that results also in reduction of the quinone to the hydroquinone which must be reoxidized to the quinone. Thus, the preferred route to the saturated analogs is enolization of IV to the hydroquinone, hydrogenation of the X=Y double bond, and then oxidation of the hydroquinone portion to the quinone having Formula V with X and Y being connected with a single bond. Reaction with azide then leads to the corresponding azepine I. Where X and Y are both carbon, then the double bond in V can be derivatized in some other manner such as oxidation to the diol which might be further alkylated, halogenation, nitration employing N₂O₄ or epoxidation employing metachloroperoxybenzoic acid.

Where $R_1$ and $R_6$ together are an oxygen bridge, a sulfur bridge, an amino bridge, a methanimine bridge or a substituted methanimine bridge, a tricyclic intermediate is formed which may spontaneously ring open and eliminate water, hydrogen sulfide, an amino compound, hydrogen cyanide or a nitrile (a substituted cyanide). This ring-opened product is the quinone, naphthoquinone, or heteronaphthoquinone and may be reacted with azide to give the corresponding azepine. Where the tricyclic intermediate does not spontaneously ring open, e.g., when the diene is cyclohexadiene, cyclopentadiene, N-carbethoxypyrrole, furan or 2-methoxyfuran, the tricyclic intermediate may be carried on to the corresponding azepine by enolization of V, then hydrogenation of the 6,7-double bond, oxidation to the quinone and reaction with azide. Where the diene is cyclopentadiene, elimination of the methylene bridge to give the naphthoquinone may be carried out in a protic solvent such as acetic acid.

In particular, the invention relates to a method for the preparation of a compound having Formula (VI):

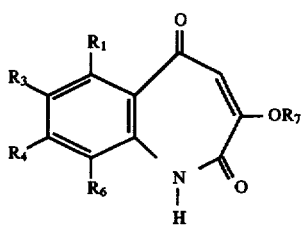

VI wherein $R_1$, $R_3$, $R_4$, $R_6$ and $R_7$ are defined above, by the Diels-Alder reaction of a compound having Formula (VII):

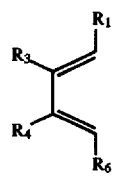

VII which may exist as a mixture of cis and trans isomers, with the quinone having Formula III, to give a compound having Formula (VIII):

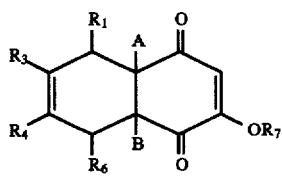

VIII

Where one of A and B is other than hydrogen, A—B eliminates spontaneously to give the corresponding quinone which is then oxidized to the naphthoquinone. Otherwise, when A and B are hydrogen, the intermediate having Formula VIII may be oxidized directly to the naphthoquinone and reacted with azide to give the compound having Formula VI.

Alternatively, compounds of Formula IX may be prepared by spontaneous elimination of A—B from Formula VIII, then catalytic reduction to the corresponding 5,6,7,8-tetrahydronaphthlenehydroquinone, then reoxidation to the quinone and then reaction with azide. The reason for having the alternative route is to allow control of the regiochemistry of the Diels-Alder reaction through manipulation of A and/or B.

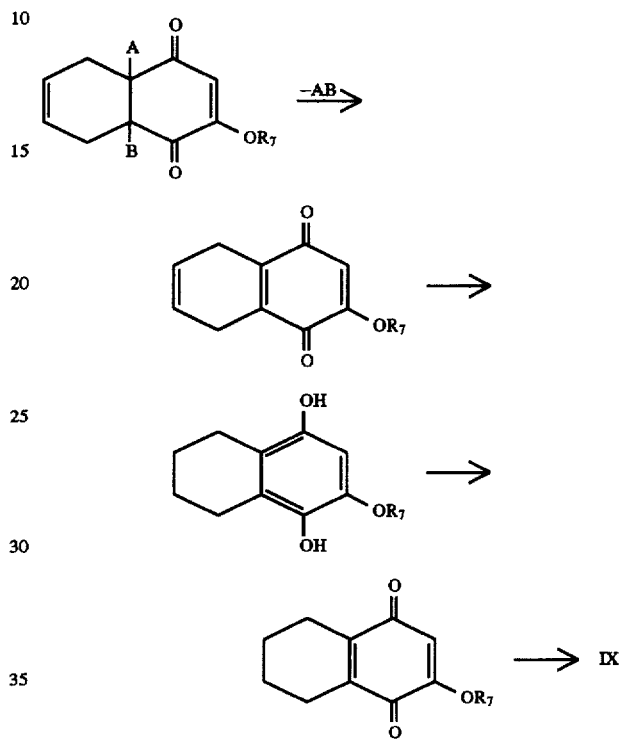

Thus, a compound having Formula IX

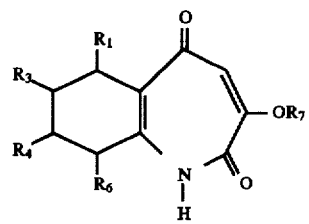

IX may be prepared by enolization of the intermediate VIII (A and B are hydrogen in this example) to give a compound having Formula X:

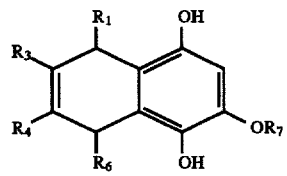

X followed by hydrogenation to give a compound having Formula XI:

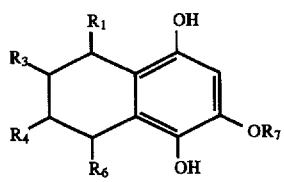

followed by oxidation to the quinone and treatment with azide to give the compound having Formula IX.

The invention also relates to a method for preparing an azepine having the formula:

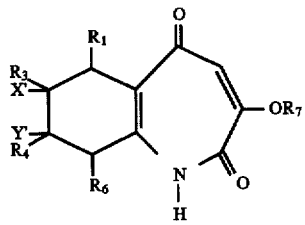

wherein $R_1$, $R_3$, $R_4$, $R_6$ and $R_7$ ($\neq$H) are defined above, and X' and Y' are independently halogen; hydroxy and hydrogen; nitro and hydrogen; alkanoylamido and hydrogen; X' and Y' together form an oxirane ring; or X' and Y' are vicinal alkanoylamido alkanoyloxy groups; comprising (a) the Diels-Alder reaction of the compound having Formula VII with the quinone having Formula III to give the compound having Formula VIII (b) enolization to the corresponding hydroquinone;

(c) halogenation; hydroboration/oxidation; nitration; nitration, reduction of the nitro group to an amine followed by acylation of the amine; expoxidation; or epoxidation, ring opening with an amino compound, and acylation; respectively, to give a compound having the formula:

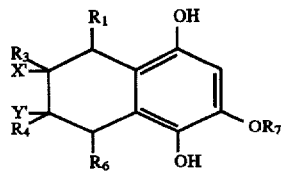

(d) oxidation W give the corresponding quinone; and (e) reaction with azide in acidic solution to give said azepine.

Where X' and Y' are chlorine, the double bond may be regenerated by reaction with Zn/ethanol.

The invention also relates to a method for preparing an azepine having the formula:

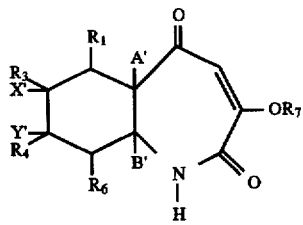

wherein $R_1$, $R_3$, $R_4$, $R_6$ and $R_7$ ($\neq$H) are defined above, X' and Y' are independently halogen; hydroxy and hydrogen;

nitro and hydrogen; alkanoylamido and hydrogen; X' and Y' together form an oxirane ring; or X' and Y' are vicinal alkanoylamido alkanoyloxy groups; and where one of A' and B' is hydrogen and the other of A' and B' is alkyl or aralkyl, comprising (a) the Diels-Alder reaction of the compound having Formula VII with a quinone having the Formula:

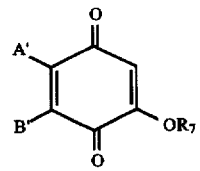

where A', B' and $R_7$ are defined above, to give a compound of the Formula:

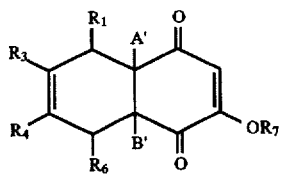

(b) halogenation; hydroboration/oxidation; nitration; nitration, reduction of the nitro group to an amine followed by acylation of the amine; expoxidation; or epoxidation, ring opening with an amino compound, and acylation; respectively, to give a compound having formula:

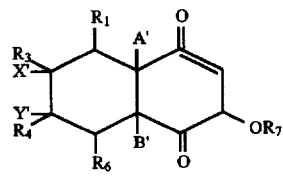

and (c) reaction with azide in acidic solution to give said azepine.

Where X' and Y' are chlorine, the double bond may be regenerated by reaction with Zn/ethanol.

The invention also relates to a method for the preparation of a compound having the Formula XII:

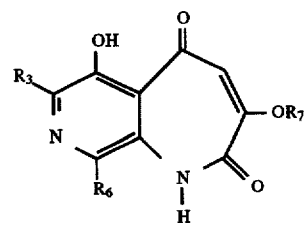

and/or its isomer having the Formula XIII:

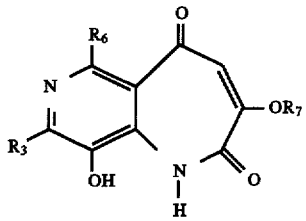

wherein $R_3$, $R_6$ and $R_7$ are defined above, by the Diels-Alder reaction of the oxazole having Formula XIV:

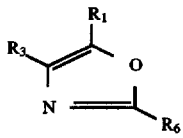

wherein $R_1$ is alkoxy,
with the quinone having Formula III (A and B are hydrogen in this example), to give a compound having Formula XV:

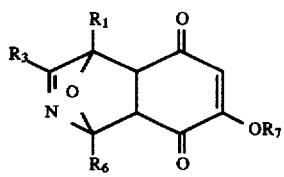

and/or its isomer having the Formula XVI:

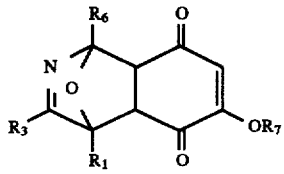

followed by the spontaneous elimination of $R_1H$ (an alcohol) and ring opening to give a compound having Formula XVII:

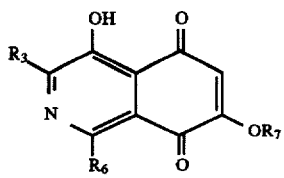

and/or its isomer having Formula XIX:

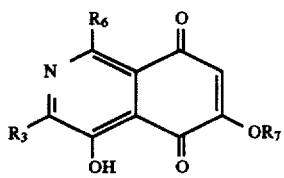

followed by reaction with azide to give the compound having Formula XII or XIII, respectively.

In the above example, when one of A and B is other than hydrogen, the quinones having Formulas XVa and XVIa (below) are obtained. These quinones may be ring opened with a suitable reducing agent (such as Zn/EtOH) followed by the elimination of $R_1$—H (an alcohol) to give the compounds having Formulas XVII and XIX

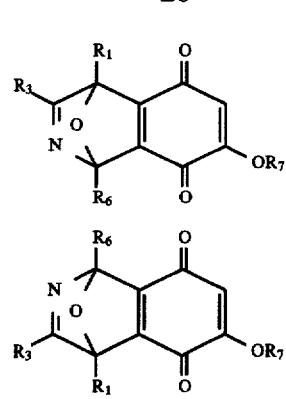

The invention also relates to the preparation of the aryl N-oxides of the compounds having Formulae XII and XIII by the N-oxidation thereof.

The invention also relates to a method for the preparation of a compound having Formula XX:

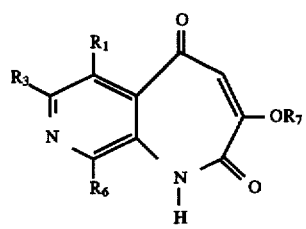

and/or its isomer having Formula XXI:

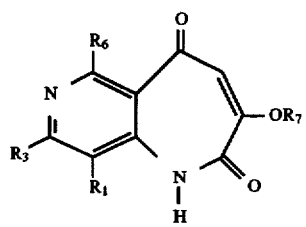

wherein $R_1$, $R_3$, $R_6$ and $R_7$ are defined above,
by the Diels Alder reaction of the compound having Formula XIV ($R_1$ is hydrogen) with the quinone having Formula III (A and B are hydrogen in this example) to give the intermediates having Formulas XV and/or XVI ($R_1$ is hydrogen). The spontaneous ring opening of the cyclic ether and elimination of water give a compound having Formula XXII:

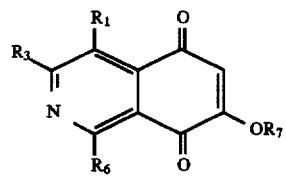

and/or its isomer having Formula XXIII:

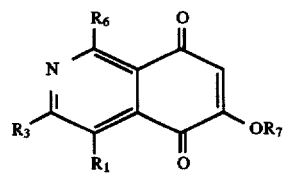

Where one of A and B is other than hydrogen, the corresponding quinones XVa and XVIa ($R_1$=H) are obtained directly, which may be treated with a suitable reducing agent (Zn/EtOH) to give (after elimination of water) XXII and XXIII. Reaction with azide in acidic solution gives the compounds having Formulas XX and/or XXI, respectively.

The invention also relates to a method for the preparation of a compound having Formula XXIV:

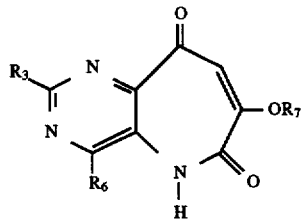

and/or its isomer having Formula XXV:

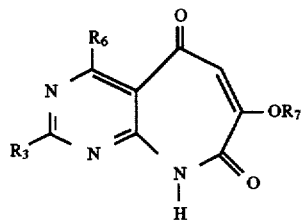

wherein $R_3$, $R_6$ and $R_7$ are defined above, by the Diels-Alder reaction of a triazine having Formula XXVI:

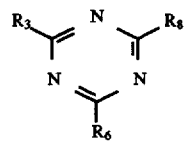

where $R_8$ is hydrogen, alkyl or aryl;

with the quinone having Formula III (one of A and B is other than hydrogen) to give the intermediate having Formula XXVII:

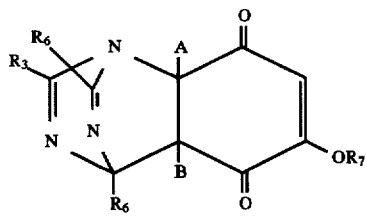

and/or its isomer having Formula XXVIII:

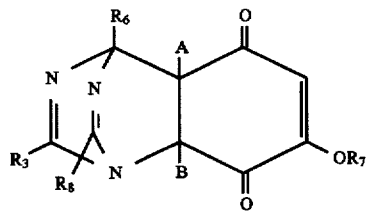

which eliminates $R_8$—CN and A—B (if necessary, in the presence of a base such as triethylamine) to give the intermediate having Formula XXIX:

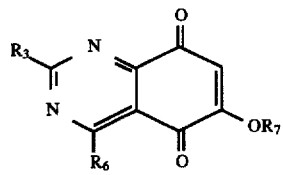

and/or its isomer having Formula XXX:

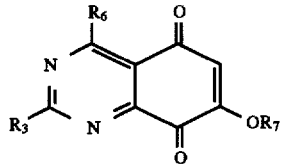

followed by reaction with azide to give the compounds having Formula XXIV and/or XXV, respectively.

The invention also relates to the preparation of the aryl N-oxides of the compounds having Formulae XXIV and XXV by the N-oxidation thereof.

The invention also relates to a method for the preparation of a compound having Formula XXXI:

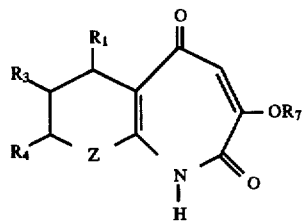

and/or its isomer having Formula XXXII:

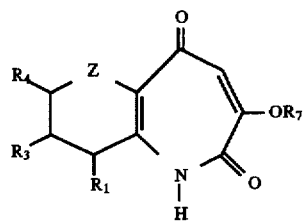

wherein $R_1$, $R_3$, $R_4$ and $R_7$ are defined above, and wherein Z is oxygen, sulfur or nitrogen which may be substituted by a trialkylsiloxy or phenyldialkylsiloxy group, by the Diels-Alder reaction of the diene having Formula XXXIII:

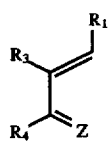

with the quinone having Formula III (A and B are hydrogen in this example; but one of A and B may be other than hydrogen whereby the quinone is obtained directly) to give a compound having Formula XXXIV:

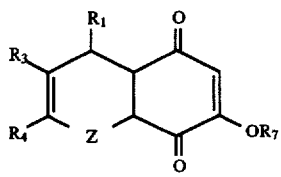

and/or its isomer having Formula XXXV:

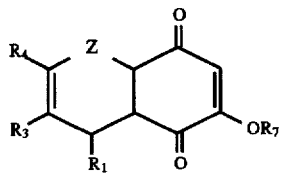

followed by enolization to give the hydroquinone and hydrogenation to give a compound having Formula XXXVI:

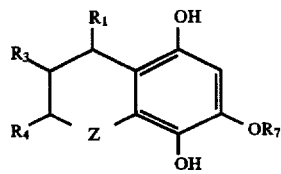

and/or its isomer having Formula XXXVII:

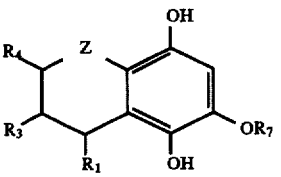

and oxidation to give the quinone having Formula XXX-VIII:

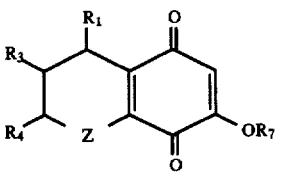

and/or its isomer having Formula XXXIX:

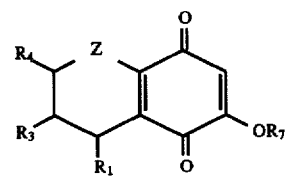

and reaction with azide to give the compounds having Formula XXXI and XXXII, respectively.

The invention also relates to the preparation of the heteroarylazepine having the Formula XXXIa:

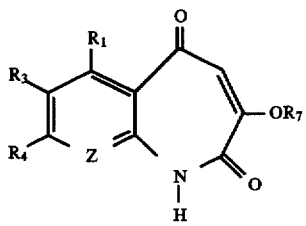

and/or its isomer having Formula XXXIIa:

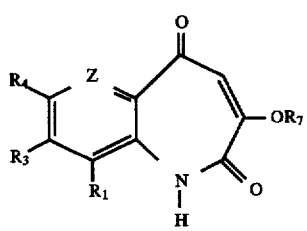

where Z is limited to nitrogen, by the oxidation of the intermediates having Formulae XXXIV and XXXV to the corresponding azanaphthalenequinones and reaction with azide to give the heteroarylazepine. Alternatively, one of A and B may be other than hydrogen and the Diels-Alder reaction gives a quinone corresponding to Formulae XXXIV and XXXV. Oxidation to the azanaphthalenequinone and reaction with azide gives XXXIa and XXXIIa.

The invention also relates to the corresponding aryl N-oxides of XXXIa and XXXIIa having the Formulae:

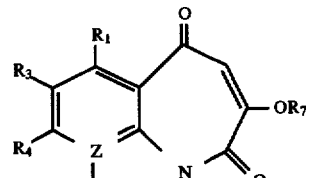

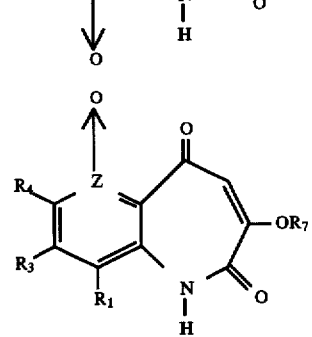

by N-oxidation of the compounds having Formulae XXXIa and XXXIIa.

The invention also relates to a method for the preparation of a compound having Formula XL:

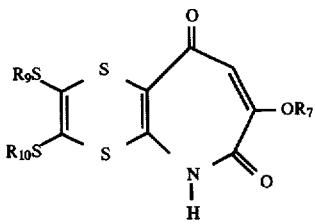

where $R_9$ and $R_{10}$ are independently alkyl and $R_7$ is defined above, by the Diels-Alder reaction of the compound having Formula XLI:

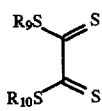

with the quinone having Formula III to give a compound having Formula XLII:

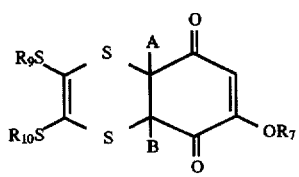

Where one of A and B is other than hydrogen, A—B eliminates to give the quinone. When A and B are hydrogen, oxidation to the quinone and reaction with azide gives the compound having Formula XL.

The invention also relates to a method of treating or preventing neuronal loss associated with stroke, ischemia, CNS trauma, hypoglycemia and surgery, as well as treating neurodegenerative diseases including Alzheimer's disease, amyotrophic lateral sclerosis, Huntington's disease and Down's syndrome, treating or preventing the adverse consequences of the overstimulation of the excitatory amino acids, as well as treating anxiety, convulsions, chronic pain, inducing anesthesia, and for preventing opiate tolerance, comprising administering to an animal in need of such treatment an effective amount of any one of the azepines disclosed herein, as well as the aryl N-oxides thereof (preferably, $R_7$ is hydrogen or alkyl), in addition to the 3-amino analogs thereof, or a pharmaceutically acceptable salt thereof.

DESCRIPTION OF THE PREFERRED EMBODIMENTS

The process of the present invention has the potential for enormously increasing the number and variety of substituted 2-oxy (e.g. alkoxy) naphthalene-1,4-diones and hetero analogs available for the synthesis of 3-hydroxy-1H-1-azepine-2,5-diones and the hetero analogs thereof. Examples of many previously unknown quinones and azepines have been prepared according to the processes of the present invention. The availability of suitable dienes is not a limitation. A host of potential Diels-Alder dienes are available commercially or are described in the chemical literature. The Aldrich Chemical Co., one of many companies that supply research chemicals, sells 85 conjugated dienes that have potential use in the practice of the invention. Such dienes include 1,3-hexadiene (predominantly trans), 2,4-hexadiene (mixture of isomers), trans-2-methyl-1,3-pentadiene, trans-piperylene, hexachloro-1,3-butadiene, 2,4-dimethyl-1,3-pentadiene, 2,3-dimethyl-1,3-butadiene, ethyl sorbate, 2,4-hexadienal, trans,trans-2,4-decadienal, trans,trans-2,4-heptadienal, trans,trans-2,4-nonadienal, trans,trans-2,4-hexadien-1-ol, trans-1-methoxy-3-(trimethylsilyloxy)-1,3-butadiene, 1-acetoxy-1,3-butadiene (mixture of cis and trans), 1-(trimethylsilyloxy)-1,3-butadiene (mixture of isomers), 5,7-dimethyl-3,5,9-decatrien-2-one, 2,4-hexadienoic acid, trans-8, trans-10-dodecadien-1-yl acetate, cis-9, trans-11-tetradecadien-1-yl acetate, trans-8,trans-10-dodecadien-1-ol, trans-7,cis-9-dodecadien-1-yl acetate, cis-piperylene, 3-methyl-1,3-pentadiene (mixture of cis and trans), 2,3-dimethoxy-1,3-butadiene, trans-2-methyl-1,3-pentadiene, 2,6-dimethyl-2,4,6-octatriene (mixture of isomers), 2,3-bis (trimethylsilyloxy)-1,3-butadiene, 1,3-butadiene, trans-2,4-pentadienoic acid, 2,5-dimethyl-2,4-hexadiene, cis,cis-mucononitrile, trans,trans-2,4-hexadienoic acid (potassium salt), 1-(triethylsilyloxy)-1,3-butadiene (mixture of cis and trans), 3-(tert-butyldimethylsilyloxy)-1-methoxy-1,3-butadiene, 2,5-dimethyl-2,4-hexadiene, 2,4-hexadienoic acid, 1,3,5-hexatriene, isoprene, 1-methoxy-1,3-butadiene, trans,trans-muconic acid, myrcene, piperylene, pentachloro-cis-2,4-pentadienoic acid, 5-methyl-1,3,6-heptatriene, cis, cis-2,5-dimethylmuconic acid, 2,4,6-octatrienoic acid, 3,7-dimethyl-1,3,6-octatriene, pseudoionone, methyl N-isopropyl-N-(3-methyl-1,3-butadien-1-yl)carbamate, perchloro-1,3,5-hexatriene, 5-bromo-5-hexen-1-yl 2,4-hexadien-1-yl ether, methyl 5-methyl-2,4,6-octatriene-2-carboxylate, methyl 2,4,4-undecatriene-2-carboxylate, dimethyl 2-(3-methyl-2-buten-1-ylidene)succinate, methyl 6-hydroxy-2,4-heptadiene-2-carboxylate, 2,4-dimethyl-1,3-pentadiene-1-carboxylic acid, 2,4-hexadien-1-yl acetate, 5-methyl-2,4-hexadiene-2-carboxamide, 4-methyl-1,3-pentadiene-1-carboxaldehyde, di methyl 2,4,6,8-decatetraene-2,9-dicarboxylate, 4-bromo-4-penten-1-yl 2,4-hexadien-1-yl ether, 1,3,5-octatriene-1-carboxaldehyde dimethyl acetal, methyl 4-methyl-2,4,6-octatriene-2-carboxylate, 2,4-nonadiene-2-carboxaldehyde, 1-methyl 2,4-dimethyl-2,4-hexadienoate, dimethyl 2-methylmuconate, 2,5-dimethyl-3,5-hexadien-2-ol, 4-methyl-1,3-octadiene, dimethyl 1,3,5-heptatriene-1,6-dicarboxylate, methyl 2-methylene-4-decenoate, methyl 2-methyl-2,4-decadienoate, mono-methyl 2-methylmuconate, octachloro-1,3-pentadiene, 1-bromo-4, 4-dichloro-1,3-butadiene-1-carboxylic acid, heptachloro-2, 4-pentadiene-1-carboxamide, methyl 1-bromo-4,4-dichloro-1,3-butadiene-1-carboxylate, 1,2,3,4,4-pentachloro-1,3-butadiene-1-carboxamide, 2,3-dibromo-5,5-dichloro-4-methyl-2,4-pentadien-1-ol, 1,2,3,4,5,6,6-heptachloro-1,3,5-hexatriene-1-carboxaldehyde, methyl 2-oxo-3,4,5,6,6-pentachloro-3,5-hexadiene-1-carboxylate, 1,2,3,4,4-pentachloro-1,3-butadiene-1-carbonitrile, 4-bromo-1,2,3,4-tetrachloro-1,3-butadiene-1-carboxylic acid, N-methyl-1,2, 3,4,4-pentachloro-1,3-butadiene-1-carboxamide, and 1-cyclopentyl-1-phenylethene.

Since the Diels-Alder reaction is such a powerful synthetic tool, a great deal of research has been and currently is being performed on the preparation of novel dienes. A few examples from the current literature include 2-and/or 3-silyl, selenyl, stannyl, alkyl, halo or carboxy-1,3-butadienes (Reich et al., *J. Am. Chem. Soc.*, 115:6625–6635 (1993)), 2-(dialkoxyboryl)-1,3-butadienes (Kamabuchi et al., *Tet. Lett.* 34:4827–4828 (1993)), and spirosilyltetraenes (Horn et al., *Tet. Lett.* 34:5889–5892 (1993)). See also Fringuelli, F.

et al., *Dienes in the Diels-Alder Reaction*, John Wiley & Sons, Inc., New York, (1990). Any of these dienes may also be employed in the precesses of the present invention.

Certain combinations of diene and dienophile fail to react or react slowly in a Diels-Alder manner. However, Lewis Acid catalysts greatly facilitate the Diels-Alder reactivity of otherwise unreactive combinations (Yates et al., *J. Am. Chem. Soc.* 82:4436–4437 (1960); Pray et al., *J. Am. Chem. Soc.* 83:249 (1961); Fringuelli, F. et al., *Dienes in the Diels-Alder Reaction*, John Wiley & Sons, Inc., New York, (1990), pp. 1–44). Such catalytic methods have the potential of allowing the use of poorly reactive dienes, such as 1-nitro-1,3-butadiene (Bloom et al., *Tetrahedron Lett.* 27:873–876 (1986)), in the Diels-Alder scheme.

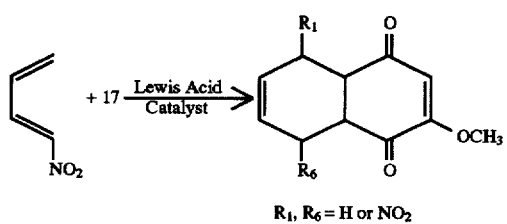

$R_1, R_6 = H$ or $NO_2$

The technique of employing heteroatom bearing dienes, such as 2-azabutadienes, 1,3,5-triazines, α,β-unsaturated carbonyl compounds, α,β-unsaturated dithioesters, 1,2-dithiocarbonyl compounds (Boger, D. L., *Hetero Diels-Adler Methodology in Organic Synthesis*, Wasserman, H. H., Vol. 47 Academic Press, Inc., San Diego (1987), pp. 167–357); oxazoles (Yoshikawa et al., *Chem. Pharm. Bull.* 13:873–878 (1965); Naito et al., *Chem. Pharm. Bull.* 14:918–921 (1966); Takagaki et al., *Chem. Lett.* 183–186 (1979); 1,3-diazabutadienes, 1-thio-3-azabutadienes, 1,3-diaza-4-oxabutadienes, 1-oxa-3-diazabutadienes (Fringuelli et al., Dienes in the Diels-Alder Reaction, John Wiley & Sons, Inc., New York (1990), pp. 97–106); and N-silyloxy-1-azabutadienes (Behforouz et al., *J. Org. Chem.* 58:7089–7091 (1993)) has been extensively used for the synthesis of heterocyclic Diels-Alder adducts. This offers a pathway for the synthesis of numerous heterocyclic analogs of 3-hydroxy-1H-1-azepine-2,5-dione. Examples of potential pathways are illustrated in Scheme III.

Some examples of Diels-Alder reactions performed and naphthalene-1,4-diones prepared are shown in Table III (for simplicity only one possible regioisomer for each Diels-Alder reaction is shown).

Scheme III

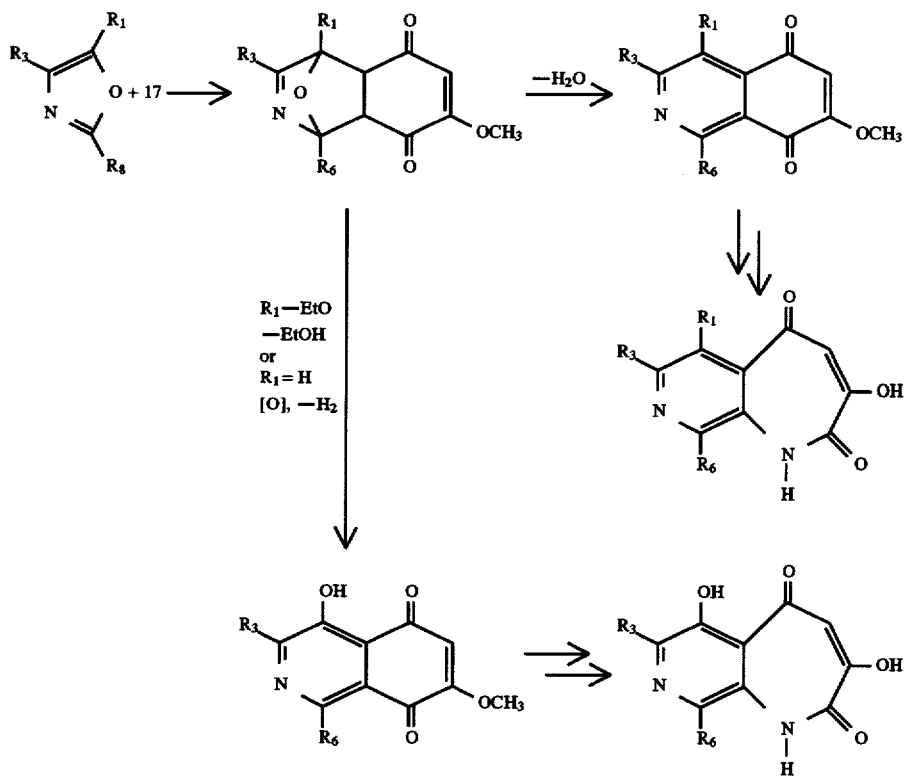

-continued
Scheme III
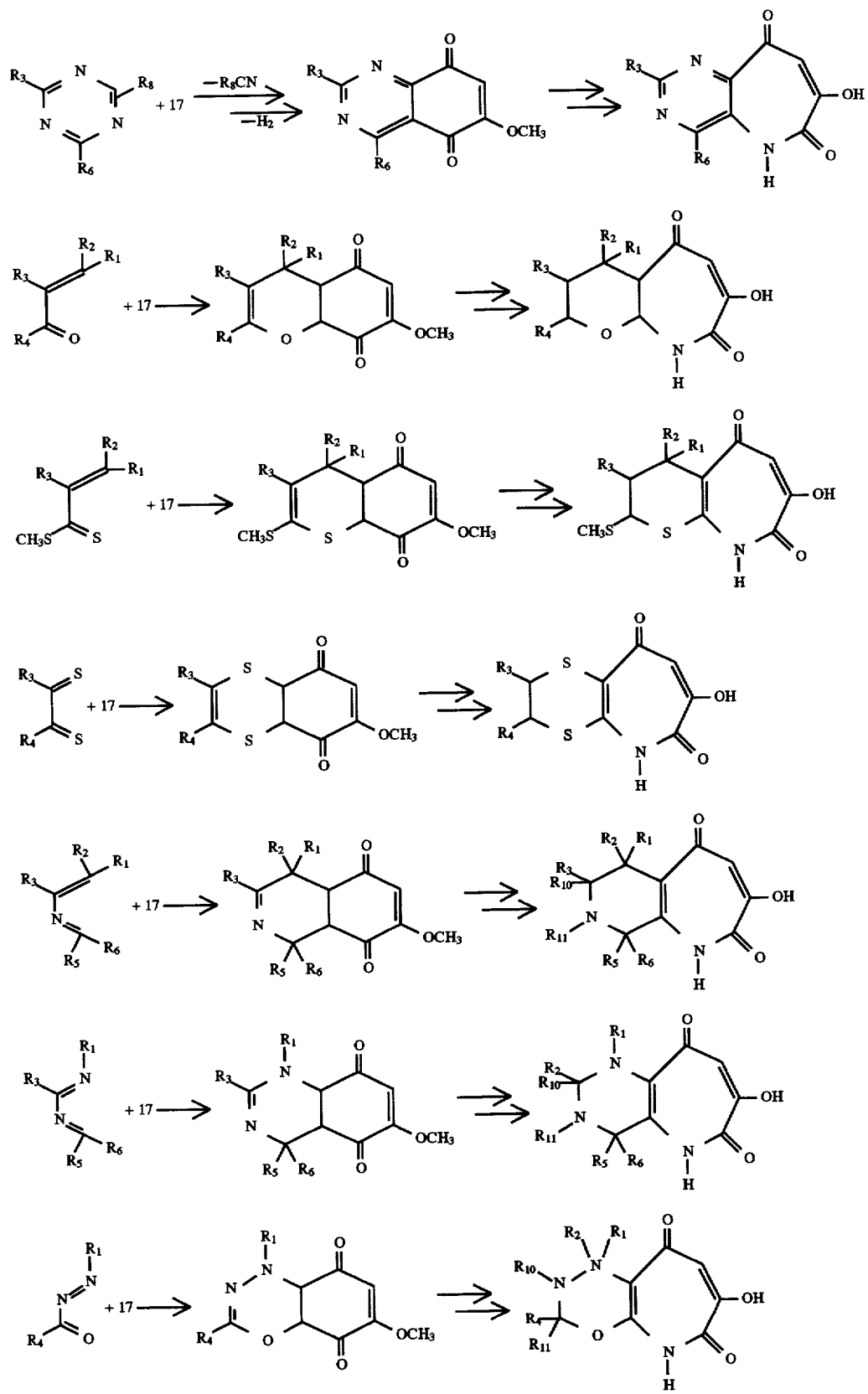

-continued
Scheme III

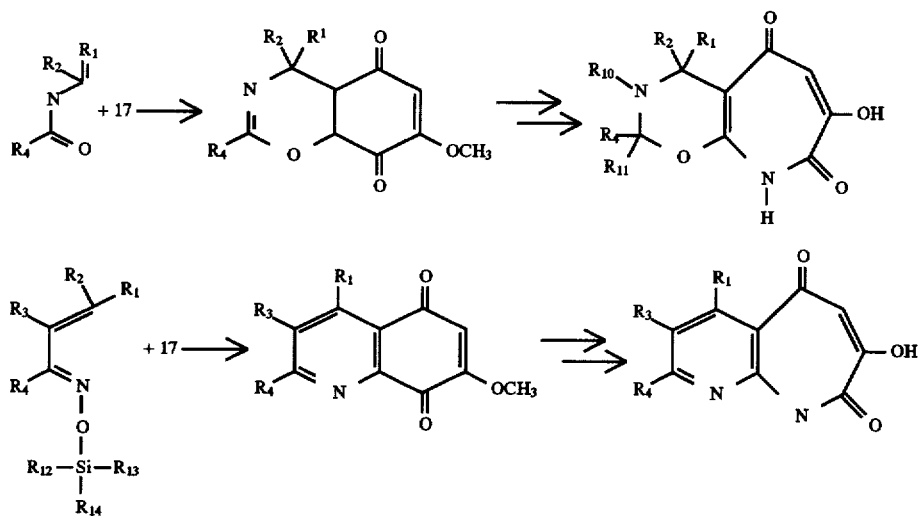

TABLE III

Examples of Investigative Diels-Alder Reactions Performed and 2-methoxynaphthalene-1,4-diones Prepared.

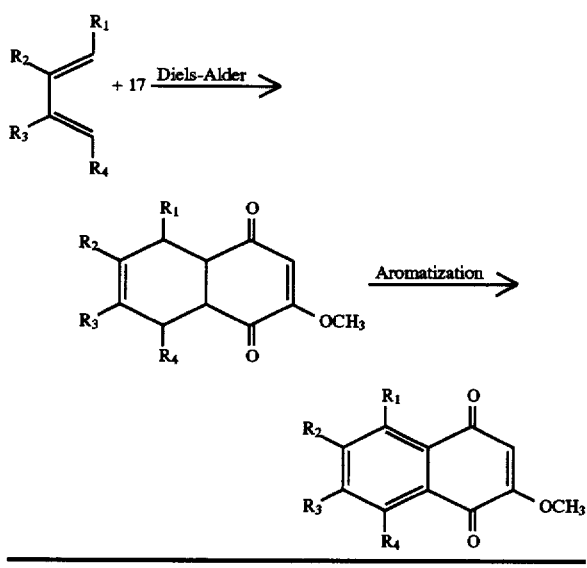

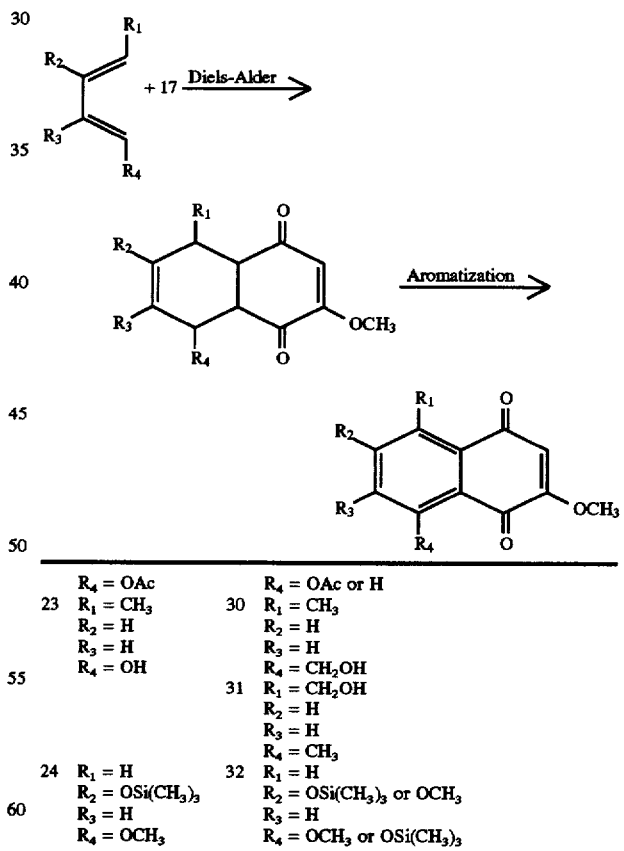

| | | | | | | |
|---|---|---|---|---|---|---|
| 18 | $R_1$ = H | 25 | $R_1$ = H | 33 | $R_1$ = H | |
| | $R_2$ = H | | $R_2$ = H | | $R_2$ = H | |
| | $R_3$ = H | | $R_3$ = H | | $R_3$ = H | |
| | $R_4$ = $CH_3$ | | $R_4$ = $CH_3$ | | $R_4$ = $CH_3$ | |
| 19 | $R_1$ = H | 26 | $R_1$ = H | 34 | $R_1$ = H | |
| | $R_2$ = $CH_3$ | | $R_2$ = $CH_3$ | | $R_2$ = $CH_3$ | |
| | $R_3$ = H | | $R_3$ = H | | $R_3$ = H | |
| | $R_4$ = $CH_3$ | | $R_4$ = $CH_3$ | | $R_4$ = $CH_3$ | |
| 20 | $R_1$ = $CH_3$ | 27 | $R_1$ = $CH_3$ | 35 | $R_1$ = $CH_3$ | |
| | $R_2$ = H | | $R_2$ = H | | $R_2$ = H | |
| | $R_3$ = H | | $R_3$ = H | | $R_3$ = H | |
| | $R_4$ = $CH_3$ | | $R_4$ = $CH_3$ | | $R_4$ = $CH_3$ | |
| 21 | $R_1$ = H | 28 | $R_1$ = H | 36 | $R_1$ = H | |
| | $R_2$ = $CH_3$ | | $R_2$ = $CH_3$ | | $R_2$ = $CH_3$ | |
| | $R_3$ = $CH_3$ | | $R_3$ = $CH_3$ | | $R_3$ = $CH_3$ | |
| | $R_4$ = H | | $R_4$ = H | | $R_4$ = H | |
| 22 | $R_1$ = H | 29 | $R_1$ = H or OAc | | | |
| | $R_2$ = H | | $R_2$ = H | | | |
| | $R_3$ = H | | $R_3$ = H | | | |

TABLE III-continued

Examples of Investigative Diels-Alder Reactions Performed and 2-methoxynaphthalene-1,4-diones Prepared.

| | | | |
|---|---|---|---|
| | $R_4$ = OAc | | $R_4$ = OAc or H |
| 23 | $R_1$ = $CH_3$ | 30 | $R_1$ = $CH_3$ |
| | $R_2$ = H | | $R_2$ = H |
| | $R_3$ = H | | $R_3$ = H |
| | $R_4$ = OH | | $R_4$ = $CH_2OH$ |
| | | 31 | $R_1$ = $CH_2OH$ |
| | | | $R_2$ = H |
| | | | $R_3$ = H |
| | | | $R_4$ = $CH_3$ |
| 24 | $R_1$ = H | 32 | $R_1$ = H |
| | $R_2$ = $OSi(CH_3)_3$ | | $R_2$ = $OSi(CH_3)_3$ or $OCH_3$ |
| | $R_3$ = H | | $R_3$ = H |
| | $R_4$ = $OCH_3$ | | $R_4$ = $OCH_3$ or $OSi(CH_3)_3$ |

The first major advantage of the present invention is the ability to readily prepare novel 2-methoxynaphthalene-1,4-diones. For example, to our knowledge, compounds 34 and 35 are unreported in the literature. The second major advantage of the present invention is the time and labor saved in the preparation of these quinones. The needed precursor (17) may be easily prepared in two steps from inexpensive and readily available vanillin. In practice, a relatively large quantity of vanillin is oxidized to 2-methoxyhydroquinone (37) (Logan et al., Can. J. Chem. 33:82–96 (1955)), which may be stored until needed. When desired, 37 is conveniently oxidized to 17 by stirring for 1 hr in an aqueous solution of NaIO$_4$ at rt (Alder et al., Acta Chem. Scand. 13:505–519 (1959)). Compound 17 is then isolated in near quantitative yield by simple solvent extraction followed by evaporation. The resulting 17 has been found to be sufficiently pure for further reaction.

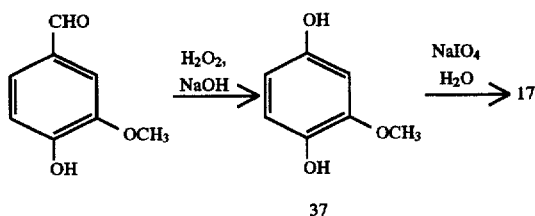

37

The quinone, e.g., crude 17 is heated overnight with excess diene in a solvent, such as toluene, in the presence of a polymerization inhibitor, such as hydroquinone, to yield the crude Diels-Alder adduct. In most cases thus far investigated, the crude adducts may be aromatized to 2-methoxynaphthalene-1,4-diones by stirring a MeOH solution of the adduct with Et$_3$N in the presence of O$_2$. An exception to this was found for the preparation of 35 (vide infra). Normally, the quinone may be readily purified by simple crystallization. The process from the oxidation of 37 to the collection of a purified 2-methoxynaphthlene-1,4-dione may be readily accomplished in a 48 h time period (2 working days). The yields for the three step process (oxidation of 37, Diels-Alder reaction, aromatization) is typically 20 to 35%.

The use of unsymmetrical dienes, such as 18, 19, 22, 23, and 24 have the potential of producing regioisomers during the Diels-Alder reaction. Indeed, the $^1$H NMR spectra of the crude adducts produced from these dienes showed product mixtures. Compounds 18 and 19 gave predominantly products whose structures are shown in Table III, i.e. 25 and 26. The minor isomers were removed during purification of the final quinone. The regiochemistry of 25 was established by literature precedent (Bohlmann et al., Chem. Ber. 110:2028–2045 (1977)) and by single crystal X-ray analysis of the subsequent 3-hydroxy-1H-1-benzazepine-2,4-dione (43, vide infra). The assignment of 26 was based on analogy with 25.

Dienes 22 and 24 gave predominantly one regioisomer as shown by $^1$H NMR. Diene 23 gave a near equal mixture of two regioisomers, 30 and 31, which were separated by chromatographic and crystallization techniques.

The preparation of quinone 35 was anomalous in that treatment of crude 27 with O$_2$ and Et$_3$N and MeOH unexpectedly gave quinone 38 as the isolated reaction product. Apparently, having methyl groups in both positions 5 and 8 prevents the aromatization of compound 38 under these conditions. Treating the isolated 38 under these same conditions yielded no reaction. Treatment of 38 with NaOMe and O$_2$ in MeOH led to decomposition.

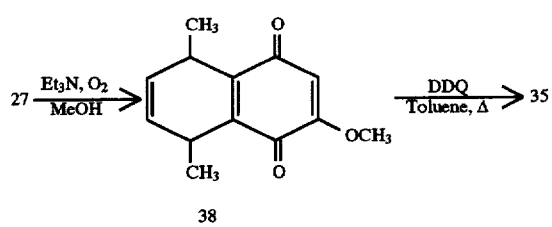

38

The reaction of 38 with DDQ (Fieser et al. Reagents for Organic Synthesis, 1, John Wiley & Sons, Inc., New York (1967), p. 215) (2.5 eq, freshly crystallized from benzene) in refluxing toluene gave the desired aromatic species 35. The reaction could be monitored by TLC analysis with 35 having a slightly lower R$_f$ than that of 38. An 87% mass recovery was obtained from the reaction after workup. The final yield of this reaction after purification (chromatography followed by crystallization) was about 50%.

The base promoted aromatization reaction apparently proceeds in a stepwise manner with at least 2 and possibly 3 distinct intermediates being observed by TLC analysis during the course of these reactions. The isolation of compound 38 has established the general structure for one of these intermediates. Based on this knowledge, a chain of plausible intermediates for this aromatization reaction is shown below.

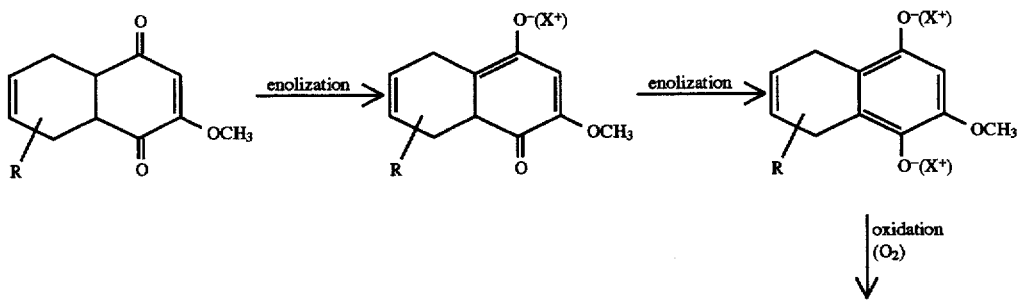

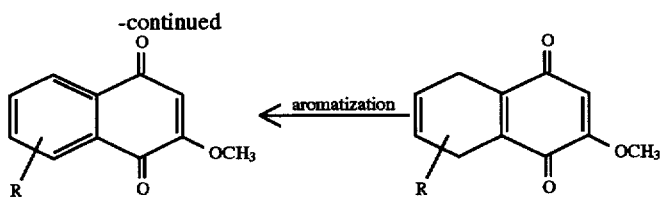

The use of disubstituted benzoquinones allows one to direct the regiochemical outcome of the Diels-Alder reaction. For example, the reaction of diene 18 with 2-bromo-5-methoxybenzoquinone yields one bromo adduct, which upon treatment with Et$_3$N, gives the dihydronaphthoquinone. Oxidation gives 2-methoxy-5-methylnaphthoquinone. On the other hand, the reaction of 18 with 17 followed by oxidation gives 2-methoxy-8-methylnaphthoquinone (33), i.e., the other possible regioisomer (vide supra).

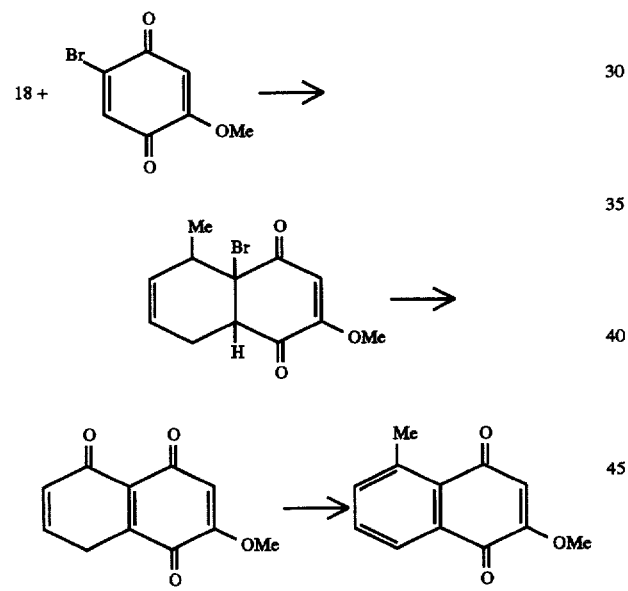

Quinones 33 to 36 were converted to the corresponding benzazepines (39 to 42) by treatment with NaN$_3$ in either neat CF$_3$SO$_3$H (33) or concentrated H$_2$SO$_4$ (34 to 36, Table IV). The yields were typically 40 to 60%. Demethylation of the methyl ethers 39, 40, 41, and 42 were accomplished with BBr$_3$ in CH$_2$Cl$_2$ to give enols 43, 44, 45 and 46. For example, 46 was obtained from 42 in the 77% yield. The structure of compound 43 was confirmed by single crystal X-ray analysis. Compounds 43 to 45 were inactive in the [$^3$H]-MK-801 competitive binding assay, while 46 demonstrated activity with an IC$_{50}$ of 7.3 μM. These data indicate that hydrogen may be the preferred substituent at position 9 of the benzazepine ring system.

TABLE IV

Substituted 3-hydroxy-1H-1-benzazepine-2,5-diones Prepared Via an Intermediate Diels-Alder Reaction

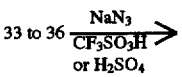

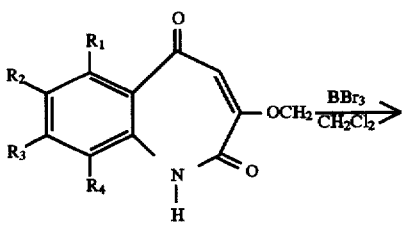

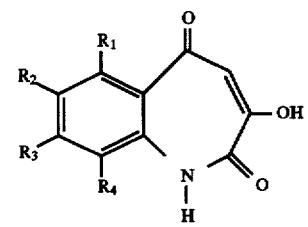

| 39 | R$_1$ = H | 43 | R$_1$ = H |
| | R$_2$ = H | | R$_2$ = H |
| | R$_3$ = H | | R$_3$ = H |
| | R$_4$ = CH$_3$ | | R$_4$ = CH$_3$ |
| 40 | R$_1$ = H | 44 | R$_1$ = H |
| | R$_2$ = CH$_3$ | | R$_2$ = CH$_3$ |
| | R$_3$ = H | | R$_3$ = H |
| | R$_4$ = CH$_3$ | | R$_4$ = CH$_3$ |
| 41 | R$_1$ = CH$_3$ | 45 | R$_1$ = CH$_3$ |
| | R$_2$ = H | | R$_2$ = H |
| | R$_3$ = H | | R$_3$ = H |
| | R$_4$ = CH$_3$ | | R$_4$ = CH$_3$ |
| 42 | R$_1$ = H | 46 | R$_1$ = H |
| | R$_2$ = CH$_3$ | | R$_2$ = CH$_3$ |
| | R$_3$ = CH$_3$ | | R$_3$ = CH$_3$ |
| | R$_4$ = H | | R$_4$ = H |

The Diels-Alder method may also allow for the preparation of bicyclic derivatives of 3-hydroxy-6,7,8,9-tetrahydro-1H-benzazepine-2,5-dione. The general procedure starts with a cyclic diene.

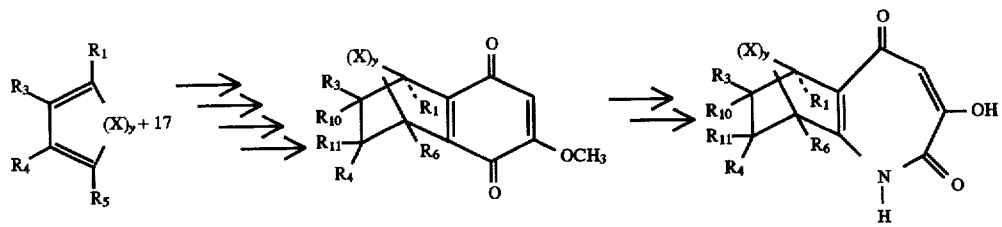

The groups $R_{10}$ and $R_{11}$ (e.g., hydrogen, halogen, hydroxy) are added to double bond formed by the Diels-Alder reaction.

Initial studies have begun utilizing the 1,4-methanonaphthalene-5,8-dione ring system obtained by the Diels-Alder reaction of 17 with cyclopentadiene, i.e. compound 47 (Scheme IV) (Okamata et al., *Chem. Pharm. Bull* 32:4593–4599 (1984)). Cyclopentadiene was allowed to react with quinone 17 in toluene at rt to give the adduct 47 in 64% yield after chromatographic purification. Compound 47 proved to be unstable in either neat $H_2SO_4$ or $CF_3SO_3H$ but was stable in glacial AcOH. In this medium, 47 is inert to $NaN_3$ at rt but gives a new product upon steam bath warming. However, this new product proved to be merely the result of the enolization of 47, i.e. the hydroquinone 48. Compound 48 is more conveniently prepared in 88% yield by treating 47 with $NaHCO_3$ in MeOH in the absence of $O_2$ followed by acidification. Periodate oxidation of 48 gave quinone 49 in 90% yield. Periodate oxidation of 48 in the presence of $NaN_3$ and AcOH gave an azide addition product, either 50 or 51 in poor yield (<20%). This material decomposed violently when exposed to ice cold concd $H_2SO_4$. Catalytic hydrogenation of 48 gave a near quantitative yield of 52. During workup, a trace amount of 52 was air oxidized to 53. Deliberate oxidation of 52 with $NaIO_4$ gave 53 in 88% purified yield.

Scheme IV

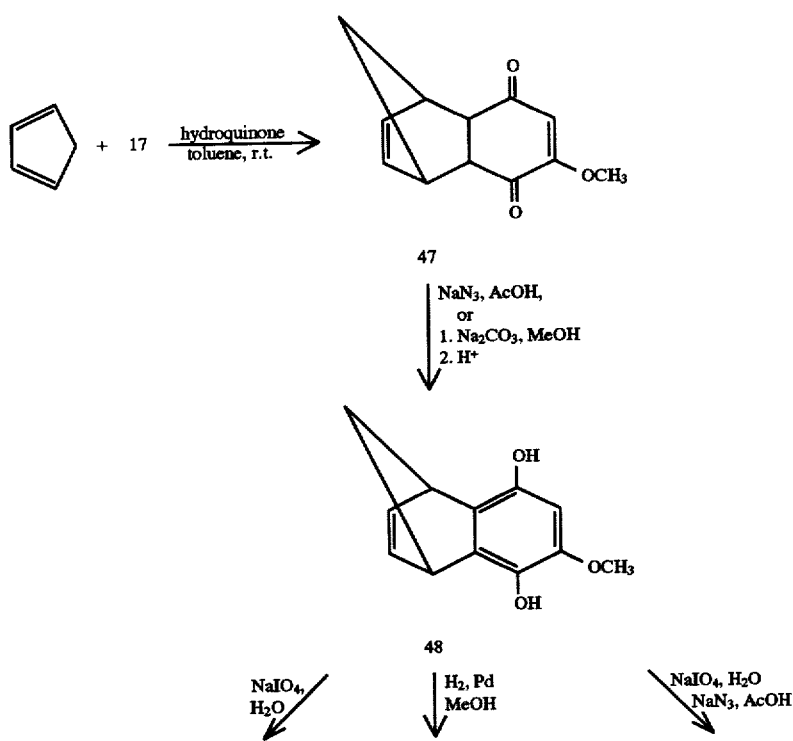

-continued
Scheme IV

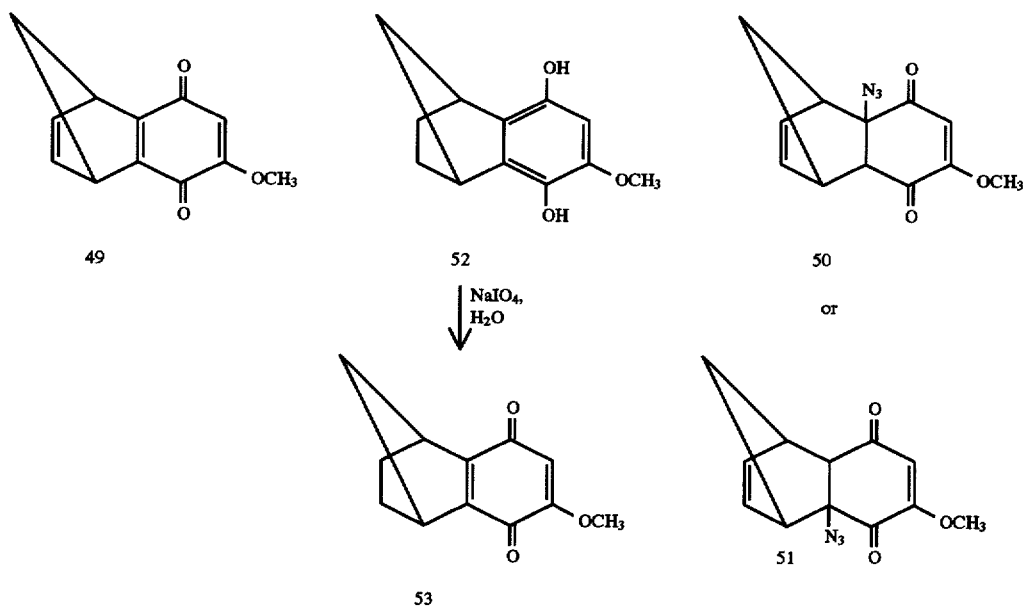

Compound 53 was convened to 6,9-methano-3-methoxy-6,7,8,9-tetrahydro-1H-1-benzazepine-2,5-dione by treatment with NaN$_3$ in cold, concentrated H$_2$SO$_4$. Removal of the methyl group with BBr$_3$ in methylene chloride gave 6,9-methano-3-hydroxy-6,7,8,9-tetrahydro-1H-1-benzazepine-2,5-dione.

The preparation of 3-hydroxy-6,7,8,9-tetrahydro-1H-1-benzazepine-2,5-dione has been accomplished according to the method outlined in Scheme V. The reaction of butadiene (54) with 2-methoxybenzoquinone (17) yielded the Diels-Alder adduct 55. Enolization with K$_2$CO$_3$/methanol followed by acidification gave the diol 56. Compounds 55 and 56 have been previously described (Cavill et al., Aust. J. Chem. 26:595–601 (1973)). Hydrogenation (H$_2$, Pd/C) of 56 gave a mixture of the expected reduced diol (57), its oxidation product (58, formed on exposure to air during workup) and the aromatization product (59). Compound 59 is postulated to be the result of a Pd catalyzed aromatization of 56, that occurred prior to the addition of H$_2$. Treatment of the crude mixture of 56, 57 and 58 with aqueous NaIO4 gave 58, with 59 as a minor contaminant.

The preparation of 58 has been previously reported. However, the methods employed are not general for the preparation of substituted derivatives. Hecher and Lattrell reported that 58 was obtained as part of a product mixture when 6-tetrol was treated with Tl(OAc)$_3$ in MeOH in the presence of BF$_3$.Et$_2$O (Hecher et al., Ann. 662:98–66 (1963)). Cunningham et al. reported the preparation of 58 in 5 steps from naphthalene-1,4-dione (Cunningham et al., J. Chem. Soc. 2875–2883 (1963)). This synthesis included a high pressure hydrogenation. These same authors reported that 58 may also be prepared by the methylation of 2-hydroxy-5,6,7,8-tetrahydronaphthalene-1,4-dione. However, the preparation of this enol requires several steps from naphthalene-1,4-dione including a high pressure hydrogenation (Skita et al., Ber. 63:1473–1484 (1930)). Finally, Tius et al. reported the preparation of 58, as well as the 7-tert-butyl and 9-methyl analogs, in 4 steps from 1-cyclohexanone-2-trimethylsilylvinyl ethers (Tius et al., J. Chem. Soc., Chem. Commun.: 867–869 (1989)).

Alberola et al. reported an octahydro-2-methoxyphenanthroquinone, which was obtained as a minor product from the direct hydrogenation of a Diels-Alder adduct obtained from the reaction of 17 with 1-vinyl-1-cyclohexene (Alberola et al., An. R. Soc. Esp. Fis. Quim., Ser. B, 62:691–698 (1966)). The process of the present invention enables one to prepare this same compound with significantly improved yield. In addition, the process of the present invention allows one to readily prepare various derivatives. Finally, it should also be noted that these types of phenanthroquinones have also been reported from the oxidation of pedocarpic acid derivatives (for example, see, Burkinshaw et al., Tetrahedron 23:4147–4152 (1967)).

The ring expansion of 2-methoxy-5,6,7,8-tetrahydronaphthalene-1,4-dione gives the corresponding 3-methoxy-6,7,8,9-tetrahydro-1H-benzazepine-2,5-dione. See, Hughes et al., who disclose that 2-methoxy-5-methylbenzene-1,4-dione undergoes ring expansion upon treatment with NaN$_3$ in concd H$_2$SO$_4$ (Hughes et al., Can. J. Chem. 52:3237–3330 (1974)).

Ring expansion (NaN$_3$, H$_2$SO$_4$) of 58 gave the desired tetrahydrobenzazepine enol ether (60) in poor yield (9%). Further investigation of this reaction should improve the yield. Treatment of 60 with BBr$_3$ in CH$_2$Cl$_2$ gave the desired enol (61) in 48% yield. The structure of compound 61 was confirmed by single crystal X-ray analysis. Compound 61 had an IC$_{50}$ of 34 μM in the [$^3$H]-MK-801 competitive binding assay.

The present invention also relates to the discovery of certain 3-hydroxy-6,7,8,9-tetrahydro-1H-1-benzazepine-1,4-diones have high affinity for the glycine/NMDA receptor and have unexpectedly high in vivo activity as anticonvulsants in the MES experiment in mice. Therefore, these compounds are able to cross the blood-brain-barrier at high levels. For instance, 3-hydroxy-6,7,8,9-tetrahydro-1H-1-benzazepine-1,4-dione (61), which has a K$_i$ of 1650 nM, was found to have an ED$_{50}$ of 8 mg/kg as an anticonvulsant in the MES experiment in mice. In comparison, another very active compound, 6,7-dichloro-5-nitro-1,4-dihydroquinoxaline-2,3-dione (K$_i$=3.3 nM), has an ED$_{50}$ of 4–5 mg/kg as an anticonvulsant in the MES experiment in mice. This means that 3-hydroxy-6,7,8,9-tetrahydro-1H-1-benzazepine-1,4-dione might be about 100 times better in crossing the blood-brain-barrier than 6,7-dichloro-5-nitro-1,4-dihydroquinoxaline-2,3-dione.

The conversion of 65 to 67 (Scheme VI) may be performed via 2 routes depending on the reducing or oxidizing nature of X'Y'. For example, if X'Y' is a reducing agent such as $H_2$, then 65 is first treated with X'Y' to give 66, which is then oxidized. On the other hand, if X'Y' is an oxidizing agent such as $Cl_2$, then 65 is initially oxidized and then X'Y' is added. This methodology has been used successfully to prepare 3-hydroxy-7,8-dichloro-6,7,8,9-tetrahydro-1H-1-benzazepine-2,5-dione (X'Y'=$Cl_2$), which had an $IC_{50}$ of 3.6 µM in the [$^3$H]-MK-801 competitive binding assay. Compounds such as 66, 67, 68 and 69 may be produced as a diastereomeric mixture. Such mixtures may be separated by routine chromatographic methods to give the pure diastereomers.

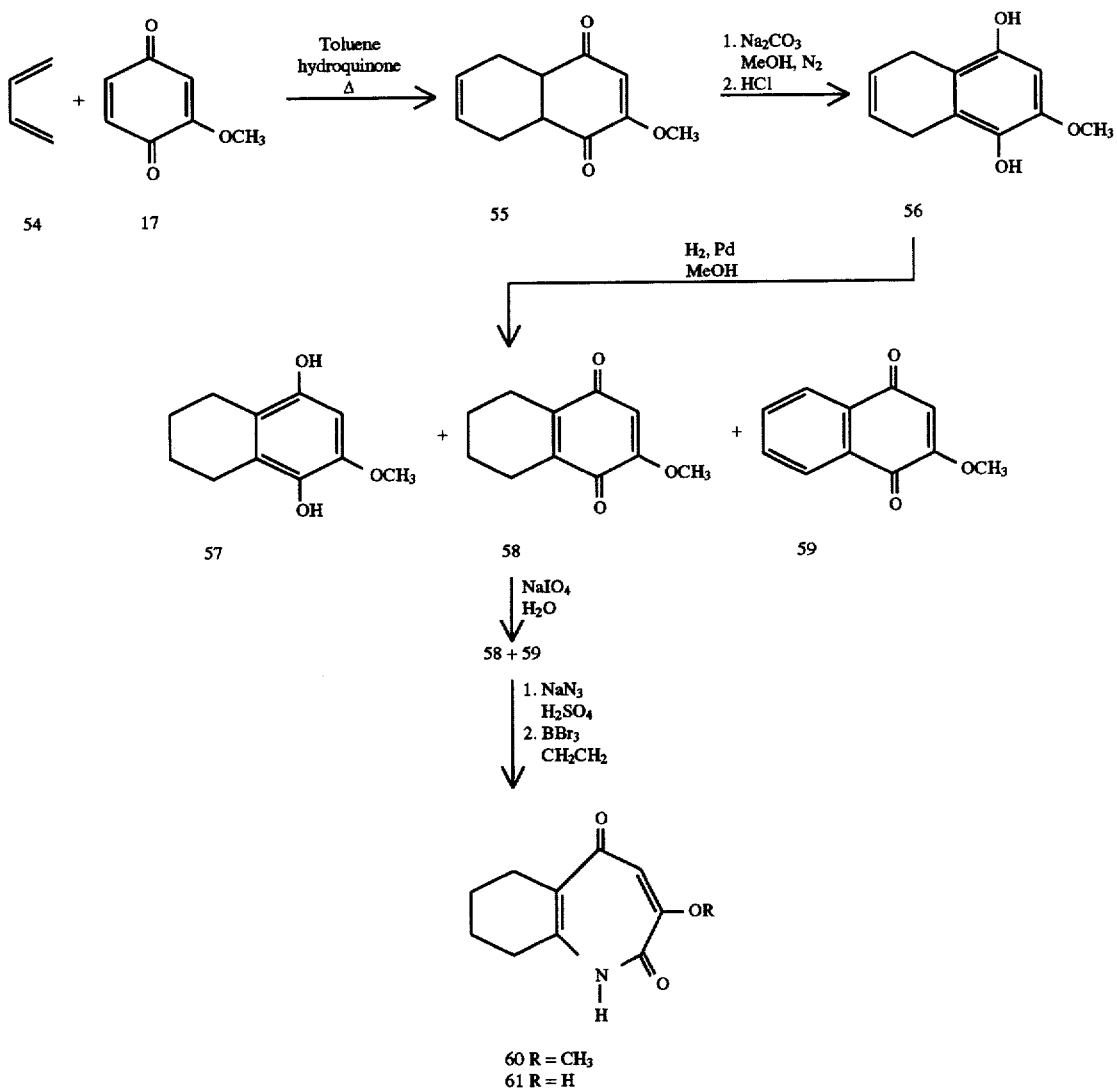

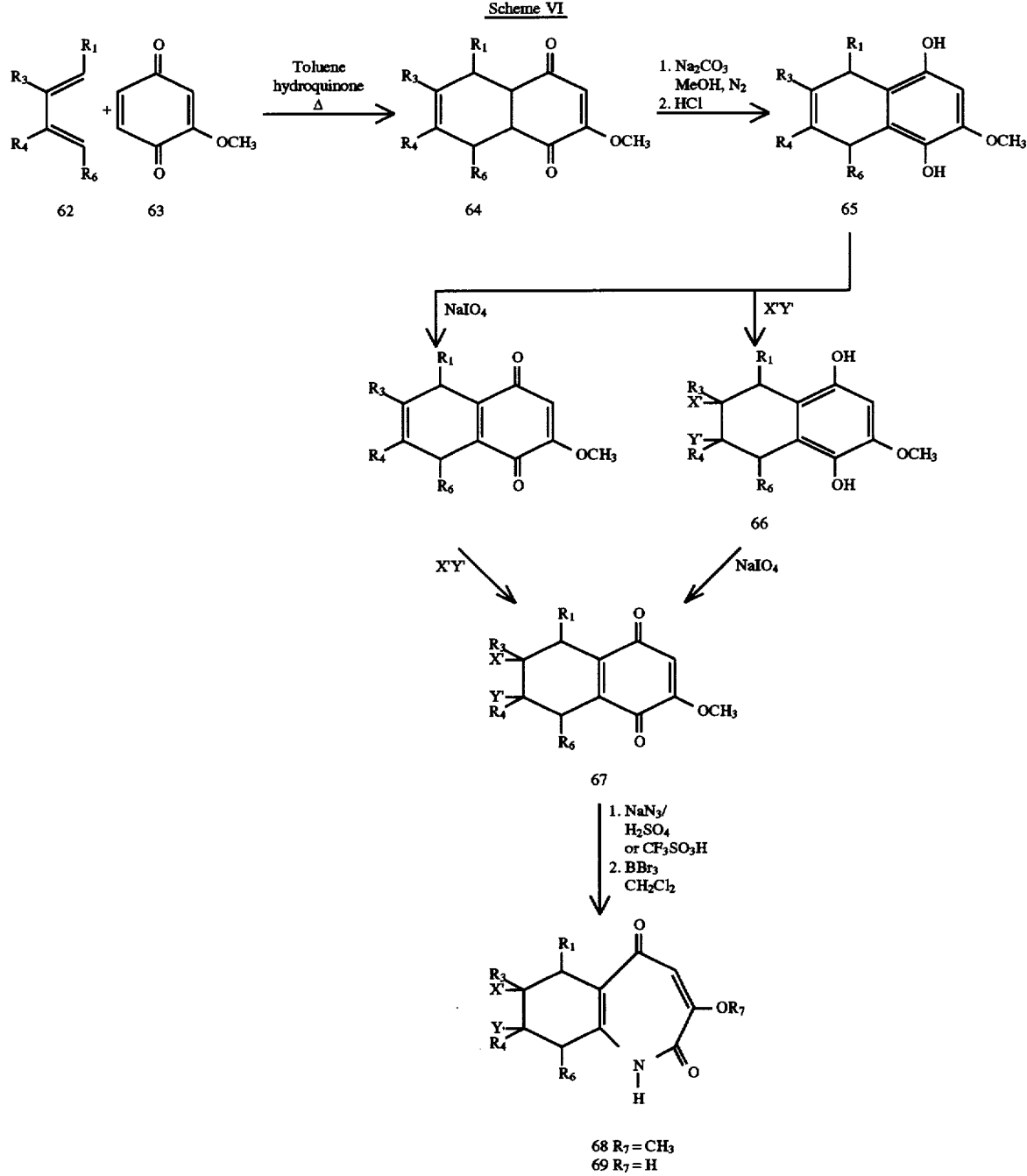

Scheme VI

68 R₇ = CH₃
69 R₇ = H

The literature does allow for the preparation of compound 67 where R₁=R₂=R₃=R₄=X'=Y'=H (i.e., compound 58 of Scheme V, Cunningham et al., *J. Chem. Soc.* 2875–2883 (1963); Skita et al., *Ber.* 63:1473–1484 (1930); Tius et al., *J. Chem. Soc., Chem. Commun.*: 867–869 (1989). However, the preparations described by Cunningham et al. and Skita et al. require a high pressure hydrogenation of the naphthalene ring system to yield a tetrahydronaphthalene. Such a process does not allow for the addition of other substituents, i.e. X'Y', to the parent naphthalene structure. Also, such a procedure does not allow substituents R₁ to R₆ to be labile under hydrogenation conditions. In addition, the preparation described by Tius et al. requires the use of substituted 1-cyclohexanone-2-trimethylsilylvinyl ethers, which restricts the generality of this method as any substituent present may not be labile to the requisite organolithium reagent used in the synthesis.

U.S. Pat. No. 5,254,683, International Application WO94/07500, and Swartz et al., *Molecular Pharmacol.* 41:1130–1141 (1992), have shown that 3-hydroxy-1H-benzazepine-2,4-diones with various substituents in the 7-position may be prepared. Such substituents which may be present include nitro, azido, acetamido, trifluoroacetamido, bromo, chloro and methyl. The nitro and bromo analogs were prepared by electrophilic nitration or bromination of 3-methoxy-1H-benzazepine-2,5-dione. The other nitrogen analogs were derived from the nitro compound. 8-Halo and 8-perfluoroalkyl derivatives of 3-hydroxy-1H-benzazepine-2,5-dione may also be prepared via multistep syntheses utilizing 7-halo or 7-perfluoroalkyl-1-tetralones. U.S. Pat. No. 5,254,683 reported the preparation of 8-halo derivatives using similar chemistry and the preparation of 6,8-dihalo derivatives starting from disubstituted bromobenzenes and a substituted cyclobutenone.

However, the preparation of 3-hydroxy-1H-benzazepine-2,5-dione with substituents other than halo or methyl in the 6- or 8-position has not been described. Attempts at such preparations have failed since the required oxidation of 7-nitro, 7-amino, 7-acetamido and 7-azido-1-tetralones to the corresponding 2-hydroxy-naphthalene-1,4-diones was not successful. Attempted oxidation reactions with a substituent in the 5-position also failed in our hands. This demonstrates the non-generality of this method. Thus, the Diels-Alder methodology offers the potential of preparing an abundance of uniquely substituted 3-hydroxy-1H-benzazepine-2,5-diones, e.g. those having groups other than halo or alkyl in the 6- and 8-positions.

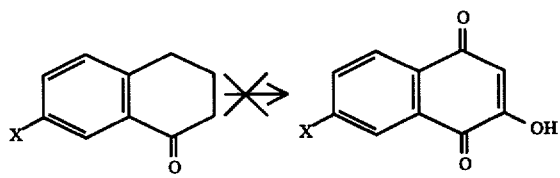

$X = NO_2, NH_2, AcNH, N_3$

Thus, the invention relates to a process for the preparation of a compound having the Formula I:

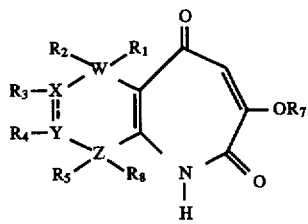

or a tautomer thereof;
wherein:
W is carbon, nitrogen, oxygen or sulfur;
X is carbon or nitrogen;
Y is carbon or nitrogen; and
Z is carbon, nitrogen, oxygen or sulfur;
the bond between X and Y is single;
$R_1$–$R_6$ are hydrogen, halo, haloalkyl, aryl, fused aryl, a heterocyclic group, a heteroaryl group, alkyl, alkenyl, alkynyl, arylalkyl, arylalkenyl, arylalkynyl, hydroxyalkyl, nitro, amino, cyano, acylamido, hydroxy, thiol, acyloxy, azido, alkoxy, carboxy, carbonylamido, alkylthiol, trialkylsilyloxy, phenyldialkylsilyloxy; or $R_1$ and $R_2$ or $R_5$ and $R_6$ are an unshared electron pair where W and Z, respectively, are oxygen or sulfur; or one of $R_1$ and $R_2$, or $R_3$, or $R_4$, or one of $R_1$ and $R_6$ is an unshared electron pair when W, X, Y or Z respectively is nitrogen; or where $R_1$ and $R_6$ together are a $C_{1-4}$ alkylene bridge, a substituted $C_{1-4}$ alkylene bridge, an oxygen bridge or an amino bridge; and $R_7$ is alkyl, alkanoyl, trialkylsilyl, phenyldialkylsilyl or tetrahydropyranyl;
with the proviso that X and Y are not other than carbon at the same time and that when one of W and Z is oxygen or nitrogen, then the other of W and Z is carbon;

by the Diels-Alder reaction of a compound having the Formula II:

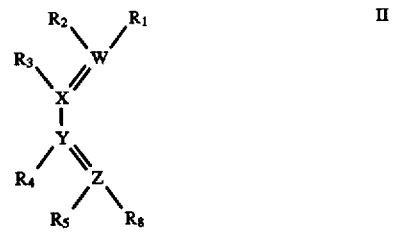

where $R_1$–$R_6$ are described above and wherein the diene may exist as a mixture of cis and trans isomers, with a quinone having the Formula III:

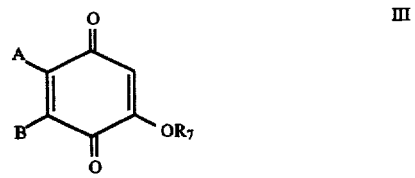

where A, B and $R_7$ are described above ($R_7 \neq H$);

to give a compound having the Formula IV:

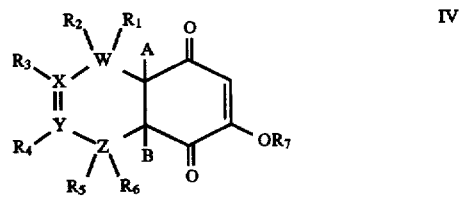

Examples of "dienes" which may be used in the practice of the invention include but are not limited to substituted and unsubstituted butadiene (W, X, Y and Z are carbon), substituted and unsubstituted oxazoles (W, Y and Z are carbon, X is nitrogen, and $R_1$ and $R_6$ are an oxygen bridge), substituted and unsubstituted triazines (W and Y are nitrogen, X and Z are carbon and $R_1$ and $R_6$ are a methanimino bridge), unsaturated carbonyl compounds (W, X and Y are carbon and Z is oxygen), unsaturated thioketones (W, X and Y are carbon and Z is sulfur), unsaturated imines (W, X and Y are carbon and Z is nitrogen substituted by a trialkylsiloxy or phenyldialkylsiloxy group), thiooxalic acid dithioesters (X and Y are carbon and W and Z are sulfur) and 1,2-dithiones.

"Dienes" where W and Z are sulfur may be prepared via photochemical ring opening of a disubstituted dithiaol-2-one as follows:

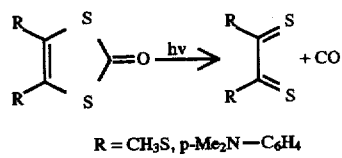

$R = CH_3S, p-Me_2N—C_6H_4$

See, for example, Kusters and De Mayo, *J. Amer. Chem. Soc.* 96:3502–11 (1974); Hartke et al., *Chem. Ber* 11(5): 1898–1906 (1980). Alternatively, hydrogen sulfide may be reacted with a 1,2-diimine:

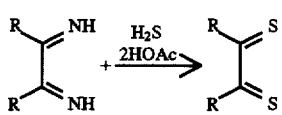

R=alkoxy (e.g., CH₃O, C₂H₅O, n-C₃H₇O, i-C₃H₇O, n-C₄H₉O, n-C₅H₁₁O). See, Hartke and Hoppe, *Chem. Ber.* 107:3121–9 (1974).

Examples of "dienophiles" having Formula III include 2-methoxybenzoquinone, 2-ethoxybenzoquinone, 2-butoxybenzoquinone, 2-pentoxybenzoquinone, 2-acetoxybenzoquinone, 2-butanoyloxybenzoquinone, 2-pentanoyloxybenzoquinone, 2-trimethylsilyloxybenzoquinone, 2-triethylsilyloxybenzoquinone, 2-tert.butyldimethylsilyloxybenzoquinone, and 2-tetrahydropyranyloxybenzoquinone, and the like. Compounds having Formula III may be prepared by oxidation of vanillin as described supra or by reaction of 2-hydroxybenzoquinone with an electrophile such as a dialkyl sulfate, an alkanoyl anhydride, a trialkylsilylchloride, or dihydropyran in an inert solvent containing a weak base such as pyridine.

In general, the Diels-Alder reaction may be carried out by heating a solution of the diene having Formula II with the "dienophile" quinone having Formula III to a temperature of about 25° to about 150° C. in a solvent such as toluene, dichlorobenzene, acetic acid and the like. A free-radical inhibitor such as hydroquinone may or may not be added to the solution to prevent the polymerization of the diene. The Diels-Alder reaction takes about 0.25 to about 120 hours. Afterward, the product may be isolated by removal of the solvent and the unreacted diene under vacuum.

The compound having Formula IV may then be enolized, hydrogenated to reduce the 6,7-double bond (with, for example Pd/C or Adam's catalyst) and then oxidized to the quinone with an oxidant such as molecular oxygen, DDQ, chloranil, MnO₂, NaIO₄, FeCl₃ and the like. The quinone may then be ring expanded with azide in acidic solution to give the compound having Formula I.

The invention also relates to a method for the preparation of a compound having Formula VI:

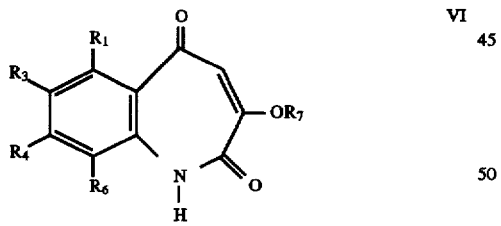

wherein $R_1$, $R_3$, $R_4$, $R_6$ and $R_7$ are described above ($R_7 \neq H$); by the Diels-Alder reaction of a diene having Formula VII:

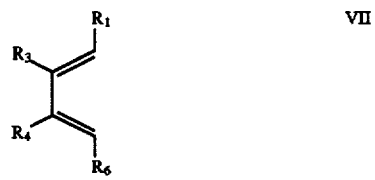

wherein $R_1$, $R_3$, $R_4$ and $R_6$ are defined above, and wherein $R_1$ and $R_6$ may additionally be an oxygen bridge, a sulfur bridge, an amino bridge (N—$R^9$, where $R^9$ is alkyl, aryl, acyl or carbalkoxy), a methanimine bridge or a substituted methanimine bridge, wherein such substituent is a halo, haloalkyl, aryl, fused aryl, a heterocyclic group, a heteroaryl group, alkyl, nitro, amino, cyano, acylamido, alkoxy, carboxy, carbonylamido or alkylthiol group;

and wherein the diene having Formula VII may exist as a mixture of cis and trans isomers;

with the quinone having Formula III (A and B=H in this example, but one of A and B may be other than hydrogen whereby the quinone is obtained directly), to give a compound having Formula VIII:

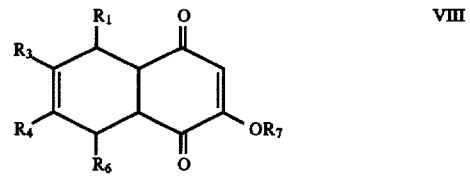

The compound having Formula VI may then be prepared by enolization and oxidation of the intermediate having Formula VIII to the corresponding naphthoquinone and reaction with azide in acidic solution to give the ring-expanded compound having Formula VI.

There are four possible sequences from cycloaddition product to quinone, as follows (note: not all R groups depicted):

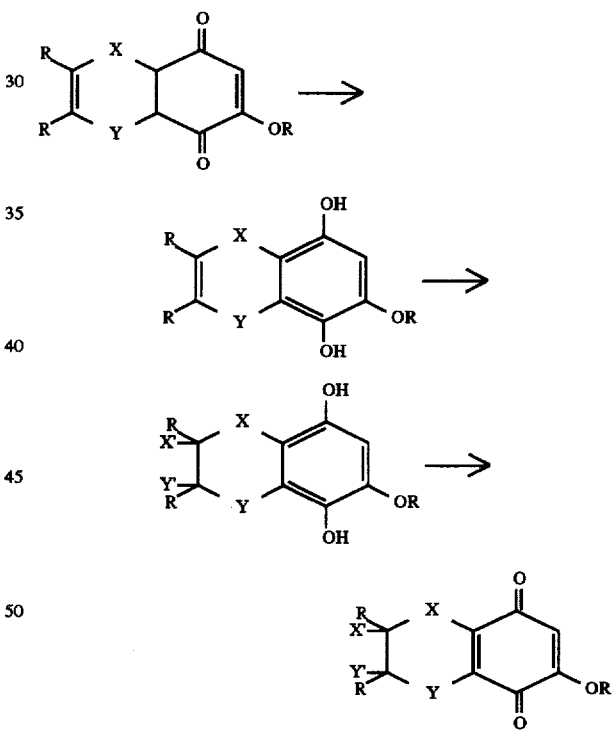

X and/or Y are C, N, O or S.

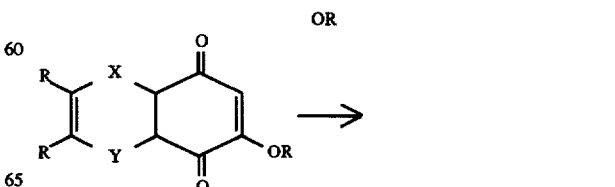

49
-continued

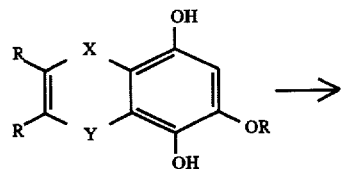

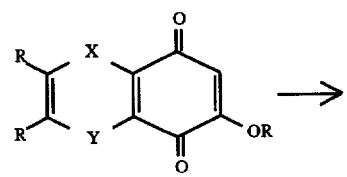

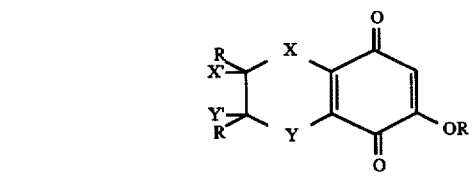

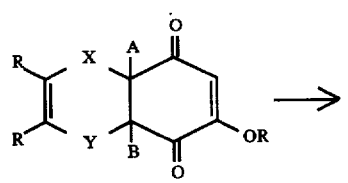

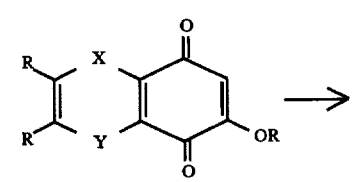

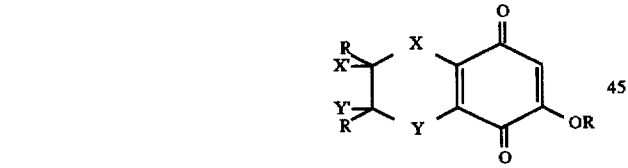

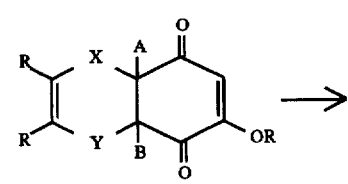

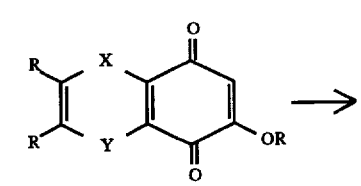

50
-continued

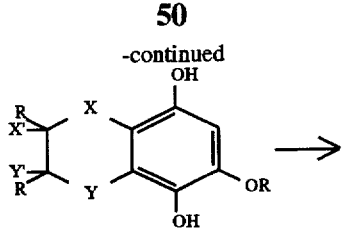

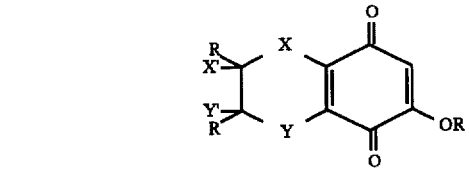

Alternatively, a compound having Formula IX

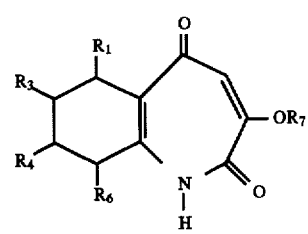

may be prepared by enolization of the intermediate VIII with a base, for example, triethylamine or potassium carbonate in the absence of oxygen, give a compound having Formula X:

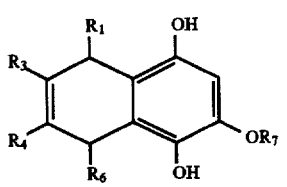

This compound may then be hydrogenated with for example $H_2$ and Pd/C or $H_2$ and Pt in ethanol, to give a compound having Formula XI:

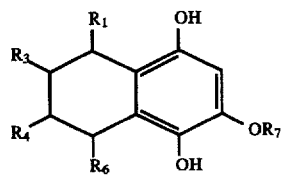

Alternatively, the double bond of the compound having Formula X may be halogenated to give a vicinyl dihalide, hydroborated to give a 6- or 7-hydroxy tetrahydronaphthohydroquinone, epoxidized to give the 6,7-oxirane, nitrated (with $N_2O_4$) to give the 6- or 7-nitro derivative, or oxidized (with $OsO_4$) to give the 6,7-dihydroxy derivative. The hydroxy compounds may be alkylated (with MeI, $Me_2SO_4$ or the like) or acylated with an alkanoyl anhydride, such as acetic anhydride\pyridine, to give esters. Alternatively, the 6,7-oxirane may be ring opened with an amino compound to give a vicinyl amino alcohol which may be acylated to give the vicinyl alkanoyloxy alkanoylamido derivative. This compound may then be oxidized to the quinone and then treated with azide in acidic solution to give the compound having Formula IX. The 6 or 7-nitro compound may be reduced (with Sn) to give the amine which may then be acylated, for example, with an alkanoyl anhydride in pyridine.

The invention also relates to a method for preparing an azepine having the formula:

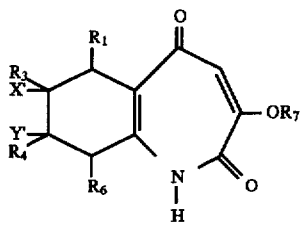

wherein $R_1$, $R_3$, $R_4$, $R_6$ and $R_7$ ($\neq$H) are defined above, and X' and Y' are independently halogen; hydroxy and hydrogen; nitro and hydrogen; alkanoylamido and hydrogen; X' and Y' together form an oxirane ring; or X' and Y' are vicinal alkanoylamido alkanoyloxy groups; comprising (a) the Diels-Alder reaction of the compound having Formula VII with the quinone having Formula III to give the compound having Formula VIII (b) enolization to the corresponding hydroquinone;

(c) halogenation; hydroboration/oxidation; nitration; nitration, reduction of the nitro group to an amine followed by acylation of the amine; epoxidation or epoxidation, ring opening with an amino compound, and acylation; respectively, to give a compound having the formula:

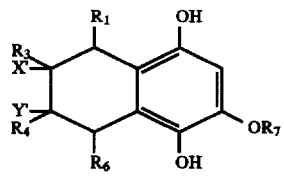

(d) oxidation to give the corresponding quinone; and (e) reaction with azide in acidic solution to give said azepine.

Where X' and Y' are chlorine, the double bond may be regenerated by reaction with Zn/ethanol.

The invention also relates to a method for preparing an azepine having the formula:

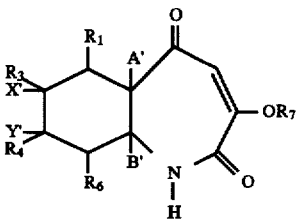

wherein $R_1$, $R_3$, $R_4$, $R_6$ and $R_7$ ($\neq$H) are defined above, X' and Y' are independently halogen; hydroxy and hydrogen; nitro and hydrogen; alkanoylamido and hydrogen; X' and Y' together form an oxirane ring; or X' and Y' are vicinal alkanoylamido alkanoyloxy groups; and where one of A' and B' is hydrogen and the other of A' and B' is alkyl or aralkyl, comprising (a) the Diels-Alder reaction of the compound having Formula VII with a quinone having the Formula:

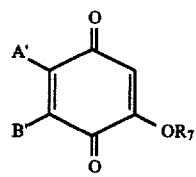

where A', B' and $R_7$ are defined above, to give a compound of the Formula:

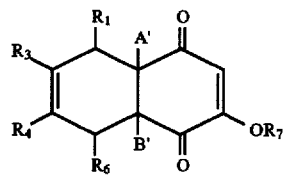

(b) halogenation; hydroboration/oxidation; nitration; nitration, reduction of the nitro group to an amine followed by acylation of the amine; epoxidation or epoxidation, ring opening with an amino compound, and acylation; respectively, to give a compound having formula:

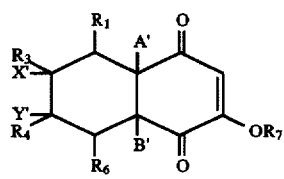

and (c) reaction with azide in acidic solution to give said azepine.

Where X' and Y' are chlorine, the double bond may be regenerated by reaction with Zn/ethanol.

The invention also relates to a method for the preparation of a compound having the Formula XII

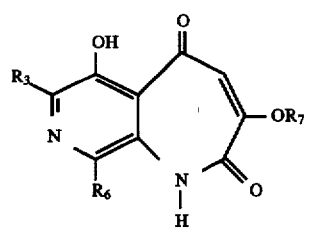

or its isomer having the Formula XIII:

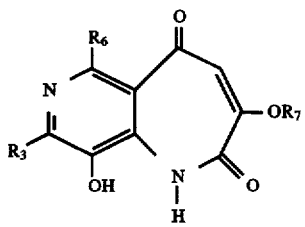

wherein $R_3$, $R_6$ and $R_7$ are defined above ($R_7 \neq$H); by the Diels-Alder reaction of the oxazole having Formula XIV:

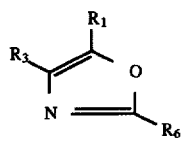  XIV wherein $R_3$ and $R_6$ are defined above and $R_1$ is alkoxy;

with the quinone having Formula III (A and B are hydrogen in this example), to give a compound having Formula XV:

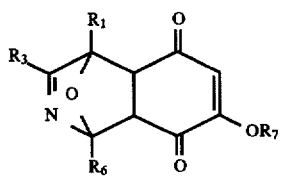  XV or its isomer having the Formula XVI:

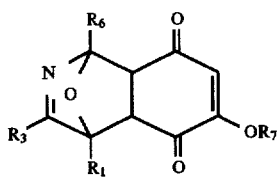  XVI

Examples of oxazoles having Formula XIV include oxazole, 2-methyloxazole, 2,4-dimethyloxazole, 2,4,5-trimethyloxazole, and 2,5-dimethyloxazole. See also, Beilstein's *Handbook of Organic Chemistry*, Compound Register for Volume 27, Springer-Verlag, Berlin (1986), pp. 823–830, for a list of other oxazoles which may be used. General methods for preparing oxazoles may be found, for example, in Boyd, G. V., *Comprehensive Heterocyclic Chemistry*, Potts, K. T., ed., Vol. 6, Pergamon Press, Oxford (1984), pp. 216–223, and Cornforth, J. W., *Heterocyclic Compounds*, Elderfield, R. C., ed., Vol. 5, John Wiley and Sons, New York (1957), pp. 298–323.

The spontaneous ring opening of the cyclic ether and elimination of $R_1H$ (an alcohol) gives a compound having Formula XVII:

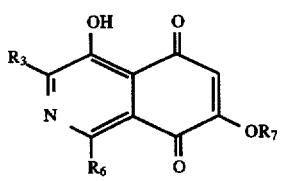  XVII or its isomer having Formula XIX:

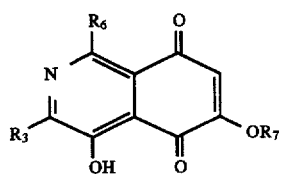  XIX and reaction with azide in acidic solution gives the compound having Formulas XII and/or XIII.

Alternatively, when one of A and B is other than hydrogen, the quinones having the following Formulae XVa and XVIa are obtained:

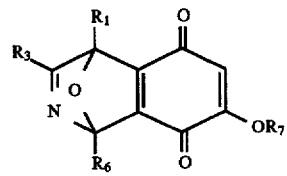  XVa

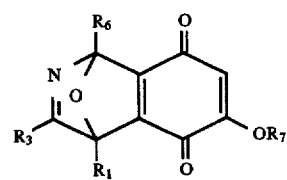  XVIa which may be reduced to give the 6,7-dihydro derivatives with sodium borohydride/EtOH and then treated with azide in acidic solution to give a compound having the formulas

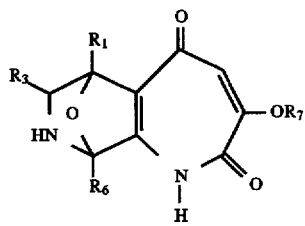

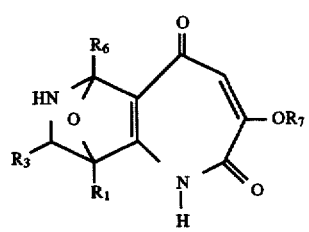

These compounds may be expected to be unstable in acidic solution. The stability may be improved by reducing XVa and XVIa with sodium borohydride, acylating the 6- or 7-amino group with an alkanoyl anydride $((R^1CO)_2O)$ in pyridine and then treated with azide in acidic solution to cause the ring expansion.

The quinones having Formulas XVa and XVIa may be ring opened with a reducing agent such as Zn/EtOH to give the compounds having formulas XVII and XIX:

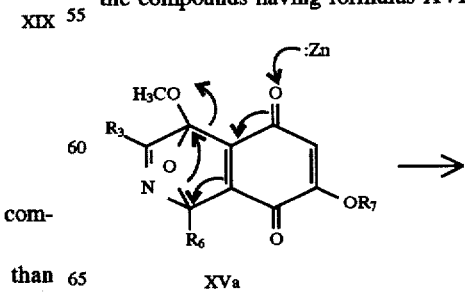

XVa

-continued

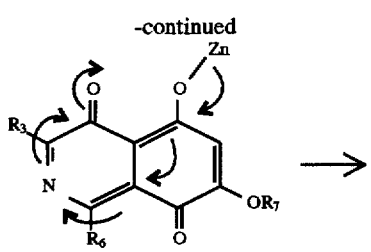

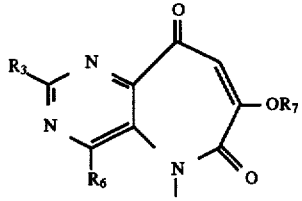

The invention also relates to a method for the preparation of a compound having Formula XX:

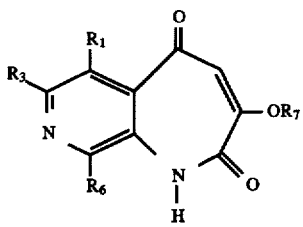

or its isomer having Formula XXI:

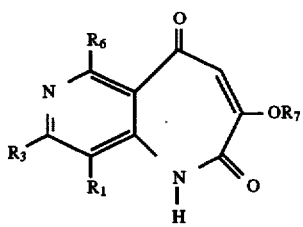

wherein $R_1$=H, and $R_3$, $R_6$ and $R_7$ are defined above, but wherein $R_1$ and $R_6$ are not a bridge and $R_7 \neq H$;

by the Diels Alder reaction of the compound having Formula XIV with the quinone having Formula III (A and B are hydrogen in this example) to give the intermediates having Formulas XV and XVI. Ring opening of the cyclic ether and elimination of water gives a compound having Formula XXII:

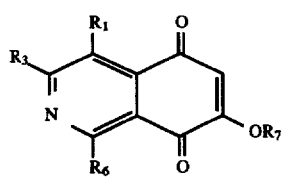

and its isomer having Formula XXIII:

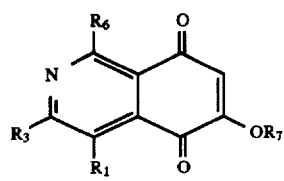

When one of A and B is other than hydrogen, the corresponding quinones are obtained directly which may be reduced (e.g. Zn/ethanol) and ring-opened to give XXII and XXIII.

Reaction of the compounds having Formulas XXII and XXIII with azide in acidic solution gives the compounds having Formulas XX and XXI, respectively.

The invention also relates to a method for the preparation of a compound having Formula XXIV:

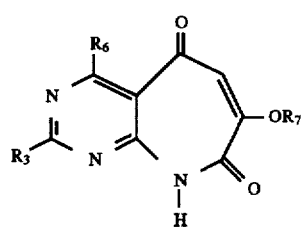

and its isomer having Formula XXV:

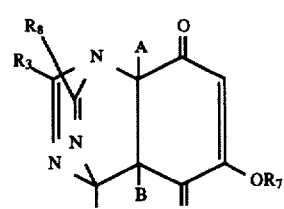

wherein $R_3$, $R_6$ and $R_7$ are defined above ($R_7 \neq H$); by the Diels-Alder reaction of a triazine having Formula XXVI:

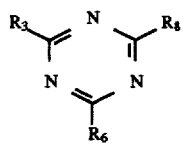

wherein $R_3$ and $R_6$ are defined above but $R_6$ may not be part of a bridge, and wherein $R_8$ is hydrogen, alkyl or aryl; with the quinone having Formula III to give the intermediate having Formula XXVII:

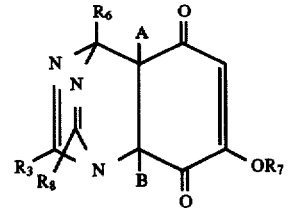

and its isomer having Formula XXVIII:

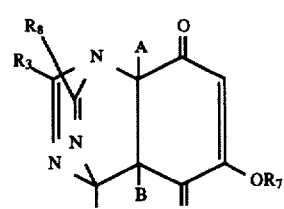

Examples of triazines having Formula XXVI include 2-methyltriazine, 2,4-dimethyltriazine, 2,3,6-trimethyltriazine, and those disclosed in Beilstein's *Handbook of Organic Chemistry*, Compound Register for Volume 26, Springer-Verlag, Berlin (1986), pp. 462–468.

General methods for preparing triazines may be found, for example, in Quirke, J. M. E., *Comprehensive Heterocyclic Chemistry*, Boulton and McKillop, eds., Vol. 3, Pergramon Press, Oxford (1984), pp. 490–523, and Modest, E. J., *Heterocyclic Compounds*, Elderfield, R. C., ed. Vol. 7, John Wiley and Sons, New York (1961), pp. 627–719.

Where one of A and B is other than hydrogen, the spontaneous elimination of $R_8$—CN and A-B (if necessary, in the presence of a base such as triethylamine) gives the intermediate having Formula XXIX:

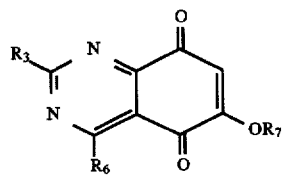

XXIX or its isomer having Formula XXX:

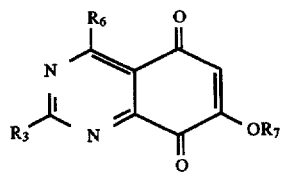

XXX

When A and B are hydrogen, the intermediates having Formulae XXVII and XXVIII must first be oxidized by either dehydrogenation (e.g., with DDQ), or enolized to the hydroquinone and oxidized to the quinone. Elimination of $R_8$—CN then gives XXIX and XXX.

Reaction of XXIX and XXX with azide in acidic solution gives the compounds having Formulas XXIV and XXV, respectively.

The invention also relates to a method for the preparation of a compound having Formula XXXI:

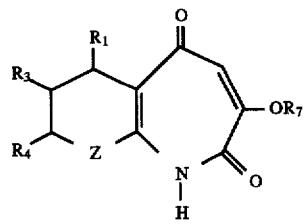

XXXI and its isomer having Formula XXXII:

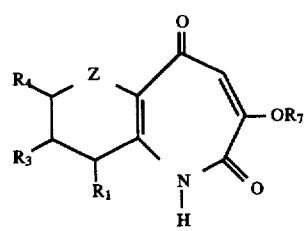

XXXII wherein $R_1$, $R_2$, $R_4$ and $R_7$ are defined above, but where $R_1$ is not part of a bridge and $R_7 \neq H$; and where Z is oxygen, sulfur or nitrogen substituted by a trialkylsiloxy or phenyldialkylsiloxy group;

by the Diels-Alder reaction of the diene having Formula XXXIII:

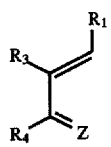

XXXIII with the quinone having Formula III (A and B are hydrogen in this example, but one of A and B may be other than hydrogen) to give a compound having Formula XXXIV:

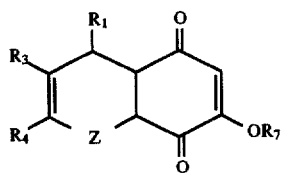

XXXIV or its isomer having Formula XXXV:

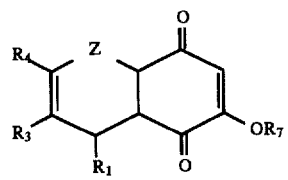

XXXV

Examples of compounds having Formula XXXIII include 3-buten-2-one, 3-methyl-3-buten-2-one, 2-butenal, 3-buten-2-thione, 3-methyl-3-buten-2-thione, 2-butenthial, 1-(tert-butyldimethylsilyloxy)-2-methyl-1-aza-1,3-butadiene, 1-(tert-butyldimethylsilyloxy)-1-aza-1,3-pentadiene, 3-penten-2-one, ethyl vinyl ketone, 3-methyl-3-buten-2-one, 4-methyl-5,5,5-trifluoro-3-penten-2-one, 4-ethoxy-1,1,1-trifluoro-3-butene-2-one, 4-hexen-3-one, mesityl oxide, 4-amino-3-methyl-3-penten-2-one, 5-methyl-3-hexen-2-one, 3-nonen-2-one, 5-ethyl-3-hepten-2-one, pseudoionone, acrolein, trichloroacrolein, crotonaldehyde, methacrolein, trans-2-methyl-2-butenal, ethylacrolein, trans-2-pentenal, 3-methyl-2-butenal, 3-(dimethylamino)acrolein, trans-2-hexenal, 2-methyl-2-pentenal, 3-methoxymethacrolein, 3-(dimethylamino)-2-methyl-2-propenal, trans-2-heptenal, 2-butylacrolein, trans-2-octenal, 2-ethyl-2-hexenal, 2,4-dimethyl-2,6-heptadienal and trans-2-nonenal. Each of these unsaturated carbonyl compounds may be converted to the corresponding silyloxyazabutadiene by the method of Behforouz et al., *J. Org. Chem.* 58:7089–7091 (1993), or to the thione by the use of Lawesson's Reagent (for a review on the use of Lawesson's Reagent see Cava and Levinson, *Tetrahedron* 41:5061 (1985)).

Enolization ($K_2CO_3$/methanol or ethanol) followed by hydrogenation (Pt or Pd/C in methanol, ethanol, methylene chloride or DMF) of the compounds having Formulas XXXIV and XXXV gives compounds having Formulas XXXVI and XXXVII:

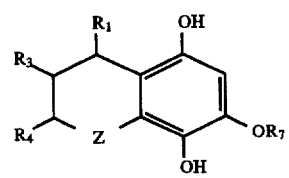

XXXVI

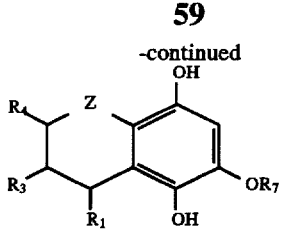

XXXVII

Oxidation to give the corresponding quinones and reaction with azide in acidic solution gives the compounds having Formulas XXXI and XXXII.

Where one of A and B is other than hydrogen, the quinone corresponding to XXXIV and XXXV is obtained which is hydrogenated to give the 5,6,7,8-tetrahydro-1,4-hydroquinone which may be oxidized to the quinone and reacted with azide in acidic solution to obtain XXXI and XXXII.

The invention also relates to the preparation of the heteroarylazepine having the Formula XXXIa:

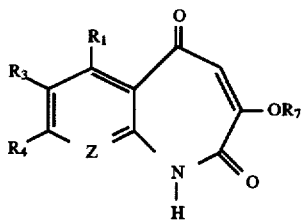

XXXIa and/or its isomer having Formula XXXIIa:

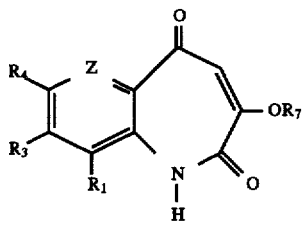

XXXIIa where Z is limited to nitrogen, by the oxidation of the intermediates having Formulae XXXIV and XXXV to the corresponding azanaphthalenequinones and reaction with azide. Alternatively, one of A and B may be other than hydrogen where the quinones corresponding to Formulae XXXIV and XXXV are obtained directly from the Diels-Alder reaction. Oxidation to the azanaphthalenequinone and reaction with azide gives XXXIa and XXXIIa.

The invention also relates to the corresponding aryl N-oxides of XXXIa and XXXIIa having the Formulae:

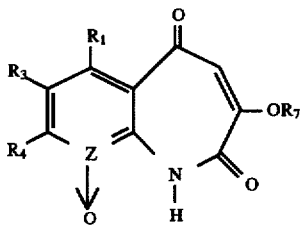

XXXIb

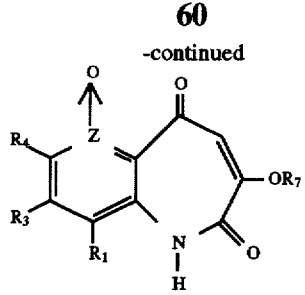

XXXIIb by N-oxidation of the compounds having Formulae XXXIa and XXXIIa.

The invention also relates to a method for the preparation of a compound having Formula XL:

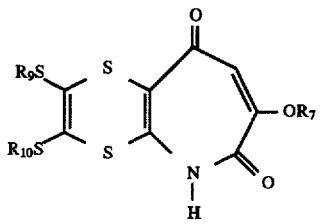

XL where $R_9$ and $R_{10}$ are independently alkyl and $R_7$ is defined above, by the Diels-Alder reaction of the compound having Formula XLI:

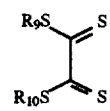

XLI with the quinone having Formula III (A and B=H in this example, but one of A and B may be other than hydrogen) to give a compound having Formula XLII:

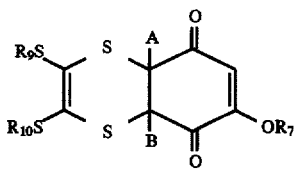

XLII wherein A and B are hydrogen.

Oxidation of XLII to the quinone and reaction with azide in acidic solution gives the compound having Formula XL.

The invention also relates to the preparation of N-oxides having the following Formulae:

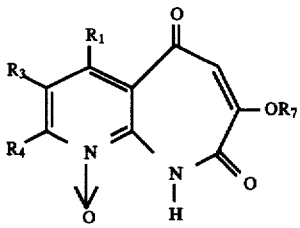

XLIII

XLIV

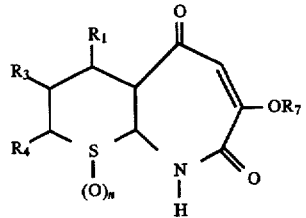

XLV

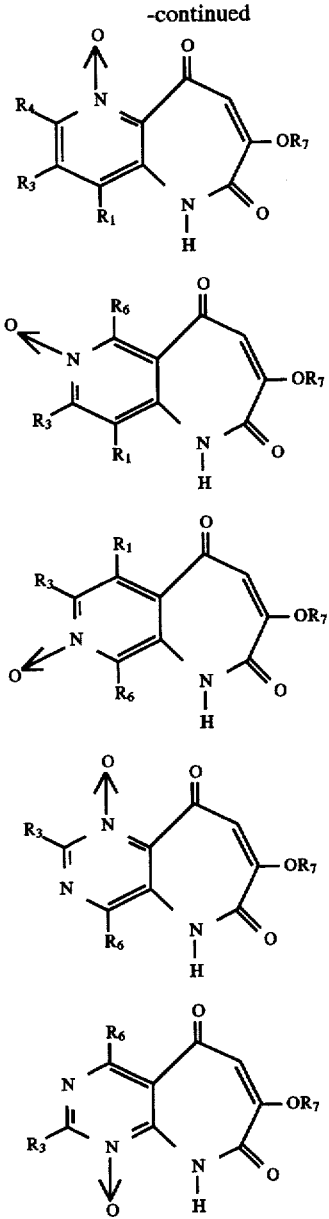

by the oxidation of the corresponding pyridines having Formulae XII, XIII, XVII, XIX, XX, XXI, XXXIa or XXXIIa, or the pyrimidine having Formulae XXIV or XXV, with, for example, the appropriate number of equivalents of $CF_3CO_3H$ or $m\text{-}ClC_6H_4CO_3H$ in an inert solvent such as methylene chloride.

The invention also relates to the sulfones and sulfoxides of the sulfur-containing compounds which have the Formulae:

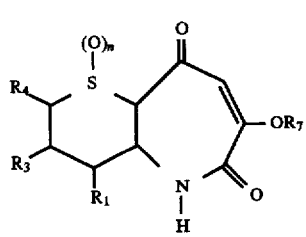

XLX

-continued
n = 1, 2 which can be prepared by oxidation of the corresponding thianes (n=0) with the calculated amount of $H_2O_2$ in glacial acetic acid or acetone or with an aqueous solution of sodium metaperiodate (one or two equivalents corresponding to n=1 or 2, respectively).

The invention also relates to the 3-amino analogs of the above-captioned azepines which may be prepared by reaction of the corresponding 3-methoxyazepine with a primary XLVI or secondary amine having the formula $NR_{12}R_{13}$ (see WO93/2553); wherein $R_{12}$ and $R_{13}$ are independently selected from hydrogen, alkyl, alkenyl, cycloalkyl, cycloalkylalkyl, aryl, arylalkyl, heteroaryl, heteroarylalkyl and $CH_2Y$ wherein Y is selected from $(CHOH)_nCH_2OH$ and $(CH_2)_mR^c$ where m is 0 to 5, n is 1 to 5 and $R^c$ is selected from hydroxy, alkoxy, alkoxycarbonyl, carboxy, cycloalkyl, and $NR^dR^e$ in which $R^d$ and $R^e$ are independently selected from hydrogen and alkyl or $R^d$ and $R^e$, together with the nitrogen atom to which XLVII they are attached, form a 5-, 6- or 7-membered heterocyclic ring which optionally contains one additional heteroatom selected from nitrogen, oxygen and sulfur; or $R_{12}$ and $R_{13}$ together with the nitrogen atom to which they are attached, form a 5-, 6- or 7-membered heterocyclic ring which is bonded to said compound through said nitrogen atom, said heterocyclic ring optionally containing one additional heteroatom selected from nitrogen, oxygen and sulfur.

Values of $R_{12}$ and $R_{13}$ of particular interest include, for example, hydrogen (1–6C)alkyl, (3–7C)cycloalkyl(1–6C) XLVIII alkyl, aryl, aryl(1–6C)alkyl, and heteroaryl(1–6C)alkyl, and $CH_2Y$ wherein Y is selected from $(CHOH)_nCH_2OH$ and $(CH_2)_mR^c$ wherein m is 0 to 5, n is 1 to 5 and $R^c$ is selected from hydroxy, (1–6C)alkoxycarbonyl and $NR^dR^e$ in which $R^d$ and $R^e$ are independently selected from (1–4C)alkyl, or $R_9$ and $R_{10}$, together with the nitrogen atom to which they are attached, form a 5-, 6- or 7-membered heterocyclic ring which is bound to said compound through said nitrogen atom, said heterocyclic ring optionally containing one additional heteroatom selected from nitrogen, oxygen and sulphur and wherein said heterocyclic ring may be substituted with 0–2 substituents selected from (1–6C)alkyl, phenyl, phenyl(1–4C)alkyl, phenoxy and phenyl(1–4C)alkoxy; and wherein an aryl or heteroaryl moiety may be substituted with 0–2 substituents selected from halo, cyano, hydroxy, carboxy, nitro, (1–6C)alkyl, (1–6C)alkoxy, (2–6C)alkenyl, phenyl, phenyl(1–4C)alkyl, phenoxy, phenyl(1–4C)alkoxy and (1–6C)alkoxycarbonyl.

It is generally preferred, for example, that when XLIX —$NR_{12}R_{13}$ represents a heterocyclic ring, said ring is selected from morpholino, imidazolyl, pyrrolidinyl, pyrrolo, pyrazolyl, piperindinyl [which may optionally bear a 4-substituent selected from (1–6C)alkyl, phenyl(1–6C) alkyl, phenoxy and phenyl], 4-morpholinyl, piperazinyl [which may optionally bear a 4-substituent selected from (1–6C)alkyl, phenyl(1–6C)alkyl and phenyl] and perhydroazepinyl.

Specific values for —$NR_{12}R_{13}$ include, for example, amino, methylamino, dimethylamino, diethylamino, phenethylamino, 4-morpholino, allylamino, α-methylbenzylamino, t-butoxycarbonylmethylamino, 1-perhydroazepinyl, 1-pyrrolidinyl, anilino, pyrrolo, 4-phenylpiperazin-1-yl, 4-benzylpiperazin-1-yl, piperidino, 4-(N,N-diethylamino)ethylamino, glucamino, 4-phenoxypiperidine, benzylamino, cyclopropylmethylamino, 3,4-dibenzyloxyphenethylamino, 2-(4-imidazolyl)ethylamino, N,N-bis(2-hydroxyethyl) amino, and N-(2-hydroxyethyl)amino.

The invention also relates to the 4-substituted azepines described herein, wherein the 4-substituent (T) is selected from hydrogen, halo, haloalkyl, hydroxy, alkanoyloxy, alkyl, aryl, a heterocyclic group, a heteroaryl group, nitro, amino, hydroxy, alkoxy or azido. Such groups may be introduced by treatment of the corresponding 3-alkoxy-2,5-dioxo-2,5-dihydroazepine with lithium diisopropylamide in tetrahydrofuran at −70° C., followed by reaction with an electrophile such as Cl$_2$, 1-bromobutane, benzylbromide, methyl iodide and methyl 4-bromomethylbenzoate. The 4-alkanoyloxy group may be introduced by displacement of a 4-chloride with the salt of the corresponding acid, e.g. acetate. Hydrolysis of the 4-alkanoyloxy group gives the 4-hydroxyazepine. Cleavage of the 3-alkoxy group with BBr$_3$ gives the 3-hydroxy-4-substituted 2,5-dioxo-2,5-dihydroazepine. Alternatively, the 4-substituents may be introduced by starting with an appropriately substituted quinone having Formula III.

In the examples given above, when R$_7$ is alkyl, the 3-alkoxy group may be cleaved with BBr$_3$ in dichloromethane or by mild acid hydrolysis to give the 3-hydroxyazepine. When R$_7$ is alkanoyl, the ester may be cleaved with aqueous acid. Where R$_7$ is trialkylsilyl or phenyldialkylsilyl, the silyl ether may be cleaved with aqueous tetrabutyl ammonium fluoride. Where R$_7$ is tetrahydropyranyl, the group may be cleaved with aqueous acid. Of course, one of ordinary skill in the art can employ other protecting groups (R$_7$) and remove them using no more than routine experimentation.

The present invention also relates to novel 2,5-dihydro-2,5-dioxo-1H-azepines which are highly selective, competitive antagonists of the glycine binding site of the NMDA receptor and of the excitatory amino acids.

Preferred compounds may be identified as follows:

(1) Placing a substituent (methyl) at position R$_6$ (i.e., position 9) of compounds of formula VI (see, compounds 43–45, Table IV) results in loss of activity. This is probably due to steric interference with the important N—H group in position 1. Therefore, preferred compounds of the invention should not have any substituent other than hydrogen in this position.

(2) Placing a lone substituent at position R$_3$ (i.e., position 7) of compounds of formula VI (see, compounds 11–15, Table II) results in greatly reduced to no activity. Therefore, preferred compounds should not be mono-substituted at R$_3$.

(3) Placing a substituent at R$_4$ (i.e., position 8) of compounds of formula VI (see, compounds 3, 5, 6, 7 (Table I) and 16) yields enhanced activity. Therefore, preferred compounds are mono-substituted at position R$_4$.

(4) Placing a substituent at R$_3$ and R$_4$ (i.e., positions 7 and 8) of compounds of formula VI (see, compound 46, Table IV) yields compounds of similar activity as the unsubstituted benzazepine. Therefore, these are not preferred compounds. On the other hand, placing substituents at R$_1$, R$_3$ and R$_4$ of compounds of Formula IX (see, dichloro compound described above) results in enhanced activity. Therefore, for compounds of Formula IX, substituents at R$_1$, R$_3$ and R$_4$ are preferred compounds.

(5) Preferred compounds have a hydrogen at R$_7$ (i.e., OH at position 3) or a pharmaceutically acceptable salt thereof. Also, substituents that may be readily cleaved to OH by intracellular enzymes, e.g. alkyl and alkanoyl groups such as acetate, are preferred.

It is expected that an extended lipophilic chain at position 7 (R$_3$) that has an initial linear (i.e., acetylenic, see below) portion will take advantage of a postulated distant lipophilic pocket in the receptor site. Such a lipophilic chain is expected to increase binding affinity and also the compound's ability to cross the blood-brain barrier.

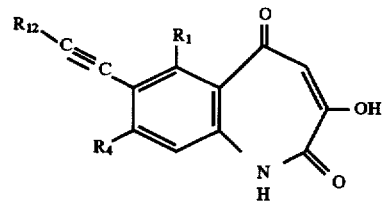

R$_{12}$ is an alkyl or arylalkyl group.

Also, a flexible chain extending from position 6 (R$_1$) (see below) is expected to have the same effect by binding with another postulated, distant lipophilic pocket.

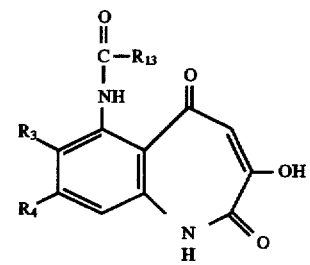

R$_{13}$ is an alkyl or arylalkyl group.

Compounds where R$_7$ is other than hydrogen are especially lipophilic and should more readily cross the blood-brain barrier. However, such compounds are not be expected, in themselves, to have high binding affinity to the glycine site. The binding affinity will be regained after the lipophilic R$_7$ group is cleaved intracellularly so that R$_7$ is again hydrogen. Thus, preferred compounds bear a substituent such as an alkanoyl group which is capable of being cleaved after crossing the blood-brain barrier or, more probably in a cell, to give a salt thereof. Thus, such compounds may serve as pro-drugs.

Typical C$_{6-14}$ aryl groups include phenyl, naphthyl, phenanthryl, anthracyl, indenyl, azulenyl, biphenyl, biphenylenyl and fluorenyl groups.

Typical fused aryl rings are benzo and naphtho groups fused to the 7,8-position of the azepine ring.

Typical halo groups include fluorine, chlorine, bromine and iodine.

Typical C$_{1-4}$ alkyl groups include methyl, ethyl, propyl, isopropyl, butyl, sec.-butyl, and tert.-butyl groups. Also contemplated is a trimethylene group substituted on the 7 and 8 positions of any one of the compounds of the invention.

Typical C$_{2-4}$ alkenyl groups include ethenyl, propenyl, isopropenyl, butenyl, and sec.-butenyl.

Typical C$_{2-4}$ alkynyl groups include ethynyl, propynyl, butynyl, and 2-butynyl groups.

Typical arylalkyl groups include any of the above-mentioned C$_{1-4}$ alkyl groups substituted by any of the above-mentioned C$_{6-14}$ aryl groups.

Typical arylalkenyl groups include any of the above-mentioned $C_{2-4}$ alkenyl groups substituted by any of the above-mentioned $C_{6-14}$ aryl groups.

Typical arylalkynyl groups include any of the above-mentioned $C_{2-4}$ alkynyl groups substituted by any of the above-mentioned $C_{6-14}$ aryl groups.

Typical haloalkyl groups include $C_{1-4}$ alkyl groups substituted by one or more fluorine, chlorine, bromine or iodine atoms, e.g. fluoromethyl, difluoromethyl, trifluoromethyl, pentafluoroethyl, 1,1-difluoroethyl and trichloromethyl groups.

Typical hydroxyalkyl groups include $C_{1-4}$ alkyl groups substituted by hydroxy, e.g. hydroxymethyl, hydroxyethyl, hydroxypropyl and hydroxybutyl groups.

Typical alkoxy groups include oxygen substituted by one of the $C_{1-4}$ alkyl groups mentioned above.

Typical alkylthio groups include sulphur substituted by one of the $C_{1-4}$ alkyl groups mentioned above.

Typical acyl (alkanoyl) groups are $C_{1-6}$, e.g., formyl, acetyl, propanoyl, butanoyl, pentanoyl, and hexanoyl groups.

Typical acylamino groups include any $C_{1-6}$ acyl (alkanoyl) substituted nitrogen, e.g. acetamido, propionamido, butanoylamido, pentanoylamido, hexanoylamido as well as aryl-substituted $C_{2-6}$ substituted acyl groups.

Typical acyloxy groups include any $C_{1-6}$ acyloxy groups, e.g. acetoxy, propionoyloxy, butanoyloxy, pentanoyloxy, hexanoyloxy and the like.

Typical heterocyclic groups include 3 to 10-membered cyclic radicals containing carbon and 1, 2, 3 or more O, N or S heteroatoms, including tetrahydrofuranyl, pyranyl, piperidinyl, piperizinyl, pyrrolidinyl, imidazolindinyl, imidazolinyl, indolinyl, isoindolinyl, quinuclidinyl, morpholinyl, isochromanyl, chromanyl, pyrazolidinyl and pyrazolinyl groups.

Typical heteroaryl groups include 5 to 14-membered cyclic unsaturated radicals containing carbon, 1, 2, 3 or more O, N or S heteroatoms, and 6, 10 or 14 delocalized electrons in one or more rings, including thienyl, benzo[b]thienyl, naphtho[2,3-b]thienyl, thianthrenyl, furyl, pyranyl, isobenzofuranyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups.

Typical amino groups include $-NH_2$, $-NHR^{15}$, and $-NR^{15}R^{16}$, wherein $R^{15}$ and $R^{16}$ are $C_{1-4}$ alkyl groups as defined above.

Typical carbonylamido groups are carbonyl groups substituted by $-NH_2$, $-NHR^{15}$, and $-NR^{15}R^{16}$ groups as defined above.

Typical $C_{3-18}$ trialkylsilyl groups include trimethylsilyl, triethylsilyl, tributylsilyl, tripentylsilyl, trihexylsilyl, tert.-butyldimethylsilyl and the like.

Typical $C_{8-18}$ phenyldialkylsilyl groups include phenyldimethylsilyl, phenyldiethylsilyl, phenyldipropylsilyl, phenyldibutylsilyl, phenyldipentylsilyl, phenyldihexylsilyl and the like.

Certain of the compounds of the present invention are expected to be potent anticonvulsants in animal models and will prevent ischemia-induced nerve cell death in the gerbil global ischemia model after i.p. or i.v. administration.

The compounds of the present invention are active in treating or preventing neuronal loss, neurodegenerative diseases, chronic pain, are active as anticonvulsants and inducing anesthesia. Certain of the compounds of the present invention are expected to exhibit little or no untoward side effects caused by non-selective binding with other receptors, particularly, the PCP and glutamate receptors associated with the NMDA receptor. In addition, certain of the compounds block kainate, AMPA (quisqualate) receptors and are therefore useful as broad-spectrum excitatory amino acid receptor antagonists. Moreover, the compounds of the present invention are effective in treating or preventing the adverse consequences of the hyperactivity of the excitatory amino acids, e.g. those which are involved in the NMDA receptor system, by blocking the glycine receptors and preventing the ligand-gated cation channels from opening and allowing excessive influx of $Ca^{++}$ into neurons, as occurs during ischemia.

Neurodegenerative diseases which may be treated with the compounds of the present invention include those selected from the group consisting of Alzheimer's disease, amyotrophic lateral sclerosis, Huntington's disease and Down's syndrome.

The compounds of the present invention find particular utility in the treatment or prevention of neuronal loss associated with multiple strokes which give rise to dementia. After a patient has been diagnosed as suffering from a stroke, the compounds of the present invention may be administered to ameliorate the immediate ischemia and prevent further neuronal damage that may occur from recurrent strokes.

Moreover, the compounds of the present invention are able to cross the blood/brain barrier which makes them particularly useful for treating or preventing conditions involving the central nervous system.

The compounds of the invention find particular utility in treating or preventing the adverse neurological consequences of surgery. For example, coronary bypass surgery requires the use of heart-lung machines which tend to introduce air bubbles into the circulatory system which may lodge in the brain. The presence of such air bubbles robs neuronal tissue of oxygen, resulting in anoxia and ischemia. Pre- or post-surgical administration of the compounds of the present invention will treat or prevent the resulting ischemia. In a preferred embodiment, the compounds of the invention are administered to patients undergoing cardiopulmonary bypass surgery or carotid endarterectomy surgery.

The compounds of the present invention also find utility in treating or preventing chronic pain. Such chronic pain may be the result of surgery, trauma, headache, arthritis, pain from terminal cancer or degenerative diseases. The compounds of the present invention also find particular utility in the treatment of phantom pain that results from amputation of an extremity. In addition to treatment of pain, the compounds of the invention are also expected to be useful in inducing anesthesia, either general or local anesthesia, for example, during surgery.

The novel glycine and excitatory amino acid antagonists may be tested for in vivo anticonvulsant activity after intraperitoneal injection using a number of anticonvulsant tests in mice (audiogenic seizure model in DBA-2 mice, pentylenetetrazol-induced seizures in mice, maximum electroshock seizure test (MES) or NMDA-induced death). The compounds may also be tested in drug discrimination tests in rats trained to discriminate PCP from saline. It is expected that most of the compounds of the present invention will not generalize to PCP at any dose. In addition, it is also expected that none of the compounds will produce a behavioral excitation in locomotor activity tests in the mouse. It is expected that such results will suggest that the novel glycine, AMPA, kainate and quisqualate antagonists of the present invention do not show the PCP-like behavioral side effects that are common to NMDA channel blockers such as MK-801 and PCP or to competitive NMDA antagonists such as CGS 19755.

The novel glycine and excitatory amino acid antagonists are also expected to show potent activity in vivo after intraperitoneal injection suggesting that these compounds can penetrate the blood/brain barrier.

It is well known to use opiates, e.g., morphine, in the medical field to alleviate pain. (As used herein, the term "opiates" is intended to mean any preparation or derivative of opium, especially the alkaloids naturally contained therein, of which there are about twenty, e.g., morphine, noscapine, codeine, papaverine, and thebaine, and their derivatives.) Unfortunately, with continued use, the body builds up a tolerance for the opiate, and, thus, for continued relief, the patient must be subjected to progressively larger doses. Tolerance develops after both acute and chronic morphine administration (Kornetsky et al., *Science* 162:1011–1012 (1968); Way et al., *J. Pharmacol. Exp Ther.* 167:1–8 (1969); Huidobro et al., *J. Pharmacol. Exp Ther.* 198:318–329 (1976); Lutfy et al., *J. Pharmacol. Exp Ther.* 256:575–580 (1991)). This, in itself, can be detrimental to the patient's health. Furthermore, a time can come when the tolerance is substantially complete and the pain killing properties of the drug are no longer effective. Additionally, administration of higher doses of morphine may lead to respiratory depression, causing the patient to stop breathing. Seeking alternative drugs to produce analgesia without development of tolerance or as an adjunct therapy to block tolerance without interference with analgesia is an active area of research.

Recent studies have suggested a modulatory role for the NMDA receptor in morphine tolerance. (Trujillo et al., *Science* 251:85–87 (1991); Marek et al., *Brain Res.* 547:77–81 (1991); Tiseo et al., *J. Pharmacol. Exp Ther.* 264:1090–1096 (1993); Lutfy et al., *Brain Res.* 616:83–88 (1993).) The present invention is also directed to the administration of the compounds described herein to inhibit opiate tolerance by blocking the glycine co-agonist site associated with the NMDA receptor.

The compounds of the present invention may be tested for potential glycine antagonist activity by observing the inhibition of binding of 1 µM glycine-stimulated [$^3$H]-MK-801 in rat or guinea pig brain membrane homogenates. The more potent the glycine antagonist, the less [$^3$H]-MK-801 can bind since the [$^3$H]-MK801 binding site (PCP receptor) is accessible only upon opening of the ion channel by glutamate and glycine (Fletcher, E. L., et al., in *Glycine Neurotransmission*, Otterson, P., et al. (eds.), John Wiley and Sons (1990); Johnson, J. W., et al., *Nature* 325:529 (1987)).

Thus, the present invention is directed to compounds having high binding to the glycine receptor and low binding to the kainate and AMPA sites. Particular compounds of the invention have high antagonist potency at the kainate, AMPA and quisqualate receptors in addition to the glycine receptor. According to the present invention, those compounds having high binding to the glycine receptor exhibit a glycine binding affinity ($K_i$) of about 10 µM or less in a glycine binding assay (see the Examples). Preferably, the compounds of the present invention exhibit a $K_i$ of 1 µM or less. Most preferably, the compounds of the present invention exhibit a $K_i$ of 0.1 µM or less. The compounds exhibit high binding to the kainate and AMPA sites if they exhibit a $K_i$ of about 10 µM or less, especially, 1 µM or less in a kainate or AMPA binding assay.

The glycine antagonist potency in vitro may be determined using a 1 µM glycine-stimulated [$^3$H]-MK801 binding assay. This assay takes advantage of the fact that the binding of [$^3$H]-MK801 to the PCP receptor inside the pore of the NMDA channel is dependent on the presence of both glutamate and glycine. In the absence of glycine but in the presence of glutamate, [$^3$H]-MK801 cannot bind effectively to the PCP receptor, because the NMDA channel remains closed and access of [$^3$H]-MK801 to the PCP receptor inside the closed channel pore is severely restricted.

The assay is conducted using rat brain membrane homogenates which are enriched in NMDA receptors. The membranes are prepared as follows. Frozen rat brains (obtained from Pel-Freez, Rogers, Ark.) are homogenized in 15 volumes (w/v) of ice cold 0.32M sucrose. The homogenate is spun at 1,000×g for ten minutes. The supernatant is collected and spun for 20 minutes at 44,000×g. The pellet is suspended in 15 volumes of water (relative to original brain weight. The homogenate is again spun at 44,000×g for twenty minutes. The pellet is resuspended in 5 volumes of water and the suspension is freeze-thawed 2 times. After the final thaw cycle, the suspension is brought to 15 volumes with water and spun at 44,000×g for twenty minutes. The pellet is resuspended in 5 volumes of ice-cold 10 mM HEPES, and is titrated to pH 7.4 with KOH containing 0.04% Triton X-100. Membranes are incubated with the Triton/HEPES buffer at 37° C. for 15 minutes. The volume is then brought to 15 with ice-cold 10 mM HEPES, pH 7.4, and spun/washed three times with spins of 44,000×g between washes. The final pellet is suspended in three volumes of 50 mM HEPES, pH 7.4 and the protein concentration is determined with a standard dye-binding protein assay (Bio-Rad, Richmond, Calif.). The suspension is stored at −80° C. until used. Only HPLC grade water is used for all buffers and suspensions/washings. The extensive washings are necessary to remove as much endogenous glycine from the membrane preparation as possible.

On the day of the assay, the previously prepared membranes are thawed and 5 mM Tris/HCl buffer, pH 7.4, is added to yield a final protein concentration of 0.156 mg/mL. For binding assays, 0.8 mL of membranes are pipetted into polypropylene tubes followed by 0.033 mL of 15.1 µM 5,7-dichorokynurenic acid (DCK), 0.033 mL of 30.3 µM glycine in buffer (or buffer alone), 0.033 mL of 303 µM glutamate in buffer (or for controls, 0.1 mL 1 mM PCP instead of DCK/gly/glu), 0.033 mL glycine antagonist in buffer (or buffer alone) and 0.1 mL buffer containing 200, 000 cpm [$^3$H]-MK801. Nonspecific binding is defined as the difference in binding that occurs in the absence or presence of PCP (final concentration: 100 µM). To determine the effect of 1 µM glycine on the binding of [$^3$H]-MK-801, bound radioactivity in the presence of 10 µM glutamate alone (final concentration) is subtracted from the bound radioactivity in the presence of both 10 µM glutamate and 1 µM glycine (final concentration). A 500 nM concentration (final) of 5,7-dichlorokynurenic (DCK) acid is added to all assay tubes. This concentration of the glycine antagonist DCK "buffers" most of the residual endogenous glycine that is not removed by the extensive washing steps that are carried out during the membrane preparation procedure. The 500 nM DCK does not interfere with the stimulation of [$^3$H]-MK-801 binding that is effected by the addition of 1 µM exogenous glycine.

The assays are incubated for 120 minutes at room temperature after which time the membrane-bound radioactivity is isolated from the free radioactivity by vacuum filtration through Whatman glass fiber filters that had been pretreated with 0.3% polyethyleneimine. Filtration is accomplished using a Brandel 48 well cell harvester. Filtered membranes are washed three times with 3 mL each of ice cold buffer. Filters are transferred to scintillation vials and 5 mL of scintillation cocktail is added. The vials are shaken overnight and the radioactivity is counted by liquid scintillation spectroscopy. The assays are done in triplicate and all experiments are conducted at least three times.

Inhibition dose response curves are constructed using increasing concentrations of glycine antagonists from 5 nM to 330 μM. $IC_{50}$ values are determined for compounds active in inhibiting 1 μM glycine-stimulated [$^3$H]-MK-801 binding by computer-assisted plotting of the inhibition curves and interpolation. When compounds are found to inhibit glycine-stimulated [$^3$H]-MK-801 binding, experiments are conducted to determine whether the inhibition of the glycine-stimulated [$^3$H]-MK-801 binding is indeed mediated at the glycine binding site of the NMDA receptor. In these experiments, a fixed concentration of antagonist sufficient to produce a >95% inhibition of the 1 μM glycine-stimulated [$^3$H]-MK-801 binding is incubated with the membranes without any additional glycine (above 1 μM) and in the presence of increasing concentrations of additional glycine (2 μM to 1 μM). If the inhibition of [$^3$H]-MK-801 binding by the drug in the presence of 1 μM glycine is fully reversed by adding increasing concentrations of glycine, then the inhibition of [$^3$H]-MK-801 binding is mediated by the drug acting as an antagonist at the glycine binding site of the NMDA receptor.

After constructing inhibition dose response curves and determination of glycine reversibility, $K_i$ values for the glycine antagonists are calculated using the Cheng and Prusoff equation employing the experimentally determined $IC_{50}$ values, the known concentration of glycine in the assay (1 μM) and the known affinity of glycine for the glycine binding site of the NMDA receptor (100 nM).

The same rat brain membrane homogenates used for the 1 μM glycine-stimulated [$^3$H]-MK-801 binding assay are used for the [$^3$H]-AMPA radioligand binding assay. On the day of the assay the frozen membranes (prepared as described above) are thawed and diluted with 30 mM Tris/HCl buffer containing 2.5 mM $CaCl_2$ and 100 mM KSCN, pH 7.4, to yield a final membrane concentration of 1.25 mg/mL membrane protein. For the binding assay, 0.8 mL of membrane homogenate is added to polypropylene tubes followed by 0.033 mL drug and 0.067 mL buffer (or for controls by 0.1 mL buffer alone) and 0.1 mL buffer containing 200,000 cpm of [$^3$H]-AMPA. The assay is incubated for 30 minutes on ice. Bound radioactivity is separated from free radioactivity by filtration over Whatman glass fiber filters (pretreated with 0.3% polyethyleneimine) using a Brandel 48 well cell harvester.

Filtered membranes are washed three times with 3 mL each of ice cold buffer. The filters are transferred to scintillation vials and 5 mL of scintillation cocktail is added. The vials are shaken overnight and radioactivity is counted by liquid scintillation spectroscopy. Nonspecific binding is determined by the radioactivity that remains bound to the membranes in the presence 10 mM glutamate. Inhibition dose response curves are constructed by adding increasing concentrations of drug from 10 nM to 100 μM.

The same membrane preparation as that used for the [$^3$H]-AMPA binding assay may be used for the [$^3$H]-Kainate radioligand binding assay. On the day of the assay the frozen rat brain membranes are thawed and 5 mM Tris/HCl buffer, pH 7.4, is added to yield a final concentration of 0.5 mg/mL membrane protein. For the binding assay, 0.8 mL of membrane homogenate is added to polypropylene tubes followed by 0.033 mL drug and 0.067 mL buffer (or for controls by 0.1 mL buffer alone) and 0.1 mL buffer containing 200,000 cpm of [$^3$H]-kainate. The assay is incubated for 2 hours on ice. Bound radioactivity is separated from free radioactivity by filtration over Whatman glass fiber filters (pretreated with 0.3% polyethyleneimine) using a Brandel 48 well cell harvester. Filtered membranes are washed three times with 3 mL each of ice cold buffer. The filters are transferred to scintillation vials and 5 mL of scintillation cocktail is added. The vials are shaken overnight and radioactivity is counted by liquid scintillation spectroscopy. Nonspecific binding is determined by the radioactivity that remains bound to the membranes in the presence 10 mM glutamate. Inhibition dose response curves are constructed by adding increasing concentrations of drug from 250 nM to 330 μM.

The anxiolytic activity of any particular compound of the present invention may be determined by use of any of the recognized animal models for anxiety. A preferred model is described by Jones, B. J. et al., Br. J. Pharmacol. 93:985-993 (1988). This model involves administering the compound in question to mice which have a high basal level of anxiety. The test is based on the finding that such mice find it aversive when taken from a dark home environment in a dark testing room and placed in an area which is painted white and brightly lit. The test box has two compartments, one white and brightly illuminated and one black and non-illuminated. The mouse has access to both compartments via an opening at floor level in the divider between the two compartments. The mice are placed in the center of the brightly illuminated area. After locating the opening to the dark area, the mice are free to pass back and forth between the two compartments. Control mice tend to spend a larger proportion of time in the dark compartment. When given an anxiolytic agent, the mice spend more time exploring the more novel brightly lit compartment and exhibit a delayed latency to move to the dark compartment. Moreover, the mice treated with the anxiolytic agent exhibit more behavior in the white compartment, as measured by exploratory rearings and line crossings. Since the mice can habituate to the test situation, naive mice should always be used in the test. Five parameters may be measured: the latency to entry into the dark compartment, the time spent in each area, the number of transitions between compartments, the number of lines crossed in each compartment, and the number of rears in each compartment. The administration of the compounds of the present invention is expected to result in the mice spending more time in the larger, brightly lit area of the test chamber.

In the light/dark exploration model, the anxiolytic activity of a putative agent can be identified by the increase of the numbers of line crossings and rears in the light compartment at the expense of the numbers of line crossings and rears in the dark compartment, in comparison with control mice.

A second preferred animal model is the rat social interaction test described by Jones, B. J. et al, supra, wherein the time that two mice spend in social interaction is quantified. The anxiolytic activity of a putative agent can be identified by the increase in the time that pairs of male rats spend in active social interaction (90% of the behaviors are investigatory in nature). Both the familiarity and the light level of the test arena may be manipulated. Undrugged rats show the highest level of social interaction when the test arena is familiar and is lit by low light. Social interaction declines if the arena is unfamiliar to the rats or is lit by bright light.

Anxiolytic agents prevent this decline. The overall level of motor activity may also be measured to allow detection of drug effects specific to social behaviors.

The efficacy of the glycine and excitatory amino acid antagonists to inhibit glutamate neurotoxicity in rat brain cortex neuron cell culture system may be determined as follows. An excitotoxicity model modified after that developed by Choi (Choi, D. W., *J. Neuroscience* 7:357 (1987)) may be used to test anti-excitotoxic efficacy of the novel glycine and excitatory amino acid antagonists. Fetuses from rat embryonic day 19 are removed from time-mated pregnant rats. The brains are removed from the fetuses and the cerebral cortex is dissected. Cells from the dissected cortex are dissociated by a combination of mechanical agitation and enzymatic digestion according to the method of Landon and Robbins (*Methods in Enzymology* 124:412 (1986)). The dissociated cells are passed through a 80 micron nitex screen and the viability of the cells are assessed by Trypan Blue. The cells are plated on poly-D-lysine coated plates and incubated at 37° C. in an atmosphere containing 91% $O_2$/9% $CO_2$. Six days later, fluoro-d-uracil is added for two days to suppress non-neural cell growth. At culture day 12, the primary neuron cultures are exposed to 100 µM glutamate for 5 minutes with or without increasing doses of glycine and excitatory amino acid antagonist or other drugs. After 5 minutes the cultures are washed and incubated for 24 hours at 37° C. Neuronal cell damage is quantitated by measuring lactate dehydrogenase (LDH) activity that is released into the culture medium. The LDH activity is measured according to the method of Decker et al. (Decker et al., *J. Immunol. Methods* 15:16 (1988)).

The anticonvulsant activity of the glycine and excitatory amino acid antagonists may be assessed in the audiogenic seizure model in DBA-2 mice as follows. DBA-2 mice may be obtained from Jackson Laboratories, Bar Harbor, Me. These mice at an age of <27 days develop a tonic seizure within 5-10 seconds and die when they are exposed to a sound of 14 kHz (sinus wave) at 110 dB (Lonsdale, D., *Dev. Pharmacol. Ther.* 4:28 (1982)). Seizure protection is defined when animals injected with drug 30 minutes prior to sound exposure do not develop a seizure and do not die during a 1 minute exposure to the sound. 21 day old DBA-2 mice are used for all experiments. Compounds are given intraperitoneally in either saline, DMSO or polyethyleneglycol-400. Appropriate solvent controls are included in each experiment. Dose response curves are constructed by giving increasing doses of drug from 1 mg/kg to 100 mg/kg. Each dose group (or solvent control) consists of at least six animals.

The anticonvulsant efficacy of the glycine receptor antagonists may be assessed in the pentylenetetrazol (PTZ)-induced seizure test as follows. Swiss/Webster mice, when injected with 50 mg/kg PTZ (i.p.) develop a minimal clonic seizure of approximately 5 seconds in length within 5-15 minutes after drug injection. Anticonvulsant efficacy of a glycine/excitatory amino acid antagonist (or other) drug is defined as the absence of a seizure when a drug is given 30 minutes prior to PTZ application and a seizure does not develop for up to 45 minutes following PTZ administration. Glycine/excitatory amino acid antagonist or other drugs are given intraperitoneally in either saline, DMSO or polyethyleneglycol-400. Appropriate solvent controls are included in each experiment. Dose response curves are constructed by giving increasing doses of drug from 1 mg/kg to 100 mg/kg. Each dose group (or solvent control) consists of at least six animals.

The efficacy of glycine/excitatory amino acid antagonists to protect mice from NMDA-induced death may be assessed as follows. When mice are injected with 200 mg/kg N-methyl-D-aspartate (NMDA) i.p., the animals will develop seizures followed by death within 5-10 minutes. Glycine/excitatory amino acid antagonists are tested for their ability to prevent NMDA-induced death by giving the drugs i.p. 30 minutes prior to the NMDA application. Glycine/excitatory amino acid antagonist or other drugs are given intraperitoneally in either saline, DMSO or polyethyleneglycol-400. Appropriate solvent controls are included in each experiment. Dose response curves are constructed by giving increasing doses of drug from 1 mg/kg to 100 mg/kg. Each dose group (or solvent control) consists of at least six animals.

The anticonvulsant activity of the glycine antagonists may be assessed in the maximum electroshock-induced seizure (MES) assay in mice. Electroshock is applied to male Swiss/Webster mice (20–30 g, Simonsen) through corneal electrodes (Swinyard, E. A., in *Anticonvulsant Drugs*, Mercier, J., ed., Pergamon Press, Oxford (1973), pp. 47–65). The seizure stimulus parameters are 50 mA, 60 Hz, rectangular pulse, width 0.8 msec, duration 200 msec. Tonic hind limb extension observed after application of the electrical stimulus is recorded as occurrence of seizure. The drug is applied i.v. as an aqueous, preferably basic solution.

The series of different evaluations may be conducted on doses of the glycine/excitatory amino acid antagonists of the invention to determine the biological activity of the compounds both in normal gerbils and in animals exposed to 5 minutes of bilateral carotid occlusion. See Scheme VII.

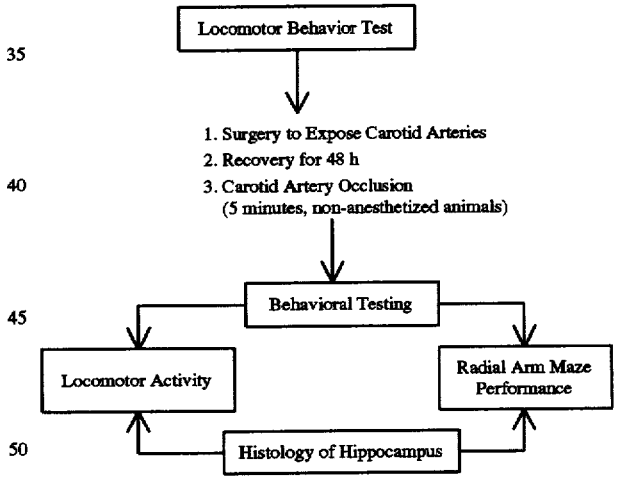

Scheme VII

Gerbil Ischemia Model

Locomotor Behavior Test

1. Surgery to Expose Carotid Arteries
2. Recovery for 48 h
3. Carotid Artery Occlusion
   (5 minutes, non-anesthetized animals)

Behavioral Testing
Locomotor Activity
Radial Arm Maze Performance
Histology of Hippocampus These studies are conducted in animals who are conscious and have no other pharmacological agents administered to them. Gerbils are preinstrumented 48-hours prior to ischemia to allow for the complete elimination of the pentobarbital anesthetic which is employed. When tested with drugs, animals are given IP injections of the glycine/excitatory amino acid antagonist or vehicle. In the case of multiple injections, animals are given IP injections 2 hours apart and the final injection is given 30 minutes prior to the ischemic period or in the case of post treatment, the animals are given injections at 30 minutes, 2 hours, 4 hours and 6 hours post-ischemic reperfusion.

In order to assess the direct pharmacological activity or potential activity of the glycine/excitatory amino acid antagonists, naive gerbils are injected with either saline or differing doses of the antagonist. The behavioral changes are assessed using a photobeam locomotor activity chamber which is a two foot circular diameter arena with photobeam detection. Animals are individually placed in the 2 foot diameter chambers. The chambers are housed in a cabinet which is closed and noise is abated using both a background white noise generator and a fan. Animals are placed in these chambers in the case of the initial pharmacological evaluation for a period of 6 hours and the total activity during each successive hour is accumulated using the computer control systems.

Saline results in an initial high rate of activity, with the control animals showing a first hour activity level of about 1600 counts. This level of control activity is typical for the gerbil under these experimental conditions. As the session progressed, animals decrease their exploratory activity and at the terminal period the activity declines to about 250 counts per hour. It is expected that the glycine/excitatory amino acid antagonists of the present invention will have no significant effect on either the initial exploratory rate or the terminal rate of exploration.

In a next phase of the evaluation of the glycine/excitatory amino acid antagonists, gerbils are pretreated with varying doses of the antagonists and then exposed to a five minute period of bilateral carotid occlusion. Following the initiation of reperfusion, animals are placed into the circular locomotor activity testing apparatus and the activity at the beginning of the first hour following reperfusion is monitored for the subsequent four hours.

Control animals not exposed to ischemia and given injections of saline prior to being placed in the locomotor activity chamber show a characteristic pattern of activity which in the first hour of locomotor activity is substantially higher than during all other hours and progressively declined over the four hours to a very low value. In contrast to the progressive decline in activity over the four hour testing period, control animals that are exposed to five minutes of cortical ischemia demonstrate a completely different pattern of locomotor activity. During the first hour there is a significant decline in activity which is followed by a progressive increase in which the activity during the fourth hour is ten-fold higher than that demonstrated by animals not exposed to carotid occlusion. These results are typical and are a reliable result of the alterations caused by five minutes of bilateral carotid occlusion in the gerbil.

Separate groups of gerbils are pretreated with the glycine/excitatory amino acid antagonists of the invention 30 minutes before the onset of carotid occlusion and then placed into the locomotor activity following one hour of reperfusion. It is expected that pretreatment of the gerbils with the glycine/excitatory amino acid antagonists of the invention will prevent both the post-ischemic decrease and increase in activity. Post-ischemic decreases in activity are expected to be near zero during the first hour following reperfusion. Pretreatment with the glycine/excitatory amino acid antagonists of the invention is expected to reduce or prevent this early depression of behavior. In addition, the glycine/excitatory amino acid antagonists of the invention are expected to prevent the post-ischemic stimulation of behavior.

Subsequent to completion of the single dose pretreatment evaluations, gerbils are also evaluated with multiple injections of the glycine/excitatory amino acid antagonists of the invention. Doses are administered I.P. at 6 hours, 4 hours, 2 hours and 30 minutes prior to the onset of 5 minutes of ischemia.

At 24 hours all animals are evaluated for differences in patrolling behavior using a 8-arm radial maze. In this procedure, animals are placed into the center start chamber of the maze, the barrier removed and the mount of time and the number of times the animal makes an error recorded prior to completion of exploration in all 8 arms of the maze. An error is defined as the revisiting of an arm by entering to the extent of the entire body without including tail by the animal. If the animal perseveres or fails to leave the arm for longer than five minutes, the session is terminated. In the control population of the animals, the number of errors and exploration of the maze with no prior experience (naive) is approximately 6 errors. This is an average value for an N of 28 gerbils. Following 5 minutes of bilateral carotid occlusion and testing at 24 hours, gerbils make an average number of errors of 21. When animals are pretreated with the glycine/excitatory amino acid antagonists of the invention, there is expected to be a significant reduction in the number of errors made. There is also expected to be a significant sparing of the behavioral changes that are induced in the radial arm maze performance.

It is also expected that post treatment the glycine/excitatory amino acid antagonists of the invention will reduce the short term memory impairment 24 hours post ischemic/reperfusion.

The effects of 5 minutes of bilateral carotid occlusion on neuronal cell death in the dorsal hippocampus may be evaluated in animals 7 days after isehemia reperfusion injury. Previous studies have demonstrated that neuronal degeneration begins to occur around 3 days following cerebral isehemia. By 7 days, those neurons that have been affected will undergo cytolysis and have either completed degeneration or are readily apparent as dark nuclei and displaced nuclei or as cells with eosinophilic cytoplasm and pycnotic nuclei. The lesion with 5 minutes of ischemia is essentially restricted within the hippocampus to the CAI region of the dorsal hippocampus. The intermedial lateral zone of the horn is unaffected and the dentate gyrus and/or in CA3 do not show pathology. Gerbils are anesthetized on day 7 following ischemia with 60 mg/kg of pentobarbital. Brains are perfused transcardiac with ice-cold saline followed by buffered paraformaldehyde (10%). Brains are removed, imbedded and sections made. Sections are stained with hematoxylin-eosin and neuronal cell counts are determined in terms of number of neuronal nuclei/100 micrometers. Normal control animals (not exposed to ischemia reperfusion injury) will not demonstrate any significant change in normal density nuclei within this region. Exposure to five minutes of bilateral carotid occlusion results in a significant reduction in the number of nuclei present in the CA1 region. In general, this lesion results in a patchy necrosis instead of a confluent necrosis which is seen if 10 minutes of ischemia is employed. Pretreatment with the glycine receptor antagonists of the invention is expected to produce a significant protection of hippocampal neuronal degeneration.

It is known that NMDA receptors are critically involved in the development of persistent pain following nerve and tissue injury. Tissue injury such as that caused by injecting a small amount of formalin subcutaneously into the hindpaw of a test animal has been shown to produce an immediate increase of glutamate and aspartate in the spinal cord (Skilling, S. R., et al., *J. Neurosci.* 10:1309–1318 (1990)). Administration of NMDA receptor blockers reduces the response of spinal cord dorsal horn neurons following formalin injection (Dickenson and Aydar, *Neuroscience Lett.* 121:263–266 (1991); Haley, J. E., et al., *Brain Res.* 518:218–226 (1990)). These dorsal horn neurons are critical in carrying the pain signal from the spinal cord to the brain and a reduced response of these neurons is indicative of a reduction in pain perceived by the test animal to which pain has been inflicted by subcutaneous formalin injection.

Because of the observation that NMDA receptor antagonists can block dorsal horn neuron response induced by subcutaneous formalin injection, NMDA receptor antagonists have potential for the treatment of chronic pain such as pain which is caused by surgery or by amputation (phantom pain) or by infliction of other wounds (wound pain). However, the use of conventional NMDA antagonists such as MK-801 or CGS 19755, in preventing or treating chronic pain, is severely limited by the adverse PCP-like behavioral side effects that are caused by these drugs. It is expected that the glycine receptor antagonists that are the subject of this invention will be highly effective in preventing chronic pain in mice induced by injecting formalin subcutaneously into the hindpaw of the animals. Because the glycine/excitatory amino acid antagonists of this invention are expected to be free of PCP-like side effects, these drugs are highly useful in preventing or treating chronic pain without causing PCP-like adverse behavioral side effects.

The effects of the glycine receptor antagonists of the present invention on chronic pain may be evaluated as follows. Male Swiss/Webster mice weighing 25–35 grams are housed five to a cage with free access to food and water and are maintained on a 12 hour light cycle (light onset at 0800 h). The glycine receptor antagonist is dissolved in DMSO at a concentration of 1–40 and 5–40 mg/mL, respectively. DMSO is used as vehicle control. All drugs are injected intraperitoneally (1 µL/g). The formalin test is performed as described (Dubuisson and Dennis, Pain 4:$H_{161-174}$ (1977)). Mice are observed in a plexiglass cylinder, 25 cm in diameter and 30 cm in height. The plantar surface of one hindpaw is injected subcutaneously with 20 µL of 5% formalin. The degree of pain is determined by measuring the amount of time the animal spends licking the formalin-injected paw during the following time intervals: 0–5' (early phase); 5'–10', 10'–15' and 15'–50' (late phase). To test whether the glycine/excitatory amino acid antagonists prevent chronic pain in the test animals, vehicle (DMSO) or drugs dissolved in vehicle at doses of 1 mg/kg to 40 mg/kg are injected intraperitoneally 30 minutes prior to the formalin injection. For each dose of drug or vehicle control at least six animals are used.

Compared to vehicle control, it is expected that the intraperitoneal injection of the glycine receptor antagonists 30 minutes prior to formalin injection into the hindpaw will significantly inhibit formalin-induced chronic pain in a dose-dependent manner as determined by the reduction of the time spent licking by the mouse of the formalin injected hindpaw caused by increasing doses of glycine/excitatory amino acid antagonist.

Compositions within the scope of this invention include all compositions wherein the compounds of the present invention are contained in an amount which is effective to achieve its intended purpose. While individual needs vary, determination of optimal ranges of effective amounts of each component is with the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for anxiety disorders, e.g., generalized anxiety disorder, phobic disorders, obsessional compulsive disorder, panic disorder, and post traumatic stress disorders. Preferably, about 0.01 to about 10 mg/kg is orally administered to treat or prevent such disorders. For intramuscular injection, the dose is generally about one-half of the oral dose. For example, for treatment or prevention of anxiety, a suitable intramuscular dose would be about 0.0025 to about 15 mg/kg, and most preferably, from about 0.01 to about 10 mg/kg.

In the method of treatment or prevention of neuronal loss in ischemia, brain and spinal cord trauma, hypoxia, hypoglycemia, and surgery, as well as for the treatment of Alzheimer's disease, amyotrophic lateral sclerosis, Huntington's disease and Down's Syndrome, or in a method of treating a disease in which the pathophysiology of the disorder involves hyperactivity of the excitatory amino acids or NMDA receptor-ion channel related neurotoxicity, the pharmaceutical compositions of the invention may comprise the compounds of the present invention at a unit dose level of about 0.01 to about 50 mg/kg of body weight, or an equivalent amount of the pharmaceutically acceptable salt thereof, on a regimen of 1–4 times per day. When used to treat chronic pain or to induce anesthesia, the compounds of the invention may be administered at a unit dosage level of from about 0.01 to about 50 mg/kg of body weight, or an equivalent amount of the pharmaceutically acceptable salt thereof, on a regimen of 1–4 times per day. Of course, it is understood that the exact treatment level will depend upon the case history of the animal, e.g., human being, that is treated. The precise treatment level can be determined by one of ordinary skill in the art without undue experimentation.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg,of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular azepine of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular azepine of the present invention with a solution of a pharmaceutically acceptable non-toxic base such as sodium hydroxide, potassium hydroxide, choline hydroxide, sodium carbonate and the like.

The pharmaceutical compositions of the invention may be administered to any animal which may experience the beneficial effects of the compounds of the invention. Foremost among such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations may contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, are present at a concentration of from about 0.01 to 99 percent, together with the excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension include, for example, sodium carboxymethyl cellulose, sorbitol, and/or dextran. Optionally, the suspension may also contain stabilizers.

The characterization of glycine binding sites in vitro has been difficult because of the lack of selective drug ligands. Thus, the glycine ligands of the present invention may be used to characterize the glycine binding site. Particularly preferred azepines of the present invention which may be used for this purpose are isotopically radiolabelled derivatives, e.g. where one or more of the atoms are replaced with $^3$H, $^{11}$C, $^{14}$C, $^{15}$N, or $^{18}$F.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLES

Experimental Section

General. Reagents were used as received unless otherwise noted. Melting points were taken on a Mel-Temp melting point apparatus and are uncorrected. Analytical thin layer chromatography was performed on plastic-backed silica gel 60 $F_{254}$ plates and visualization was effected with an ultraviolet lamp. $^1$H NMR spectra were recorded on a 300 MHz General Electric QE-300; chemical shifts are reported in delta units referenced to residual proton signals of the deuterated solvents (CHCl$_3$, δ7.26; CD$_3$SOCD$_2$H, δ2.49). Infrared spectra were obtained on a Nicolet 5DXB FT-IR or a Nicolet Magna-IR 550 spectrophotometer. Absorptions are recorded in wavenumbers (cm$^{-1}$) and the intensity of the absorptions are indicated by the letters s (strong), m (medium), and w (weak). UV-VIS spectra were obtained on a Perkin Elmer Lambda 6 UV/VIS spectrophotometer. Mass Spectra were recorded on a VG ZAB-2-HF mass spectrometer with a VG-11-250 data system, in the electron ionization mode (70 eV) unless otherwise indicated. Microanalyses were performed by Desert Analytics, Tuscon, Ariz. X-Ray crystallographic data were obtained on a Enraf-Nonius CAD-4 diffractometer.

Example 1

Preparation of 2-Methoxyhydraquinone (37)

In a 500 mL three neck round bottom flask an aqueous solution of NaOH (2N, 88 mL) was degassed with $N_2$ for 30 min while being stirred magnetically. Vanillin (Aldrich, used as received, 24.4 g, 160 mmol) was added to the solution in small portions (200 mg) giving a yellow solution at first then a yellow suspension after ¾ of the vanillin was added. Hydrogen peroxide (Baker, used as received, 30%, 22 g diluted to 112 mL total volume) was added dropwise until the internal temp. was 45° C. (approx. 15 mL). The remainder of the hydrogen peroxide was added at a rate to keep the temp. between 40° C. and 50° C. The reaction became dark and homogeneous upon addition of the hydrogen peroxide. After the addition of peroxide was complete the dark solution was allowed to cool to rt. Sodium chloride (granular, approx. 30 g) was added to the solution and allowed to dissolve. The reaction was then extracted with ethyl ether (1×150 mL then 2×75 mL). The organic phase was dried over sodium sulfate (anhydrous, approx. 10 g) and the solvent was removed (roto-vap) giving a dark oil. Removal of residual solvent by high vacuum resulted in solidification giving a brown solid. The crude solid was re, crystallized by dissolving in hot benzene (300 mL), decolorized with charcoal, filtered while hot then allowed to stand overnight. The resulting light brown solid (7.2 g, 32% yield) showed one spot on TLC ($R_f$=0.4) and was judged to be >95% pure by $^1$H NMR: 87°–90° C., $^1$H NMR (CDCl$_3$) δ3.98 (s, 3H), 4.5 (bs, 1H), 5.3 (bs, 1H), 6.30 (dd, J=8.4, 2.7 Hz, 1H), 6.45 (d, J=2.7 Hz, 1H), 6.78 (d, J=8.4 Hz, 1H).

Example 2

Preparation of 2-Methoxy-1,4-benzoquinone (17)

In a 500 mL beaker NaIO$_4$ (Baker, used as received, 10.6 g, 49.6 mmol) was dissolved in water (distilled, 450 mL) and stirred magnetically. 2-Methoxyhydroquinone (2.2 g, 15.7 mmol) was added giving an orange solution. The mixture was stirred at rt for 1 h then extracted with CH$_2$Cl$_2$ (3×100 mL). The organic extract was washed with brine (1×100 mL), dried by filtering through cotton and evaporated to dryness (roto-vap) giving 2-methoxy-1,4-benzoquinone as a yellow solid (2.1 g, 97%, one spot on TLC, $R_f$=0.5, >95% pure by $^1$H NMR): mp 141°–143° C., $^1$H NMR (CDCl$_3$) δ3.85 (s, 3H), 5.98 (s, 1H), 6.75 (s, 2H).

Example 3

Preparation of 2-Methoxy-8-methylnaphthalene-1,4-dione (33)

The crude 2-methoxy-1,4-benzoquinone (17) was combined with cis/trans-piperylene (20 mL, technical, 90%, Aldrich, used as received), toluene (15 mL) and hydroquinone (100 mg, Mallinkrodt) in a screw top sealed tube (Ace). The tube was heated in a 60° C. oil bath for 22 h, with the contents being stirred magnetically. A pale orange, near homogeneous solution was present. The reaction was allowed to cool to rt, the tube carefully opened, the contents filtered and the solvent removed in vacuo to give an orange solid (3.1 g). TLC analysis (10% EtOAc, 90% CHCl$_3$) showed complete consumption of 17. Without purification, the solid was dissolved in MeOH (190 mL), Et$_3$N (1 mL) added, and the resulting dark solution was allowed to vigorously stir under O$_2$ for 1 h at rt. TLC analysis (10% EtOAc, 90% CHCl$_3$) showed the major Diels-Alder adduct to be consumed, with a major higher $R_f$ spot being formed. Note: Multiple intermediates may be detected by TLC analysis during this reaction. An initial intermediate has a lower $R_f$ than that of the Diels-Alder adduct. A second intermediate has a higher $R_f$ than that of the Diels-Alder adduct. The final product has an $R_f$ slightly lower than this second intermediate but higher than that of the Diels-Alder adduct. Improved yields may be obtained by allowing the reaction to proceed until these intermediates are mostly converted to the final product, which was not the case in this example. The reaction mixture was acidified with 10% HCl (40 mL), diluted with H$_2$O (100 mL) and the MeOH removed in vacuo to give a yellow suspension. The suspension was extracted with CHCl$_3$ (3×75 mL). The extract was washed with saturated NaHCO$_3$ (3×75 mL), and H$_2$O (1×150 mL), filtered through cotton, and the solvent removed in vacuo to give an orange solid (2.5 g). The solid was passed through a silica gel column in the dark with CHCl$_3$ elution (the product is photosensitive in solution). The initial yellow band was collected to give a yellow solid (1.2 g). TLC analysis of this solid showed it to be a two component mixture with the desired product being the major constituent (Note: The desired product was the lower $R_f$ spot. The other spot was the second intermediate described above. The column may not be necessary if the reaction is allowed to proceed to completion). Crystallization from 95% EtOH (20 mL) yielded a yellow solid (662 mg, still impure by TLC analysis). Recrystallization from 95% EtOH (9 mL) yielded 33 as a fluffy yellow solid which was estimated to be 95% pure by $^1$H NMR analysis (565 mg, mp 139°–141° C.). Analytically pure material could be obtained by further recrystallizations; mp 142.5°–143.5° C. (EtOH), lit. (Bohlmann et al., Chem. Ber. 110:2028–2045 (1977)): 146° C.; $^1$H NMR (CDCl$_3$) δ2.76 (s, 3H), 3.90 (s, 3H), 6.14 (s, 1H), 7.50 (d, J=7.5 Hz, 1H), 7.60 (t, J=7.5 Hz, 1H), 8.03 (d, J=7.5 Hz, 1H).

Example 4

Preparation of 2-Methoxy-6,8-dimethylnaphthalene-1,4-dione (34)

To a vigorously stirred solution of NaIO$_4$ (25.1 g, 117.5 mmol, Baker) in water (800 mL), there was added solid 2-methoxyhydroquinone (37, 5.20 g, 37.1 mmol) in portions. The reaction immediately became dark orange. The reaction was allowed to stir for 1 h at rt and was extracted with CH$_2$Cl$_2$ (3×100 mL). The extract was washed with half saturated brine (1×100 mL), filtered through cotton and the solvent removed in vacuo to yield 17 as an orange solid (4.90 g, 96%), which was of sufficient purity (TLC analysis, 10% EtOAc, 90% CHCl$_3$) for further reaction. The crude 17 was combined with trans-2-methyl-1,3-pentadiene (25 mL, technical, 75%, Aldrich, used as received), toluene (50 mL) and hydroquinone (500 mg, Mallinkrodt). The reaction mixture was heated under N$_2$ in a 60° C. oil bath for 20 h, with the contents being stirred magnetically. A pale orange, near homogeneous solution was present. The reaction was allowed to cool to rt, the contents filtered and the solvent removed in vacuo to give an orange solid (9.3 g). TLC analysis (10% EtOAc, 90% CHCl$_3$) showed no remaining 17. Without purification, the solid was dissolved in MeOH (400 mL, a gummy colorless solid (polymer?) failed to dissolve and was removed by filtration), Et$_3$N (3 mL) added, and the resulting dark solution was allowed to vigorously stir under O$_2$ for 2.5 h at rt. TLC analysis (10% EtOAc, 90% CHCl$_3$) showed the major Diels-Alder adduct to be consumed, with a major higher $R_f$ spot being formed. The reaction mixture was acidified with 10% HCl (100 mL), diluted with H$_2$O (200 mL) and the MeOH removed in vacuo to give an orange suspension. The suspension was extracted with CHCl₃ (3×100 mL). The extract was washed with saturated NaHCO₃ (3×75 mL), and H₂O (1×200 mL), filtered through cotton, and the solvent removed in vacuo to give an orange solid (5.9 g). Crystallization from 95% EtOH (170 mL) yielded 34 as yellow needles (2.79 g, 35% from 37, pure by TLC and $^1$H NMR); mp 175.5°–176.5° C. (EtOH); $^1$H NMR (CDCl₃) δ2.44 (s, 3H), 2.72 (s, 3H), 3.88 (s, 3H), 6.10 (s, 1H), 7.30 (s, 1H), 7.82 (s, 1H).

Example 5

Preparation of 2-Methoxy-5,8-dihydro-5,8-dimethylnaphthalene-1,4-dione (38)

To a vigorously stirred solution of NaIO₄ (15.4 g, 72.2 mmol, Baker) in water (500 mL), there was added solid 2-methoxyhydroquinone (37, 3.20 g, 22.8 mmol) in portions. The reaction immediately became dark orange. The reaction was allowed to stir for 1 h at it and was extracted with CH₂Cl₂ (3×75 mL). The extract was washed with half saturated brine (1×75 mL), filtered through cotton and the solvent removed in vacuo to yield 17 as an orange solid (3.02 g, 96%) which was of sufficient purity (TLC analysis, 10% EtOAc, 90% CHCl₃) for further reaction. The crude 17 was combined with 2,4-hexadiene (10 g, isomeric mixture, Aldrich, used as received), toluene (30 mL) and hydroquinone (300 mg, Mallinkrodt). The reaction mixture was heated under N₂ in a 60° C. oil bath for 17.5 h, with the contents being stirred magnetically. A pale orange, near homogeneous solution was present. The reaction was allowed to cool to rt, the contents filtered and the solvent removed in vacuo to give a brown oil (5.8 g). TLC analysis (10% EtOAc, 90% CHCl₃) showed no remaining 17. Without purification, the oil was dissolved in MeOH (270 mL), Et₃N (1.5 mL) added, and the resulting dark solution was allowed to vigorously stir under O₂ for 40 min at rt (Note: Further reaction time may improve the final yield). TLC analysis (10% EtOAc, 90% CHCl₃) showed the major Diels-Alder adduct to be consumed, with a major higher R$_f$ spot being formed. The reaction mixture was acidified with 10% HCl (100 mL), diluted with H₂O (200 mL) and the MeOH removed in vacuo to give an orange suspension. The suspension was extracted with CHCl₃ (3×75 mL). The extract was washed with saturated NaHCO₃ (3×75 mL), and H₂O (1×200 mL), filtered through cotton, and the solvent removed in vacuo to give an orange tacky solid (5.9 g). This was passed through a silica gel column in the dark with CHCl₃ elution (the product is slightly photosensitive in solution). The initial orange band was collected to give an orange solid (3.0 g). Crystallization from 95% EtOH yielded 38 as orange plates (2.22 g, 45% from 37, pure by TLC and $^1$H NMR); mp 110.0°–111.5° C. (EtOH); $^1$H NMR (CDCl₃) δ1.19 (s, 3H), 1.21 (s, 3H), 3.40 (m, 2H), 3.81 (s, 3H), 5.78 (m, 2H), 5.88 (s, 1H). Note: Further reaction of this compound with O₂ in Et₃N/MeOH failed to produce the subsequent aromatic compound.

Example 6

Preparation of 2-Methoxy-5,8-dimethylnaphthalene-1,4-dione (35)

To a stirred solution of 2-methoxy-5,8-dihydro-5,8-dimethylnaphthalene-1,4-dione (38, 500 mg, 2.29 mmol) in toluene (12 mL) there was added DDQ (1.30 g, 5.72 mmol, freshly crystallized form benzene, mp 207°–208.5° C.). The resulting stirred suspension was heated at reflux under N₂ for 2.6 hr at which point TLC analysis (CHCl₃) indicated near total consumption of the dihydro compound and the formation of a slightly lower R$_f$ product. The reaction was allowed to cool to rt. The suspended material (dihydro DDQ?) was removed by filtration and washed with fresh toluene until the wash was colorless (4×3 mL). The toluene was removed in vacuo and the residue dissolved in CHCl₃ (60 mL). This solution was washed with 25% saturated NaHCO₃ (5×40 mL) and half saturated brine (1×40 mL), filtered through cotton and the solvent removed in vacuo to give a dark brown solid (442 mg, 89% recovery). A total of 980 mg of crude material was passed through a silica gel column (2.5×25 cm) with CHCl₃ elution to give a green solid (906 mg). Crystallization from 95% EtOH (dissolved in 20 mL, decolorized with charcoal, hot filtered, allowed to cool to rt) yielded 35 as a greenish yellow crystalline solid (612 mg, 62% recovery from crude, pure by TLC and aH NMR); mp 144.5°–146.0° C. (EtOH); $^1$H NMR (CDCl₃) δ2.71 (s, 6H), 3.86 (s, 3H), 6.06 (s, 1H), 7.35 (d, J=8.1, Hz, 1H), 7.39 (d, J=8.1, 1H).

Example 7

Preparation of 2-Methoxy-6,7-dimethylnaphthalene-1,4-dione (36)

To a vigorously stirred solution of NaIO₄ (25.1 g, 117.5 mmol, Baker) in water (800 mL), there was added solid 2-methoxyhydroquinone (37, 5.20 g, 37.1 mmol) in portions. The reaction immediately became dark orange. The reaction was allowed to stir for 1 h at rt and was extracted with CH₂Cl₂ (3×100 mL). The extract was washed with half saturated brine (1×100 mL), filtered through cotton and the solvent removed in vacuo to yield 17 as an orange solid (4.80 g, 94%), which was of sufficient purity (TLC analysis, 10% EtOAc, 90% CHCl₃) for further reaction. The crude quinone was combined with 2,3-dimethyl-1,3-butadiene (9.3 mL, Aldrich, used as received), toluene (50 mL) and hydroquinone (500 mg, Mallinkrodt). The reaction mixture was heated under N₂ in a 60° C. oil bath for 17 h, with the contents being stirred magnetically. A pale orange, near homogeneous solution was present. The reaction was allowed to cool to rt, the contents filtered and the solvent removed in vacuo to give a brown solid (8.1 g). TLC analysis (10% EtOAc, 90% CHCl₃) showed no remaining 17. Without purification, the solid was dissolved in MeOH (500 mL, a gummy colorless solid (polymer?) failed to dissolve and was removed by filtration), Et₃N (4 mL) added, and the resulting dark solution was allowed to vigorously stir under O₂ for 3.0 h at rt. TLC analysis (10% EtOAc, 90% CHCl₃) showed the major Diels-Alder adduct to be consumed, with a major higher R$_f$ spot being formed. The reaction mixture was acidified with 10% HCl (100 mL), diluted with H₂O (200 mL) and the MeOH removed in vacuo to give an orange suspension. The suspension was extracted with CHCl₃ (3×100 mL). The extract was washed with saturated NaHCO₃ (3×75 mL), and H₂O (1×200 mL), filtered through cotton, and the solvent removed in vacuo to give an orange solid (5.1 g). Crystallization from 95% EtOH (100 mL) yielded the product as yellow needles (2.27 g, 35% from 2-methoxyhydroquinone, 90% pure by TLC and $^1$H NMR). Further crystallization from 95% EtOH failed to improve the purity; mp 161.5°–162.5° C. (EtOH), lit. (Trave et al., Chim. e ind. (Milan) 41:19–29 (1959)) 166° C.; $^1$H NMR (CDCl₃) δ2.39 (s, 6H), 3.88 (s, 3H), 6.10 (s, 1H), 7.82 (s, 1H), 7.88 (s, 1H). Note: The impurity is probably 2-methoxy-5,8-dihydro-6,7-dimethylnaphthalene-1,4-dione.

Example 8

Reaction of 17 with 1-Acetoxy-1,3-butadiene (Adduct 29)

In a 50 mL round bottom flask, 2-methoxy-1,4-benzoquinone (17, 2.0 g, 14.5 mmol) was dissolved in toluene (19 mL). Hydroquinone (95 mg, Mallinkrodt) was added and the resulting suspension stirred magnetically for 5 minutes. 1-Acetoxy-1,3-butadiene (5.5 g, 5.7 mL, 49.3 mmol, Aldrich used as received, a mixture of isomers) was then added in one portion and the reaction was heated under $N_2$ at 60° C. using an oil bath for 18 h. The reaction flask was removed from the oil bath and allowed to cool to rt then cooled to 5° C. using an ice bath. The resulting solid was collected by filtration and washed with hexane (15 mL). Crystallization of the crude solid by dissolving in hot benzene (25 mL) and then allowing to cool to rt afford the desired product as a colorless solid (1.72 g, 6.88 mmol, 49%); mp 138°–141° C.; $^1$H NMR (CDCl$_3$) δ1.88 (s, 3H), 2.0–2.3 (m, 1H), 3.1 (m, 1H), 3.2–3.4 (m, 1H), 3.45 (t, 1H), 3.83 (s, 3H), 5.38 (t, 1H), 5.9–6.1 (m, 1H), 6.14 (s, 1H).

Example 9

Reaction of 17 with trans, trans-2,4-hexadiene-1-ol (Adducts 30 and 31)

In a 50 mL round bottom flask, 2-methoxy-1,4-benzoquinone (17, 1.0 g, 7.2 mmol) was dissolved in toluene (10 mL). Hydroquinone (10 Mallinkrodt) was added and the resulting suspension stirred magnetically for 5 minutes. Trans, trans-2,4-hexadiene-1-ol (1.1 g, 1.25 mL, 11.1 mmol, Aldrich used as received) was then added in one portion and the reaction was heated under $N_2$ at 60° C. using an oil bath for 18 h. The reaction was removed from the oil bath, cooled to room temperature and the solvent was removed by evaporation. The resulting oil was chromatographed using a silica gel column (20 cm×2 cm) with CHCl$_3$ elution. Evaporation of the solvent resulted in a light oil which crystallized upon standing. This afforded partial separation of the regioisomers. Further purification involved recrystallization from minimal amount of methanol (1 mL) and cooling to −30° C. to yield an initial adduct (220 mg, 0.93 mmol, 26%); mp 124°–127° C.; $^1$H NMR (CDCl$_3$) δ1.63 (d, 3H), 3.52 (m, 1H), 3.89 (s, 3H), 3.89 (m, 1H), 4.02 (d, 1H), 4.05 (d, 1H), 4.82 (t, 1H), 5.50 (s, 1H), 5.88 (dd, 2H), 6.42 (s, 1H).

Concentration of the mother liquor yielded the second adduct (160 mg, 0.68 mmol, 19%); mp 137°–140° C.; $^1$H NMR (CDCl$_3$) δ1.63 (d, 3H), 3.52 (m, 1H), 3.89 (s, 3H), 3.89 (m, 1H), 4.02 (d, 1H), 4.05 (d, 1H), 4.82 (t, 1H), 5.50 (s, 1H), 5.88 (dd, 2H), 6.35 (s, 1H).

Example 10

Reaction of 17 with Danishefsky's diene (Adduct 32)

In a 50 mL round bottom flask, 2-methoxy-1,4-benzoquinone (2.3 g, 16.7 mmol) was suspended in toluene (30 mL). Hydroquinone (95 mg) was added and the resulting suspension was stirred magnetically for 5 min. 1-Methoxy-3-trimethylsilyloxy-1,3-butadiene (Aldrich, used as received, 5.0 g, 4.5 mL, 29.1 mmol) was added in one portion and the reaction was heated under $N_2$ at 60° C. using an oil bath for 18 h. The reaction was removed from the oil bath, allowed to cool to rt and the solvent was removed by evaporation. Crystallization occurred after cooling the mixture to −30° C. for 1 hour. The colorless solid was collected by filtration and washed with hexane (30 mL) giving 4a,5,8,8a-tetrahydro-2,8-dimethoxy-6-trimethylsilyloxynapthalene-1,4-dione:

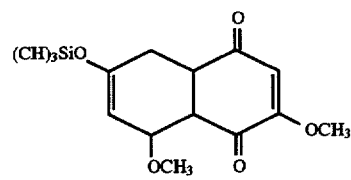

as a colorless powder (3.6 g, 11.6 mmol, 70%, >95% pure by $^1$H NMR, mp 108°–110° C.; $^1$H NMR (CDCl$_3$) δ0.52 (s, 9H), 2.2–2.4 (m, 2H), 3.18 (s, 3H), 3.47 (t, 1H), 3.80 (s, 3H), 3.92 (m, 2H), 5.20 (d, 1H), 6.12 (s, 1H).

Example 11

Preparation of 2-Methoxy-6-hydroxy-1,4-naphthoquinone

In a 50 mL round bottom flask, 4a,5,8,8a-tetrahydro-2,8-dimethoxy-6-trimethylsilyloxynapthalene-1,4-dione (3.0 g from above procedure) was dissolved in methanol (25 mL) and stirred magnetically for 5 min. Triethylamine (Aldrich, used as received, 5.0 mL) was added all at once. The color changed from a light yellow to red after the addition of triethylamine. The reaction was stirred for 2 hours exposed to air. After acidification of the red solution to pH 7.5 with HCl (10%, approx. 65 mL) a yellow precipitate formed and was collected by filtration that appeared orange after filtration. The orange solid was dried under vacuum (0.1 torr) giving 2-methoxy-6-hydroxy-1,4-naphthoquinone:

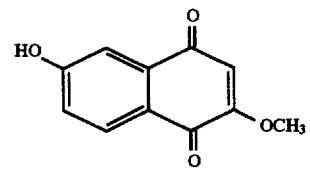

(1.8 g, 91%, >95% pure by $^1$H NMR: mp 264°–267° C.; $^1$H NMR (DMSO-d$_6$) δ3.81 (s, 3H), 6.22 (s, 1H), 7.15 (dd, J=2.5, 8.5, 1H), 7.24 (d, J=2.5, 1H), 7.83 (d, J=8.5, 1H), 10.98 (s, 1H). Anal. Calcd for C$_{11}$H$_8$O$_4$: C, 64.71; H, 3.95. Found: C, 64.58; H, 3.81.

Example 12

Preparation of 2-Methoxy-5,7-dibromo-6-hydroxy-1,4-naphthoquinone

In a 100 mL round bottom flask, 2-methoxy-6-hydroxy-1,4-naphthoquinone (500 mg, 2.45 mmol) was dissolved in DMF (Baker, 50 mL) and magnetically stirred for 5 min giving a yellow solution. N-Bromosuccinimide (NBS, Aldrich, used without purification, 784.5 mg, 4.41 mmol, 1.8 eq) was added all at once resulting in a light yellow solution that was stirred for 18 h at rt under an atmosphere of $N_2$. The yellow homogenous mixture was diluted with CH$_2$Cl$_2$ (100 mL) and washed with water (3×50 mL) to remove the majority of the DMF. The desired product was extracted from the organic phase with a 1.0M solution of NaHCO$_3$ (3×50 mL) giving a dark purple aqueous solution. The organic phase was washed with water (1×50 mL), dried over MgSO$_4$ and evaporated to dryness (roto-vap) giving recovery of the starting material (70 mg, 0.34 mmol, 14%). The dark purple aqueous solution was carefully acidified to pH 7.4 by dropwise addition of HCl (conc., approx 10 mL). A sharp color change from purple to yellow signaled the neutralization of the solution. The yellow aqueous solution was extracted with CH$_2$Cl$_2$ (3×100 mL) leaving the aqueous phase almost colorless. The CH$_2$Cl$_2$ phase was washed with water (1×50 mL), dried over MgSO$_4$ and evaporated to dryness (roto-vap). The resulting yellow solid was 85% pure determined by $^1$H NMR. The adduct was purified by dissolving in hot ethanol (20 mL), hot filtration and cooling to rt then recovered by filtration to give the desired 2-methoxy-5,7-dibromo-6-hydroxy-1,4-naphthoquinone as a yellow powder (709 mg, 76%, one spot on TLC and >90% pure by $^1$H NMR: mp 224°–228° C.; $^1$H NMR (CDCl$_3$) δ3.85 (s, 3H), 6.18 (s, 1H), 7.16 (s, 1H), 8.34 (s, 1H). Anal. Calcd for C$_{11}$H$_6$Br$_2$O$_4$: C, 36.50; H, 1.67. Found: C, 36.35; H, 1.64.

Example 13

Preparation of 3-Methoxy-9-methyl-1H-1-benzazepine-2,5-dione (39)

To stirred, ice bath cold CF$_3$SO$_3$H (3.0 mL, Aldrich), there was added 2-methoxy-8-methylnaphthalene-1,4-dione (33, 483 mg, 2.39 mmol, 95%) in portions. A deep red solution resulted. To this cold solution, NaN$_3$ (186.0 mg, 2.87 mmol, Aldrich) was added in portions. The reaction was allowed to slowly attain rt with stirring under N$_2$. Gas evolution was noted. After 24 h, the reaction was judged complete by TLC analysis (10% EtOAc, 90% CHCl$_3$). The reaction was added to swirled ice/H$_2$O (30 mL) to give a green, sticky suspension. This was extracted with 30% MeOH, 70% CHCl$_3$ (4×25 mL) to give a green organic solution. This was washed with water (3×50 mL, organic phase now red), filtered through cotton and the solvent removed in vacuo to give a purple solid (500 mg). This was partitioned by vacuum chromatography on silica gel (2.5×25 era) with CHCl$_3$ elution to give an unknown fast eluting material (50 mg, unstable) followed by partially purified desired product (367 mg, orange solid). The product fraction was crystallized from 95% EtOH (dissolved in 20 mL, decolorized with activated charcoal, hot filtered, concd to 15 mL) to yield 39 as beige needles (245 mg). This material was judged to be greater than 95% pure by $^1$H NMR analysis. An analytical sample was prepared by recrystallization from 95% EtOH (41 mg, 1.5 mL) to give near colorless needles (28 mg, 68% recovery, pure by TLC and $^1$H NMR); mp 187.5°–188.5° C. (EtOH); $^1$H NMR (DMSO-d$_6$) δ2.41 (s, 3H), 3.75 (s, 3H), 6.26 (s, 1H), 7.18 (t, J=7.8 Hz, 1H), 7.46 (d, J=7.5 Hz, 1H), 7.52 (d, J=8.1 Hz, 1H), 9.45 (s, 1H); MS m/z 217 (M$^+$, 100).

Example 14

Preparation of 3-Methoxy-7,9-dimethyl-1H-1-benzazepine-2,5-dione (40)

To stirred, ice bath cold, concd H$_2$SO$_4$ (9.0 mL, Baker), there was added 2-methoxy-6,8-dimethylnaphthalene-1,4-dione (34, 500 mg, 2.31 mmol) in portions. A deep red solution resulted. To this cold solution, NAN$_3$ (300.0 mg, 4.62 mmol, Aldrich) was added in portions. The reaction was allowed to slowly attain rt with stirring under N$_2$. Gas evolution was noted. After 24 h, the reaction was judged complete by TLC analysis (10% EtOAc, 90% CHCl$_3$). The reaction was added to swirled ice/H$_2$O (25 mL) to give a green, sticky suspension. This was extracted with 30% MeOH, 70% CHCl$_3$ (3×30 mL) to give a green organic solution. This was washed with water (2×50 mL, organic phase now red), half saturated NaHCO$_3$ (1×50 mL) and H$_2$O (1×50 mL), filtered through cotton and the solvent removed in vacuo to give a purple solid (400 mg). Preliminary purification was effected by vacuum chromatography on silica gel (2.5×25 cm) with CHCl$_3$ elution to give partially purified desired product (360 mg, orange solid). This was crystallized from 95% EtOH (dissolved in 7 mL, hot filtered, allowed to cool to rt then in an ice bath) to yield 40 as near colorless laths (253 mg, 47%, pure by TLC and $^1$H NMR); mp 187.0°–188.5° C. (EtOH), $^1$H NMR (DMSO-d$_6$) δ2.27 (s, 3H), 2.37 (s, 3H), 3.74 (s, 3H), 6.24 (s, 1H), 7.30 (s, 1H), 7.32 (s, 1H), 9.90 (s, 1H); MS m/z 231 (M$^+$, 100).

Example 15

Preparation of 3-Methoxy-6,9-dimethyl-1H-1-benzazepine-2,5-dione (41)

To stirred, ice bath cold, concd H$_2$SO$_4$ (11.0 mL, Baker), there was added 2-methoxy-5,8-dimethylnaphthalene-1,4-dione (35, 600 mg, 2.77 mmol) in portions. A deep red solution resulted. To this cold solution, NaN$_3$ (360.0 mg, 5.54 mmol, Aldrich) was added in portions. The reaction was allowed to slowly attain rt with stirring under N$_2$. Gas evolution was noted. After 24 h, the reaction was judged complete by TLC analysis (10% EtOAc, 90% CHCl$_3$). The reaction was added to swirled ice H$_2$O (40 mL) to give a green, sticky suspension. This was extracted with 30% MeOH, 70% CHCl$_3$ (3×30 mL) to give a green organic solution. This was washed with water (2×50 mL, organic phase now red), half saturated NaHCO$_3$ (1×50 mL), H$_2$O (2×50 mL) and brine (1×50 mL), filtered through cotton and the solvent removed in vacuo to give a dark brown solid (402 mg). This was purified by vacuum chromatography on silica gel (1.5×25 cm) with CHCl$_3$ elution to give partially purified desired product (316 mg, light brown solid). This was crystallized from 95% EtOH (dissolved in 15 mL, decolorized with activated charcoal, hot filtered, concd to 8 mL) to give 41 as a near colorless fine crystalline solid (209 mg, 32%). This material was judged to be greater than 95% pure by TLC and $^1$H NMR analyses; mp 224°–226° C. (EtOH). A pure sample was obtained by re. crystallization from 95% EtOH (18 mg in 0.5 mL yielded 13 mg, pure by TLC and $^1$H NMR); mp 226.5°–227.5° C. (EtOH). $^1$H NMR (DMSO-d$_6$) δ2.24 (s, 3H), 2.32 (s, 3H), 3.68 (s, 3H), 6.28 (s, 1H), 7.04 (d, J=7.8 Hz, 1H), 7.24 (d, J=7.5 Hz, 1H), 9.95 (s, 1H); MS m/z 231 (M$^+$, 80).

Example 16

Preparation of 3-Methoxy-7,8-dimethyl-1H-1-benzazepine-2,5-dione (42)

To stirred, ice bath cold, concd H$_2$SO$_4$ (9.0 mL, Baker), there was added 2-methoxy-6,7-dimethylnaphthalene-1,4-dione (500 mg, 2.31 mmol, 90% pure) in portions. A deep red solution resulted. To this cold solution, NaN$_3$ (300 mg, 4.62 mmol, Aldrich) was added in portions. The reaction was allowed to slowly attain rt with stirring under N$_2$. Gas evolution was noted. After 24 h, the reaction was judged to be 75% complete by TLC analysis (10% EtOAc/90% CHCl$_3$). The reaction was recooled in an ice bath and an additional portion of NaN$_3$ (75 mg, 1.13 mmol) was added. After an additional 24 h at rt, the reaction was added to swirled ice H$_2$O (25 mL) to give a green, sticky suspension. This was extracted with 30% MeOH/70% CHCl$_3$ (6×30 mL) to give a green organic solution. This was washed with water (2×50 mL), half saturated NaHCO$_3$ (1×50 mL) and H$_2$O (1×50 mL), filtered through cotton and the solvent removed in vacuo to give a brown solid (464 mg). Crystallization from 95% EtOH (dissolved in 125 mL, decolorized with charcoal, hot filtered (Whatman #2), concd to 50 mL, allowed to cool to rt) yielded a pale yellow solid (305 mg, 57%, pure by TLC and $^1$H NMR); mp 293.5°–295° C. (EtOH) (lit, 295°–298° C., Birchall, G. R. et al. Can. J. Chem. 52:610–615 (1974)); $^1$H NMR (DMSO-d$_6$) δ2.23 (s, 6H), 3.78 (s, 3H), 6.31 (s, 1H), 7.17 (s, 1H), 7.70 (s, 1H), 11.19 (s, 1H); MS m/z 231 (M$^+$, 100).

Example 17

Preparation of 3-Hydroxy-7,8-dimethyl-1H-1-benzazepine-2,5-dione (46)

To a stirred suspension of 3-methoxy-7,8-dimethyl-1H-1-benzazepine-2,5-dione (270 mg, 1.17 mmol) in dry $CH_2CH_2$ (2.7 mL, distilled from $CaH_2$) under $N_2$, there was added a solution of $BBr_3$ in $CH_2Cl_2$ (2.7 mL, 1 M, Aldrich) in one portion over 20 seconds at rt. The reaction instantaneously became homogeneous and orange, then a brown precipitate formed after a few seconds. The reaction was allowed to stir under $N_2$ at rt for 45 min. The reaction was added to saturated $NaHCO_3$ (30 mL) and was allowed to stir for 15 min at rt to give a yellow suspension. The resulting suspension was acidified with concd HCl (pH 2), the acidic suspension stirred for 10 min at rt, the solid collected by filtration and washed to neutrality with water (6×4 mL). The damp filter cake was crystallized from 95% EtOH (dissolved in 550 mL, hot filtered, concd to 210 mL, allowed to cool to rt) to yield a fine yellow solid (195 mg, 77%, pure by TLC, $^1$H NMR and C,H,N analysis); mp 302°–304° C. (dec. EtOH) (lit 288° C. (dec) Birchall, G. R. et al. *Can. J. Chem.* 52:610–615 (1974)); $^1$H NMR (DMSO-$d_6$) δ2.24 (d, 6H), 6.39 (s, 1H), 7.24 (s, 1H), 7.80 (s, 1H), 10.46 (s, 1H), 11.49 (s, 1H); Anal. Calcd for $C_{12}H_{11}NO_3$ : C, 66.35; H, 5.10; N, 6.45. Found: C, 66.30; H, 4.88; N, 6.25.

Example 18

Preparation of 3-Hydroxy-9-methyl-1H-1-benzazepine-2,5-dione (43)

To a stirred suspension of 3-methoxy-9-methyl-1H-1-benzazepine-2,5-dione (39, 200 mg, 921 µmol) in dry $CH_2Cl_2$ (2 mL, distilled from $CaH_2$) under $N_2$, there was added a solution of $BBr_3$ in $CH_2Cl_2$ (2 mL, 1M, Aldrich) in one portion at rt. The reaction instantaneously became homogeneous and yellow, then a yellow precipitate formed after a few seconds. The reaction was allowed to stir under $N_2$ at rt for 45 min. The reaction was added to saturated $NaHCO_3$ (15 mL) and the resulting beige suspension was allowed to stir for 15 min to give a cloudy, orange solution. The solution was filtered through glass wool to remove any suspended matter. The resulting solution was acidified with concd HCl (pH 2), the solid collected by filtration and washed to neutrality with water (5×2 mL). The damp filter cake was crystallized from 95% EtOH (dissolved in 15 mL, hot filtered, concd to 7 mL) to yield 43 as brown needles (98 mg, 52%, pure by TLC, $^1$H NMR and C,H,N analyses); mp 184°–185.5° C. (EtOH), $^1$H NMR (DMSO-$d_6$) δ2.46 (s, 3H), 6.28 (s, 1H), 7.19 (t, J=7.5 Hz, 1H), 7.53 (d, J=7.2 Hz, 1H), 8.03 (d, J=7.8 Hz, 1H), 9.94 (s, 1H), 10.85 (bs, 1H); Anal. Calcd for $C_{11}H_9NO_3 \cdot 0.5\ H_2O$: C, 62.26; H, 4.75; N, 6.60. Found: C, 62.39; H, 4.53; N, 6.51.

Example 19

Preparation of 3-Hydroxy-7,9-dimethyl-1H-1-benzazepine-2,5-dione (44)

To a stirred suspension of 3-methoxy-7,9-dimethyl-1H-1-benzazepine-2,5-dione (272 mg, 1.18 mmol) in dry $CH_2Cl_2$ (3 mL, distilled from $CaH_2$) under $N_2$, there was added a solution of $BBr_3$ in $CH_2Cl_2$ (3 mL, 1M, Aldrich) in one portion over 10 seconds at rt. The reaction instantaneously became homogeneous and orange, then an orange precipitate formed after a few seconds. The reaction bubbled vigorously during the addition. The reaction was allowed to stir under $N_2$ at rt for 45 min. The reaction was added to saturated $NaHCO_3$ (30 mL) and the resulting beige suspension was allowed to stir for 15 min to give a cloudy, yellow solution. The solution was filtered through glass wool to remove any suspended matter. The resulting solution was acidified with concd HCl (pH 2), the solid collected by filtration and washed to neutrality with water (6×5 mL). The damp filter cake was crystallized from 95% EtOH (dissolved in 20 mL, hot filtered, allowed to cool to rt) to yield yellow needles (176 mg, 69%, pure by TLC, $^1$H NMR and C,H,N analysis); mp 211°–213° C. (EtOH), $^1$H NMR (DMSO-$d_6$) δ2.28 (s, 3H), 2.42 (s, 3H), 6.27 (s, 1H), 7.31 (s, 1H), 7.47 (s, 1H), 9.90 (s, 1H), 10.74 (bs, 1H); Anal. Calcd for $C_{12}H_{11}NO_3$: C, 66.35; H, 5.10; N, 6.45. Found: C, 66.34; H, 5.13; N, 6.48.

Example 20

Preparation of 3-Hydroxy-6,9-dimethyl-1H-1-benzazepine-2,5-dione (45)

To a stirred suspension of 3-methoxy-6,9-dimethyl-1H-1-benzazepine-2,5-dione (230 mg, 994 µmol) in dry $CH_2Cl_2$ (2 mL, distilled from $CaH_2$) under $N_2$, there was added a solution of $BBr_3$ in $CH_2Cl_2$ (2 mL, 1M, Aldrich) in one portion over 20 seconds at rt. The reaction instantaneously became dark, then a purple precipitate formed after a few seconds. The reaction bubbled vigorously during the addition. The reaction was allowed to stir under $N_2$ at rt for 45 min. The reaction was added to saturated $NaHCO_3$ (15 mL) and the resulting purple suspension was allowed to stir for 15 min to give a cloudy, green solution. The solution was extracted with $CHCl_3$, which removed red color but no product as determined by TLC (10% MeOH/90% $CHCl_3$). The aqueous portion was adjusted to pH 2 with concd HCl and extracted with $CHCl_3$ (3×15 mL, purple solution). This was washed with $H_2O$ (20 mL) and 50% saturated brine (20 mL), filtered through cotton and the solvent removed in vacuo to yield a purple solid (120 mg). This was dissolved in MeOH (50 mL), stirred with activated charcoal (3 spatula tips) for 15 min at rt, filtered (Whatman #2) and the solvent removed in vacuo to give a bone solid (110 mg). Final purification was effected by crystallization from $CH_2Cl_2$/ether (dissolved in $CH_2Cl_2$, 8 mL; filtered; allowed to cool to rt; placed in ether chamber for 72 h) to yield the product as yellow needles (25 mg, 12%, pure by TLC, and C,H,N analysis, >98% pure by $^1$H NMR); mp 183°–185° C. (dec.); $^1$H NMR (DMSO-$d_6$) δ2.24 (s, 3H), 2.35 (s, 3H), 6.20 (s, 1H), 7.03 (d, J=7.8 Hz, 1H), 7.25 (d, J=7.8 Hz, 1H), 9.98 (s, 1H), 10.53 (bs, 1H); Anal. Calcd for $C_{12}H_{11}NO_3$: C, 66.35; H, 5.10; N, 6.45. Found: C, 66.34; H, 4.91; N, 6.32.

Example 21

Preparation of 1,4,4a, 8a-Tetrahydro-6-methoxy-1,4-methanonaphthalene-5,8-dione (47)

The procedure employed was a modification of that used by Okamato et al. (*Chem. Pharm. Bull* 32:4593–4599 (1984)). To a vigorously stirred solution of $NaIO_4$ (15.4 g, 72.2 mmol, Baker) in water (500 mL), there was added solid 2-methoxyhydroquinone (37, 3.20 g, 22.8 mmol) in portions. The reaction immediately became dark orange. The reaction was allowed to stir for 1 h at rt and was extracted with $CH_2Cl_2$ (3×100 mL). The extract was washed with half saturated brine (1×100 mL), filtered through cotton and the solvent removed in vacuo to yield 17 as an orange solid (3.07 g, 97%), which was of sufficient purity (TLC analysis, 10% EtOAc, 90% $CHCl_3$) for further reaction. The crude 17 was combined with hydroquinone (300 mg, Mallinkrodt), toluene (20 mL) and freshly distilled cyclopentadiene (15 mL, from the distillation of dicyclopentadiene, Aldrich). The reaction was allowed to stir at rt for 35 min at which point an orange homogeneous solution was present. TLC analysis (10% EtOAc, 90% CHCl$_3$) indicated total conversion of the 2-methoxybenzoquinone to the lower R$_f$ adduct. The lower boiling volatiles were removed in vacuo to give an orange liquid. Washing the liquid with ice cold hexanes yielded a beige solid (4.4 g). This was purified chromatographically (silica gel, 2.5×25 cm, CHCl$_3$ elution) to yield an oil. Trituration with hexanes (50 mL), ice cold ether (3×10 mL) and hexanes (1×10 mL) yielded 46 as a pinkish powder (3.00 g, 64%, pure by TLC and $^1$H NMR); mp 95°–97° C., lit. (Okamato et al.) 97°–99.5° C.; $^1$H NMR (CDCl$_3$) δ1.44 (d, J=9.0 Hz, 1H), 1.55 (m, 1H), 3.24 (m, 2H), 3.55 (m, 2H) 3.72 (s, 3H), 5.89 (s, 1H), 6.07 (m, 2H).

Example 22

Preparation of 1,4-Dihydro-6-methoxy-1,4-methanonaphthalene-5,8-diol (48); NaN$_3$ in AcOH method To a solution of 1,4,4a,8a-tetrahydro-6-methoxy-1,4-methanonaphthalene-5,8-dione (47, 204 mg, 1.00 mmol) in glacial AcOH (3 mL) there was added NaN$_3$ (130 mg, 2.00 mmol, Aldrich). The mixture was gently heated on a steam bath with occasional swirling for 30 min, at which point it had become dark brown. The reaction was allowed to stand for 2 h at rt, then it was added to ice/H$_2$O (80 mL). The resulting dark solution was extracted with CHCl$_3$ (3×25 mL) and the extract washed with H$_2$O (3×50 mL), filtered through cotton and the solvent removed in vacuo to give a pink solid (146 mg). Partial purification was effected by silica gel chromatography (1×15 cm) with CHCl$_3$ elution to give a brown sticky solid. Final purification was effected by crystallization from ether/hexanes (dissolved in warm ether (6 mL), decolorized with activated charcoal, filtered through celite, concd to 1 mL, added hexanes to cloudiness (~4 mL), added a trace of ether to clarify, covered tube with Kimwipe, allowed to evaporate to ~2 mL during which time crystals formed) to yield 47 as a grey solid (43 mg, 33%, pure by TLC and $^1$H NMR); mp 153°–156° C.; $^1$H NMR (CDCl$_3$) δ2.14 (d, J=6.9 Hz, 1H), 2.21 (d, J=6.9 Hz, 1H), 3.79 (s, 3H), 3.99 (s, 1H), 4.17 (s, 1H), 4.26 (s, 1H), 5.20 (s, 1H), 6.03 (s, 1H), 6.77 (m, 2H).

Example 23

Preparation of 1,4-Dihydro-6-methoxy-1,4-methanonaphthalene-5,8-diol (48); Na$_2$CO$_3$ in MeOH method To stirred MeOH (65 mL), which had been purged with N$_2$ for 5 min, there was added 1,4,4a,8a-tetrahydro-6-methoxy-1,4-methanonaphthalene-5,8-dione (47, 1.50 g, 7.30 mmol) to give a solution. Solid Na$_2$CO$_3$ (2.02 g, 14.6 mmol) was then added under N$_2$. The resulting light green suspension was allowed to stir under N$_2$ for 15 min at rt. TLC analysis (10% MeOH, 90% CHCl$_3$) indicated total consumption of the organic starting material. While still under N$_2$, the reaction was diluted with H$_2$O (20 mL). The pH was adjusted to slightly acidic by the slow and careful addition of concd HCl, after which the solution was light pink. The methanol was then removed in vacuo (vacuum relieved with N$_2$) to give a light green solution. The pH was approximately 8. The pH was then adjusted to 2 with 10% HCl at which point the product crystallized. The crystals were collected, washed with 10% HCl (4×3 mL) and dried in vacuo to yield 48 as a near colorless crystalline solid (1.32 g, 88%, pure by TLC and $^1$H NMR); mp 151°–153° C.; $^1$H NMR (vide infra).

Example 24

Preparation of 1,4-Dihydro-6-methoxy-1,4-methanonaphthalene-5,8-dione (49)

To a vigorously stirred solution of NaIO$_4$ (471 mg, 2.20 mmol; Baker) in water (15 mL), there was added solid 1,4-dihydro-6-methoxy-1,4-methanonaphthalene-5,8-diol (48, 150 mg, 734 µmol) in one portion. The reaction immediately became orange and a precipitate formed. The reaction was allowed to stir at rt for 15 min at which point TLC analysis (10% EtOAc, 90% CHCl$_3$) indicated total consumption of 48. The reaction mixture was extracted with CHCl$_3$ (3×15 mL). The extract was washed with half saturated brine (1×25 mL), filtered through cotton and the solvent removed in vacuo to yield a gummy yellow solid. This was triturated with hexanes (2 mL) and dried in vacuo to yield 49 as a yellow powder (134 mg, 90%, pure by TLC and $^1$H NMR); mp 117°–118° C.; $^1$H NMR (CDCl$_3$) δ2.26 (d, J=7.2 Hz, 1H), 2.33 (d, J=6.9 Hz, 1H), 3.79 (s, 3H), 4.10 (m, 2H), 5.70 (s, 1H), 6.86 (m, 2H). Note: this material decomposes if stored for extended periods at rt.

Example 25

Preparation of 1,4,4a, 8a-Tetrahydro-4a or 8a-azido-6-methoxy-1,4-methanonaphthalene-5,8-dione (50 or 51)

To a solution of 1,4,4a,8a-tetrahydro-6-methoxy-1,4-methanonaphthalene-5,8-dione (47, 613 mg, 3.00 mmol) in glacial AcOH (9 mL) there was added NaN$_3$ (390 mg, 6.00 mmol, Aldrich). The mixture was gently heated on a steam bath with occasional swirling for 30 min, at which point it had become dark brown. The reaction was allowed to stand for 3 h at rt, then it was added to H$_2$O (100 mL). Solid NaIO$_4$ (2.82 g, 13.2 mmol, Baker) was added to the stirred solution and stirring was continued for 15 min at rt. The reaction was extracted with CHCl$_3$ (3×25 mL), the extract washed with H$_2$O (3×75 mL), filtered through cotton and the solvent removed in vacuo to give a dark solid (617 mg). Preliminary purification was effected on silica gel (2.5×15 cm) with CHCl$_3$ elution to yield a yellow solid (362 mg). Final purification was effected by crystallization from MeOH (dissolved in 12 mL, hot filtered, allowed to cool to rt then in an ice bath) to yield 50 or 51 as pale yellow flakes (125 mg, pure by TLC and $^1$H NMR); mp 142°–142.5° C. dec; $^1$H NMR (CDCl$_3$) δ1.72 (d, J=9.0 Hz, 1H), 1.94 (d, J=9.3 Hz, 1H), 2.86 (d, J=4.2 Hz, 1H), 3.52 (m, 2H), 3.77 (s, 3H), 5.96 (s, 1H), 6.06 (m, 1H), 6.17 (m, 1H); IR (KBr) 2108 s (N$_3$).

Example 26

Preparation of 1,2,3,4-tetrahydro-6-methoxy-1,4-methanonaphthalene-5,8-diol (52)

A solution of 1,4-dihydro-6-methoxy-1,4-methanonaphthalene-5,8-diol (48, 1.30 g, 6.36 mmol) in MeOH (100 mL) was hydrogenated (Parr hydrogenator, 20 psi) over Pd (10% on C, 100 mg, Aldrich) for 15 min. TLC analysis (10% EtOAc, 90% CHCl$_3$) indicated total consumption of the organic starting material to give a higher R$_f$ product. The catalyst was removed by filtration through celite during which time the filtrate turned light green. Color change was attributed to trace air oxidation of the desired product to the corresponding quinone. After MeOH removal, the residue was filtered through silica gel with CHCl$_3$ elution. Solvent removal yielded 52 as a brown gummy solid, which was found suitable for the next reaction without further purification (1.28 g, 98%, purity >95% by TLC and $^1$H NMR analyses); $^1$H NMR (CDCl$_3$) δ1.20 (m, 2H), 1.49

(d, J=8.7 Hz, 1H), 1.70 (m, 1H), 1.88 (m, 2H), 3.42 (s, 1H), 3.62 (s, 1H), 3.80 (s, 3H), 4.37 (s, 1H), 5.17 (s, 1H), 6.19 (s, 1H).

Example 27

Preparation of 1,2,3,4-Tetrahydro-6-methoxy-1,4-methanonaphthalene-5,8-dione (53)

To a vigorously stirred solution of $NaIO_4$ (1.69 g, 7.89 mmol, Baker) in water (50 mL), there was added a solution of 1,2,3,4-tetrahydro-6-methoxy-1,4-methanonaphthalene-5,8-diol (52, 543 mg, 2.63 mmol) in $CHCl_3$ (20 mL). The vigorously stirred reaction immediately became orange. The reaction was allowed to stir for 15 min at rt at which point TLC analysis (10% EtOAc, 90% $CHCl_3$) showed the total consumption of the organic starting material and the formation of a yellow, higher $R_f$ spot. The layers were separated and the aqueous portion extracted with $CHCl_3$ (2×20 mL). The combined organic portion was washed with half saturated brine (30 mL), filtered through cotton and the solvent removed in vacuo. The residue was filtered through a plug of silica gel with $CHCl_3$ elution. Solvent removal gave 53 as a yellow semisolid. Scraping this semisolid with a spatula resulted in a yellow powder. This was further dried in vacuo (470 mg, 88%, pure by TLC and $^1H$ NMR); mp 106°–108° C.; $^1H$ NMR ($CDCl_3$) δ1.16 (m, 2H), 1.40 (d, J=9.0 Hz, 1H), 1.63 (d, J=8.7 Hz, 1H), 1.91 (m, 2H), 3.50 (m, 2H), 3.78 (s, 3H), 5.72 (s, 1H).

Example 28

Preparation of 6,9-methano-3-methoxy-6,7,8,9-tetrahydro-1H-1-benzazepine-2,5-dione To stirred, ice bath cold, concd $H_2SO_4$ (40 mL, Baker), there was added 1,4-methano-6-methoxy-1,2,3,4-tetrahydronaphthalene-5,8-dione (2.47 g, 12.1 mmol) in portions. A deep purple solution resulted. To this cold solution, $NaN_3$ (3.15 g, 48.4 mmol, Aldrich) was added in portions over one min. Vigorous foaming was noted during this addition which was controlled by rapid magnetic stirring. The reaction was allowed to stir in the cold bath for one min after azide addition. The reaction was added to crushed ice (300 mL) to give a brown solution. This was extracted with $CHCl_3$ (3×100 mL). The extract was washed with water (1×100 mL), saturated $NaHCO_3$ (1×100 mL) and brine (1×100 mL), filtered through cotton and the solvent removed in vacuo to give a green solid (285 mg). Trituration with acetone (2 mL) gave a yellow solid, which was collected, washed with acetone (2×1 mL) and hexanes (2×1 mL) and dried in vacuo to give a yellow powder (78 mg, 2.9%, >90% pure by $^1H$ NMR). A second reaction, starting from 1.64 g of quinone gave 60 mg (3.4%) of similar material. The combined reaction products were crystallized from 95% EtOH (dissolved in 15 mL, hot filtered, concd to 10 mL, allowed to cool to rt) to give a near colorless granular solid (64 mg, 1.6% for the two reactions, >95% pure by $^1H$ NMR); mp 285°–287° C.; $^1H$ NMR ($CDCl_3$) δ1.35 (m, 2H), 1.71 (m, 1H), 1.93 (m, 3H), 3.08 (m, 1H), 3.60 (m, 1H), 3.83 (s, 3H), 6.43 (s, 1H), 9.08 (s, 1H); IR (KBr) 2924 (m), 2869 (m), 1691 (m), 1607 (s), 1545 (s), 990 (m); MS (m/z) 219 ($M^+$, 60), 191 ($M^+$–28 (CO), 100).

Example 29

Preparation of 3-hydroxy-6,9-methano-6,7,8,9-tetrahydro-1H-1-benzazepine-2,5-dione (70)

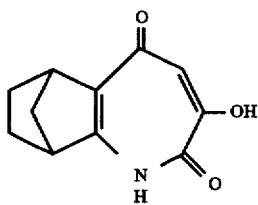

To a stirred suspension of 6,9-methano-3-methoxy-6,7,8,9-tetrahydro-1H-1-benzazepine-2,5-dione (65.0 mg, 296 μmol) in dry $CH_2Cl_2$ (2 mL, distilled from CaH2) under $N_2$, there was added a solution of $BBr_3$ in $CH_2Cl_2$ (1.0 mL, 1M, Aldrich) in one portion over 5 seconds at rt. The suspension immediately yellowed. The reaction was allowed to stir under $N_2$ at rt for 45 min. The reaction was added to saturated $NaHCO_3$ (10 mL) and the resulting pale yellow suspension was vigorously stirred for 15 min to give a pale yellow solution. The solution was washed with $CH_2Cl_2$ (2×4 mL) to remove aqueous base insoluble impurities. The aqueous portion was filtered through glass wool and acidified with concd HCl (pH 2). The resulting precipitate was collected by filtration, washed to neutrality with water (6×2 mL) and air dried to yield a colorless powder (46 mg). Crystallization from 95% EtOH (dissolved in 15 mL, hot filtered, concd to 8 mL, allowed to cool to rt) yielded a near colorless granular solid (32 mg, 52%, pure by $^1H$ NMR); mp 268°–270° C. (dec.); $^1H$ NMR (DMSO-$d_6$) δ1.06 (m, 1H), 1.92 (m, 2H), 1.49 (d, J=8.4 Hz, 1H), 1.79 (m, 2H), 3.21 (m, 1H), 3.31, (m, 1H), 6.26 (s, 1H), 10.03 (bs, 1H), 11.89 (bs, 1H); IR (KBr) 3310 (m), 1665 (m), 1623 (m), 1603 (m), 1542 (s), 1222 (m); Anal. Calcd for $C_{11}H_{11}NO_3$: C, 64.38, H, 5.40, N, 6.83. Found: C, 64.34; H, 5.17; N, 6.81.

Example 30

Preparation of 2-Methoxy-4a,5 8,8a-tetrahydronaphthalene-1,4-dione (55)

A suspension of 2-methoxybenzoquinone (17, 750 mg, 5.43 mmol, TCI, used as received), hydroquinone (38 mg, Matheson, used as received) in toluene (7.5 mL) and butadiene (54, 7.5 mL, Matheson, used as received; Note: condensed butadiene into the toluene with ice bath cooling) contained in a screw top, sealed tube (Ace) was stirred overnight in a 60° C. oil bath. The resulting solution was allowed to cool to rt, then was further cooled in an ice bath. A precipitate formed. The sealed tube was opened. The solid was collected by filtration, washed with hexanes and allowed to air dry (930 mg). The solid was crystallized from hexanes (dissolved in 350 mL, hot filtered, concd to 200 mL, re-filtered, allowed to cool to rt) to yield a yellow powder (703 mg, 68%, >95% pure by $^1H$ NMR analysis); mp 120°–122° C. (hexanes), lit. (Cavill et al., Aust. J. Chem. 26:595–601 (1993)) 126.5°–128° C. (ether); $^1H$ NMR ($CDCl_3$) δ2.21 (m, 2H), 2.51 (m, 2H), 3.16 (m, 1H), 3.26 (m, 1H), 3.79 (s, 3H), 5.69 (m, 2H), 5.90 (s, 1H).

Example 31

Preparation of 2-Methoxy-5,8-dihydronaphthalene-1,4-diol (56)

A solution of 2-methoxy-4a,5,8,8a-tetrahydronaphthalene-1,4-dione (55, 542 mg, 2.82 mmol) in MeOH (50 mL) was purged with a stream of $N_2$ for 5 min with stirring at rt. With continued $N_2$ purging, solid $K_2CO_3$ (390 mg, 2.82 mmol, Baker) was added to the stirred solution. The solution immediately turned yellow. The reaction was allowed to stir for 15 min at rt under $N_2$, after which it was brown. To this there was added a dilute HCl solution (10% concd HCl, 90% $H_2O$, 50 mL) in one portion. The MeOH was removed in vacuo to give a colorless suspension. The suspended material was collected by filtration, washed with a dilute acid solution (as above, 4×6 mL) and dried in vacuo to yield a fluffy colorless solid (444 mg, 82%, pure by $^1H$ NMR analysis (unstable on TLC)); mp 142.5°–144° C. (confirmed), lit. (Cavill et al., supra) 123°–124° C. (benzene/petroleum ether);

$^1H$ NMR (CDCl$_3$) $\delta_{2.21}$ (m, 2H), 3.32 (m, 2H), 3.84 (s, 3H), 4.25 (s, 1H), 5.25 (s, 1H), 5.90 (m, 2H), 6.36 (s, 1H).

Example 32

Preparation of 2-Methoxy-5,6,7,8-tetrahydronaphthalene-1,4-dione (58)

A solution of 2-methoxy-5,8-dihydronaphthalene-1,4-diol (56) in MeOH was hydrogenated over Pd/C (43 mg, 10%, Aldrich) at 20 psi for 30 min at rt in a Parr hydrogenator. The catalyst was removed by filtration (celite) and the solvent removed in vacuo to yield a beige solid (436 mg, ~100%). Analysis ($^1H$ NMR) showed the solid to be a mixture of 58 (13%), the corresponding diol (57, 82%) and 2-methoxynaphthalene-1,4-dione (59, 5%). Without purification, the mixture was dissolved in CHCl$_3$ (35 mL) and the resulting solution vigorously stirred with a solution of NaIO$_4$ (1.42 g, 6.63 mmol, Baker) in $H_2O$ (50 mL) for 20 min at rt. The layers were separated and the aqueous portion extracted with CHCl$_3$ (20 mL). The combined organic portion was washed with 50% saturated brine (20 mL), filtered through a cotton plug and the solvent removed in vacuo to yield a bright yellow solid. Crystallization from 95% EtOH (dissolved in 17 mL, hot filtered, allowed to cool to rt) yielded brilliant yellow plates (280 mg, 66%, >95% pure by $^1H$ NMR with the impurity being 59); mp 167.5°–168.5 (EtOH), lit. (Cunningham et al., *J. Chem. Soc.* 2875–2883 (1963)) 172° C. (MeOH); $^1H$ NMR (CDCl$_3$) $\delta$1.69 (m, 4H), 2.43 (m, 4H), 3.79 (s, 3H), 5.85 (s, 1H).

Example 33

Preparation of 3-Methoxy-6,7,8,9-tetrahydro-1H-1-benzazepine-2,5-dione (60)

To stirred, ice bath cold, concd $H_2SO_4$ (10 mL, Baker), there was added 2-methoxy-5,6,7,8-tetrahydronaphthalene-1,4-dione (600 mg, 3.12 mmol) in portions. A deep red solution resulted. To this cold solution, NaN$_3$ (406 mg, 6.24 mmol, Aldrich) was added in portions. The reaction was allowed to slowly attain rt with stirring under $N_2$. Gas evolution was noted. After 16 h, the reaction was judged complete by TLC analysis (10% MeOH/90% CHCl$_3$). The reaction was added to crushed ice (100 mL) to give a yellow/brown solution. This was extracted with 30% MeOH/70% CHCl$_3$ (4×30 mL) and CHCl$_3$ (2×30 mL). The extract was washed with water (1×20 mL), saturated NaHCO$_3$ (1×20 mL) and brine (1×20 mL), filtered through cotton and the solvent removed in vacuo to give a red solid (280 mg). An additional portion was obtained in exactly the same manner (350 mg). The combined solids were subjected to vacuum chromatography (silica gel, 2.5×25 cm, initial CHCl$_3$ elution to remove mobile impurities, 2% EtOH/98% CHCl$_3$ elution to remove product) to yield a pink solid. Crystallization from 95% EtOH (dissolved in 20 mL, hot filtered, concd to 8 mL, allowed to cool to rt) yielded a pink solid (242 mg, 19%, >95% pure by $^1H$ NMR, mp 227.5°–228.5° C.). A sample was further purified by recrystallization from 95% EtOH (25 mg dissolved in 2 mL, allowed to cool to rt, yielded a pale pink solid, 14 mg, 56% recovery); mp 228.5°–229.5° C.;

$^1H$ NMR (DMSO-d$_6$) $\delta$1.55 (m, 4H), 2.28 (m, 2H), 2.43 (m, 2H), 3.72 (s, 3H), 6.23 (s, 1H), 10.57 (s, 1H); MS m/z 207 (M$^+$, 85).

Example 34

Preparation of 3-Hydroxy-6,7,8,9-tetrahydro-1H-1-benzazepine-2,5-dione (61)

To a stirred suspension of 3-methoxy-6,7,8,9-tetrahydro-1H-1-benzazepine-2,5-dione (207 mg, 1.00 mol) in dry CH$_2$Cl$_2$ (2 mL, distilled from CaH$_2$) under $N_2$, there was added a solution of BBr$_3$ in CH$_2$Cl$_2$ (2.0 mL, 1M, Aldrich) in one portion over 5 seconds at rt. A brown precipitate immediately formed. The reaction was allowed to stir under $N_2$ at rt for 45 min. The reaction was added to saturated NaHCO$_3$ (15 mL) and the resulting orange solution was allowed to stir for 15 min. The solution was extracted with CH$_2$Cl$_2$ (1×4 mL). The aqueous solution was acidified with concd HCl (pH 2), the resulting precipitate collected by filtration and washed to neutrality with water (6×2 mL). Crystallization from 95% EtOH yielded beige flakes (115 mg, 60%, pure by TLC, $^1H$ NMR and C,H,N analysis); mp 237°–238° C. (dec.); $^1H$ NMR (DMSO-d$_6$) $\delta$1.55 (m, 4H), 2.27 (m, 2H), 2.45 (m, 2H), 6.30 (s, 1H), 10.14 (bs, 1H), 10.84 (s, 1H). Anal. Calcd for C$_{10}$H$_{11}$NO$_3$: C, 62.17; H, 5.74; N, 7.25. Found: C, 62.23; H, 5.62; N, 7.26.

Example 35

Preparation of 2-Methoxy-5,8-dihydronaphthalene-1,4-dione (71)

A solution of 2-methoxy-5,8-dihydronaphthalene-1,4-diol (5.70 g, 29.8 mmol) in CHCl$_3$ (350 mL, prepared with warming and allowed to cool to below 35° C.) was added to a vigorously stirred solution of NaIO$_4$ (12.7 g, 59.6 mmol) in $H_2O$ (400 mL) in one portion. The reaction was allowed to vigorously stir for 20 min and the layers were separated. The aqueous portion was extracted with CHCl$_3$ (1×50 mL). The combined CHCl$_3$ portion was washed with brine, filtered through cotton and concentrated in vacuo to approximately 100 mL. The concentrate was filtered through silica gel (2.5×7 cm) with CHCl$_3$ elution (removes dark color), followed by solvent removal in vacuo to give a yellow solid. Trituration with hexanes (20 mL) yielded a brilliant yellow powder (5.55 g, 98%, purity >95% by TLC and $^1H$ NMR); mp 171.5°–172.5° C.; $^1H$ NMR (CDCl$_3$) $\delta$3.08 (m, 4H), 3.81 (s, 3H), 5.81 (s, 2H), 5.89 (s, 1H).

Example 36

Preparation of 2-Methoxy-7,8-dichloro-5,6,7,8-tetrahydronaphthalene-1,4-dione (72)

To a solution of 2-methoxy-5,8-dihydronaphthalene-1,4-dione (2.75 g, 14.4 mmol) in CHCl$_3$ (60 mL, pre-treated with silica gel to remove the EtOH stabilizer) there was added a solution of Cl$_2$ (~1.10 g, ~15.1 mmol) in EtOH-free CHCl$_3$ (50 mL) in portions over 30 min. TLC (5% EtOAc/95% EtOH) indicated total consumption of the starting material and the appearance of a major higher R$_f$ product spot (lower R$_f$ impurity spots were also noted). The solvent was removed in vacuo to yield a yellow syrup. The addition of 95% EtOH (10 mL) followed by evaporation in vacuo (performed twice) yielded a yellow solid. Crystallization from 95% EtOH (dissolved in 20 mL, allowed to cool to rt) yielded a yellow solid (2.28 g, 60%, ~90% pure by TLC and $^1H$ NMR, mp 119°–123° C.). Recrystallization from 95%

EtOH (dissolved in 12 mL, allowed to cool to rt) yielded a yellow crystalline solid (1.89 g, 83% recovery, 50% total yield, ~95% pure by TLC and $^1$H NMR with the major impurity being 2-methoxynaphthalene-1,4-dione); mp 123°–128° C. (EtOH); $^1$H NMR (CDCl$_3$) δ3.11 (m, 4H), 3.83 (s, 3H), 4.67 (m, 2H), 5.94 (s, 1H).

Example 37

Preparation of 3-Methoxy-7,8-dichloro-6,7,8,9-tetrahydro-1H-1-benzazepine-2,5-dione (73)

To stirred, ice bath cold, concd H$_2$SO$_4$ (10 mL, Baker), there was added 2-methoxy-7,8-dichloro-5,6,7,8-tetrahydronaphthalene-1,4-dione (~95%, 600 mg, 3.12 mmol) in portions. A deep red solution resulted. To this cold solution, NaN$_3$ (598 mg, 9.20 mmol, Aldrich) was added in portions. The reaction was allowed to slowly attain rt with stirring under N$_2$. Gas evolution was noted. After 16 h, the reaction was judged complete by TLC analysis (10% MeOH/90% CHCl$_3$). The reaction was added to crushed ice (100 mL) to give a yellow/brown solution. This was extracted with 30% MeOH/70% CHCl$_3$ (4×30 mL) and CHCl$_3$ (2×30 mL). The extract was washed with water (1×20 mL), saturated NaHCO$_3$ (1×20 mL) and brine (1×20 mL), filtered through cotton and the solvent removed in vacuo to give a green solid (115 mg). Trituration with MeOH/ether (1:1, 3 mL) gave a grey solid suspended in a dark solution. The suspended solid was collected, washed with ether and dried in vacuo to give a grey powder (45 mg). Two additional portions were obtained in exactly the same manner (63 and 58 mg). Analysis ($^1$H NMR) of the crude reaction products showed the desired product to be present with a purity of ~75% with the major impurity being 3-methoxy-1H-1-benzazepine-2,5-dione. Purification was effected by crystallization from 95% EtOH. An initial crystallization (165 mg, dissolved in 75 mL, concd to 40 mL) yielded a grey powder (127 mg, 77% recovery, ~90% pure by $^1$H NMR). Recrystallization (125 mg, dissolved in 70 mL, concd to 30 mL, allowed to cool to rt) yielded a near colorless powder (112 mg, 88% recovery, 6% final yield, >95% pure by $^1$H NMR); mp 229°–230° C., $^1$H NMR (DMSO-d$_6$) δ2.67 (dd, J=18.3, 5.4 Hz, 1H), 2.87 (dd, J=18.8, 5.2 Hz, 1H), 3.03 (dd, J=18.3, 4.5 Hz, 1H), 3.22 (dd, J=18.9, 4.8 Hz, 1H), 4.58 (m, 2H), 6.28 (s, 1H), 10.90 (s, 1H).

Example 38

Preparation of 3-Hydroxy-7,8-dichloro-6,7,8,9-tetrahydro-1H-1-benzazepine-2,5-dione (74)

To a stirred suspension of 3-methoxy-7,8-dichloro-6,7,8,9-tetrahydro-1H-1-benzazepine-2,5-dione (100 mg, 362 μmol) in dry CH$_2$Cl$_2$ (2 mL, distilled from CaH$_2$) under N$_2$ there was added a solution of BBr$_3$ in CH$_2$Cl$_2$ (1.0 mL, 1M, Aldrich) in one portion over 5 seconds at rt. A greenish yellow precipitate immediately formed. The reaction was allowed to stir under N$_2$ at rt for 45 min. The reaction was added to saturated NaHCO$_3$ (15 mL) and the resulting beige suspension was allowed to stir for 15 min. The suspension was acidified with concentrated HCl (pH 2), allowed to stir for 15 min at rt, the solid collected by filtration and washed to neutrality with water (6×2 mL). Crystallization from 95% EtOH (dissolved in 75 mL, hot filtered (Whatman #2), concd to 30 mL, allowed to cool to rt) yielded a beige amorphous solid (68 mg, 71%, >98% pure by $^1$H NMR, pure by C,H,N analysis); mp 246°–248° C. (dec.); $^1$H NMR (DMSO-d$_6$) δ2.70 (dd, J=18.2, 5.6 Hz, 1H), 2.91 (dd, J=18.9, 5.4 Hz, 1H), 3.06 (dd, J=18.3, 4.8 Hz, 1H), 3.26 (dd, J=18.8, 4.6 Hz, 1H), 4.57 (m, 2H), 6.34 (s, 1H), 10.46 (s, 1H), 11.11 (s, 1H). Anal. Calcd for: C, 45.83, H, 3.46, N, 5.34. Found: C, 46.02; H, 3.54; N, 5.26.

Example 39

Preparation of 1-(tert-Butyldimethylsilyloxy)-2-methyl-1-aza-1,3-butadiene (75)

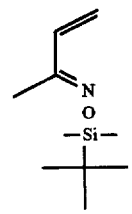

The procedure followed was that described by Behforouz et al., J. Org. Chem. 58:7089–7091 (1993). In a 50 mL round bottom flask, dry 4 Å molecular sieves (Fisher, 3.4 g) were added to dry CH$_2$Cl$_2$ (distilled from CaH$_2$, 10 mL) and cooled to 5° C. with an ice bath. Methyl vinyl ketone (Aldrich, new bottle, used without purification, 0.725 mL, 0.618 g, 3.84 mmol) was added. A solution of O-(tert-butyldimethylsilyl)hydroxylamine (Aldrich, used without purification, 1.0 g, 6.80 mmol) in dry CH$_2$Cl$_2$ (distilled from CaH$_2$, 3 mL) was added dropwise over a period of 5 min. The ice bath was removed and the mixture was stirred at rt under N$_2$ for 18 h. The sieves were removed by filtration and the CH$_2$Cl$_2$ was evaporated to dryness (roto-vap). Column chromatography with silica gel and CHCl$_3$ as eluent afforded 1-(tert-butyldimethylsilyloxy)-2-methyl-1-aza-1,3-butadiene as a light oil (1.2 g, 81%, interpretation of the $^1$H NMR showed a 1:1 anti/syn mixture): $^1$H NMR (CDCl$_3$) δ (anti) 0.17 (s, 6H), 0.94 (s, 9H), 1.97 (s, 3H), 5.35–5.75 (m, 2H), 6.41–6.53 (m, 1H); (syn) 0.17 (s, 6H), 0.94 (s, 9H), 1.99 (s, 3H), 5.35–5.75 (m, 2H), 7.15–7.25 (m, 1H).

Example 40

Preparation of 1-(tert-Butyldimethylsilyloxy)-1-aza-1,3-pentadiene (76)

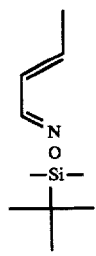

The procedure followed was that described by Behforouz et al., J. Org. Chem. 58:7089–7091 (1993). In a 50 mL round bottom flask dry, 4 Å molecular sieves (Fisher, 3.4 g) were added to dry CH$_2$Cl$_2$ (distilled from CaH$_2$, 10 mL) and cooled to 5° C. with an ice bath. Freshly distilled crotonaldehyde (Matheson Coleman & Bell, 0.725 mL, 0.618 g, 8.84 mmol) was added. A solution of O-(tert-butyldimethylsilyl)hydroxylamine (Aldrich, used without purification, 1.0 g, 6.80 mmol) in dry CH$_2$Cl$_2$ (distilled from CaH$_2$, 3 mL) was added dropwise over a period of 5 min. The ice bath was removed and the mixture was stirred at rt under N$_2$ for 18 h. The sieves were removed by filtration and the CH$_2$Cl$_2$ was evaporated to dryness (roto-vap). Column chromatography on silica gel with CHCl₃ as eluent afforded 1-(tert-butyldimethylsilyloxy)-1-aza-1,3-pentadiene as a colorless light oil (1.2 g, 88%, interpretation of the ¹H NMR showed a 1:1 anti/syn mixture): ¹H NMR (CDCl₃) δ (anti) 0.18 (s, 6H), 0.95 (s, 9H), 1.85–1.88 (m, 3H), 5.93–6.23 (m, 1H), 6.7–6.9 (m, 1H), 7.18 (d, 1H); (syn) 0.18 (s, 6H), 0.95 (s, 9H), 1.85–1.88 (m, 3H), 5.93–6.15 (m, 2H), 7.81 (d, 1H).

Example 41

Preparation of 6,7-dimethyl-2-methoxy-4a,5,8,8a-tetrahydronaphthalene-1,4-dione (77)

To a vigorously stirred solution of NaIO₄ (33.5 g, 157 mmol, Baker) in H₂O (1500 mL), there was added solid 2-methoxyhydroquinone (11.00 g, 50.0 mmol) in portions. The reaction immediately became dark orange. The reaction was allowed to stir for 1 h at rt and was extracted with CH₂Cl₂ (3×150 mL). The extract was washed with half saturated brine (1×150 mL), filtered through cotton and the solvent removed in vacuo to yield 2-methoxybenzoquinone as an orange solid (10.5 g) which was of sufficient purity (TLC analysis, 10% EtOAc/90% CHCl₃) for further reaction. The crude quinone was combined with toluene (150 mL) and hydroquinone (1.0 g, Mallinkrodt). Neat 2,3-dimethyl-1,3-butadiene (8.3 g, 101 mmol, Aldrich) was added. The reaction was allowed to stir overnight at 65° C. under N₂. TLC (10% EtOAc/90% CHCl₃) indicated total consumption of the dienophile. The solvent was removed in vacuo to yield a dark solid. This was triturated with MeOH (100 mL) at n to give a beige solid. Crystallization from MeOH (dissolved in 140 mL, allowed to cool to rt) yielded a fluffy colorless solid (10.2 g, 64%, >95% pure by ¹H NMR analysis); mp 133°–134° C. (MeOH); ¹H NMR (CDCl₃) δ1.62 (s, 6H), 2.12 (m, 2H), 2.42 (m, 2H), 3.09 (m, 1H), 3.20 (m, 1H), 3.78 (s, 3H), 5.88 (s, 1H).

Example 42

Preparation of 5,8-dihydro-6,7-dimethyl-2-methoxynaphthalene-1,4-diol (78)

A solution of 6,7-dimethyl-2-methoxy-4a,5,8,8a-tetrahydronaphthalene-1,4-dione (4.0 g, 18.2 mmol) in MeOH (600 mL) was purged with a stream of N₂ for 10 min with stirring at rt. With continued N₂ purging, solid K₂CO₃ (2.51 g, 18.2 mmol, Baker) was added to the stirred solution. The solution immediately turned yellow. The reaction was allowed to stir for 30 min at rt under N₂, after which it was brown. To this there was added a dilute HCl solution (10% concd HCl, 90% H₂O, 200 mL) in one portion. The MeOH was removed in vacuo to give a colorless suspension. The suspension was cooled in an ice bath for 20 min. The suspended material was collected by filtration, washed with a dilute acid solution (as above, 3×20 mL) and dried in vacuo to yield a fluffy colorless solid (3.90 g, 98%, pure by ¹H NMR analysis (unstable on TLC)); mp 200°–201° C.; ¹H NMR (CDCl₃) δ1.79 (s, 6H), 3.12 (m, 2H), 3.25 (m, 2H), 3.83 (s, 3H), 4.25 (s, 1H), 5.25 (s, 1H), 6.35 (s, 1H).

Example 43

Preparation of 6,7-dimethyl-2-methoxy-5,6,7,8-tetrahydronaphthalene-1,4-dione (79)

A solution of 5,8-dihydro-6,7-dimethyl-2-methoxynaphthalene-1,4-diol (2.00 g, 9.08 mmol) in MeOH (250 mL) was hydrogenated over Pd/C (200 mg, 10%, Aldrich) at 30–40 psi for 24 h at rt in a Parr hydrogenator. The catalyst was removed by filtration (Celite) and the solvent removed in vacuo to yield a brown tacky solid (~2.2 g, ~100%). Analysis (¹H NMR) showed the solid to be a mixture of reduced diol (90%) and 2-methoxy-6,7-dimethhylnaphthalene-1,4-dione. Without purification, the mixture was dissolved in CHCl₃ (100 mL) and the resulting solution vigorously stirred with a solution of NaIO₄ (3.89 g, 18.2 mmol, Baker) in H₂O (200 mL) for 30 min at rt. The layers were separated and the aqueous portion extracted with CHCl₃ (1×30 mL). The combined organic portion was washed with saturated brine (1×30 mL), filtered through a cotton plug and the solution concentrated in vacuo to yield a brown concentrate. The concentrate was passed through a silica gel column (2.5×17 cm) with CHCl₃ elution to give an initial yellow band, which contained the desired product. Solvent removal in vacuo yield a brown oil (1.3 g). This material was further purified on a silica gel column (2.5×25 cm) to yield an orange viscous oil from the initial band (787 mg, 39%, pure by TLC and ¹H NMR, as a probable mixture of cis- and trans-isomers (85 to 15)); ¹H NMR (CDCl₃) δ0.88 (d, J=6.6 Hz, 6H), 1.90 (m, 2H), 2.20 (m, 2H), 2.50 (m, 2H), 3.79 (s, 3H), 5.85 (s, 1H). The minor isomer shows a doublet at 1.03, J=6.0 Hz.

Example 44

Preparation of 7,8-dimethyl-3-methoxy-6,7,8,9-tetrahydro-1H-1-benzazepine-2,5-dione (80)

To stirred, ice cold, concd H₂SO₄ (10 mL, Baker) there was added, in a dropwise manner, a solution of 6,7-dimethyl-2-methoxy-5,6,7,8-tetrahydronaphthalene-1,4-dione (560 mg, 2.54 mmol) in neat TFA (2 mL, Aldrich). To the resulting deep red solution, there was added NaN₃ (330 mg, 5.08 mmol, Aldrich) in portions with stirring. The ice bath was removed and the reaction was allowed to stir at rt under N₂. Gas evolution was noted within a few minutes of ice bath removal. After 60 min, analysis (TLC, 3% EtOAc/97%CHCl₃) indicated total consumption of the quinone. Further analysis (TLC, 10% MeOH/90% CHCl₃) indicated the formation of one major product. The reaction was added to ice H₂O (50 mL) and extracted with 30% MeOH/70% CHCl₃ (3×30 mL). The extract was washed with H₂O, saturated NaHCO₃ and H₂O (1×30 mL each), filtered through a cotton plug and the solvent removed in vacuo to give a dark solid (400 mg). This was purified chromatographically on silica gel (2.5×25 cm) with CHCl₃ elution to yield a beige solid (178 mg, 30% mass recovery). Crystallization from 95% EtOH (dissolved in 15 mL, hot filtered, concd to 5 mL, allowed to cool to rt) yielded a brown granular solid (98 mg, 16%, pure by TLC, >98% pure by ¹H NMR, consists of a probable mixture of cis- and trans-isomers (85:15)); mp 232.5–235.5; ¹H NMR (CDCl₃) δ0.91 (m, 6H), 1.82–2.63 (m, 6H), 3.84 (s, 3H), 6.38 (s, 1H), 7.96 (bs, 1H). The minor isomer shows a multiplet for the methyl groups at 1.02 ppm. IR (KBr) 2973 (s), 1685 (s), 1615 (s), 1545 (s); MS (m/z) 235 (M⁺, 45), 220 (M⁺15 (CH₃), 65), 207 (M⁺–28 (CO), 35), 192 (M⁺–43 (CH₃, CO), 100).

Example 45

Preparation of 7,8-dimethyl-3-hydroxy-6,7,8,9-tetrahydro-1H-1-benzazepine-2,5-dione (81)

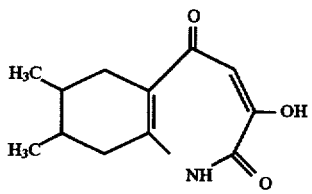

To a stirred suspension of 7,8-dimethyl-3-methoxy-6,7,8, 9-tetrahydro-1H-1-benzazepine-2,5-dione (90.0 mg, 382 μmol) in dry CH₂Cl₂ (2 mL, distilled from CaH₂) under N₂, there was added a solution of BBr₃ in CH₂Cl₂ (1.0 mL, 1M, Aldrich) in one portion over 5 seconds at rt. A green precipitate immediately formed. The reaction was allowed to stir under N₂ at rt for 45 min. The reaction was added to saturated NaHCO₃ (15 mL) and the resulting orange solution was allowed to stir for 15 min. The solution was extracted with CH₂Cl₂ (2×4 mL). The aqueous solution was acidified with concd HCl (pH 2), the resulting precipitate collected by filtration and washed to neutrality with water (6×2 mL). Crystallization from 95% EtOH yielded pale beige needles (56 mg, 67%, pure by ¹H NMR, consists of a probable mixture of cis- and trans-isomers (85:15)); mp 242°–243° C. (dec.);

¹H NMR (DMSO-d₆) δ0.80 (t, J=7.5 Hz, 6H), 1.79 (m, 2H), 2.03 (dd, J=7.5, 17.7 Hz, 1H), 2.21 (dd, J=6.0, 18.0 Hz, 1H), 2.35 (dd, J=5.1, 17.7 Hz, 1H), 2.58, (dd, J=5.4, 18.0 Hz, 1H), 6.29 (s, 1H), 10.15 (bs, 1H), 10.82 (s, 1H), the minor isomer displays a methyl resonance at δ 0.92 (t, J=5.7 Hz); IR (KBr) 3314 (m), 1676 (m), 1664 (m), 1613 (m), 1550 (s), Anal. Calcd for C₁₂H₁₅NO₃: C, 65.14, H, 6.83, N, 6.33. Found: C, 65.47; H, 6.87; N, 6.32.

Example 46

Preparation of 1,4-ethano-6-methoxy-1,4,4a,8a-tetrahydronaphthalene-5,8-dione (82)

To a stirred suspension of 2-methoxybenzoquinone (2.5 g, 18.1 mmol) in toluene (50 mL) there was added hydroquinone (250 mg, Mallinkrodt) and 1,3-cyclohexadiene (2.17 g, 27.1 mmol, Aldrich, 97%). The reaction was stirred in a 60° C. oil bath for 22 h under N₂. Analysis (TLC, 3% EtOAc/97% CHCl₃) indicated partial reaction. The oil bath temperature was raised to 100° C. and the reaction was allowed to proceed an additional 24 h. The analysis now showed total conversion the quinone to a lower R_f product. The solvent was removed in vacuo to give a brown solid (~4 g). Crystallization from MeOH (dissolved in 30 mL, decolorized with activated charcoal (3 spatula tips), hot filtered (Whatmann #2), allowed to cool to rt then placed in a cold room) yielded a pale yellow crystalline solid (2.12 g, 54%, pure by TLC and ¹H NMR); mp 128–130; ¹H NMR (CDCl₃) δ1.36 (m, 2H), 1.70 (m, 2H), 2.98 (m, 2H), 3.23 (m, 2H), 3.72 (s, 3H), 5.96 (s, 1H), 6.20 (m, 2H); IR (KBr) 2948 (m), 1681 (s), 1644 (s), 1616 (s), 1461 (m), 1370 (m), 1170 (m).

Example 47

Preparation of 1,4-dihydro-1,4-ethano-6-methoxynaphthalene-5,8-diol (83)

A solution of 1,4-ethano-6-methoxy-1,4,4a,8a-tetrahydronaphthalene-5,8-dione (2.10 g, 9.62 mmol) in MeOH (100 mL) was purged with a stream of N₂ for 10 min with stirring at rt. With continued N₂ purging, solid K₂CO₃ (1.33 g, 9.62 mmol, Baker) was added to the stirred solution. The solution immediately turned yellow. The reaction was allowed to stir for 30 min at rt under N₂, after which it was greenish yellow. To this there was added a dilute HCl solution (10% concd HCl, 90% H₂O, 100 mL) in one portion. The MeOH was removed in vacuo to give a colorless suspension. This was cooled in an ice bath for 2 hr. The suspended material was collected by filtration, washed with a dilute acid solution (as above, 3×10 mL) and dried in vacuo to yield a colorless solid (2.05 g, 98%, pure by ¹H NMR analysis); mp 112°–115° C.; ¹H NMR (CDCl₃) δ1.47 (m, 4H), 3.79 (s, 3H), 4.14 (m, 1H), 4.37 (m, 1H), 5.21 (bs, 1H), 6.21 (s, 1H), 6.50 (m, 2H), Note: one hydroxyl proton was very broad and its chemical shift could not be ascertained; IR (KBr) 3403 (s), 3247 (s), 1500 (m).

Example 48

Preparation of 1,4-Ethano-6-methoxy-1,2,3,4-tetrahydronaphthalene-5,8-diol (84)

A solution of 1,4-dihydro-6-methoxy-1,4-ethanonaphthalene-5,8-diol (2.05 g, 9.39 mmol) in MeOH (100 mL) was hydrogenated (Parr hydrogenator, 20–30 psi) over Pd (10% on C, 200 mg, Aldrich) for 30 min. The catalyst was removed by filtration through celite during which time the filtrate turned light yellow. The color change was attributed to trace air oxidation of the desired product to the corresponding quinone. Solvent removal yielded a brown gummy solid, which was found suitable for the next reaction without further purification (2.1 g, 100%, purity >95% by ¹H NMR); ¹H NMR (CDCl₃) δ1.37 (d, J=9.3 Hz, 4H), 1.75 (d, J=8.7 Hz, 4H), 3.15 (m, 1H), 3.45 (m, 1H), 3.83 (s, 3H), 4.43 (bs, 1H), 5.21 (bs, 1H), 6.34 (s, 1H).

Example 49

Preparation of 1,4-Ethano-6-methoxy-1,2,3,4-tetrahydronaphthalene-5,8-dione (85)

To a vigorously stirred solution of NaIO₄ (4.02 g, 18.8 mmol, Baker) in water (100 mL), there was added a solution of 1,4-ethano-6-methoxy-1,2,3,4-tetrahydronaphthalene-5, 8-diol (2.1 g, 9.4 mmol) in CHCl₃ (50 mL). The vigorously stirred reaction immediately became orange. The reaction was allowed to stir for 20 min at rt. The layers were separated and the aqueous portion extracted with CHCl₃ (1×20 mL). The combined organic portion was washed with saturated brine (20 mL), filtered through cotton and the solvent removed in vacuo. The residue was filtered through a plug of silica gel (20×2.5 cm) with CHCl₃ elution. Solvent removal gave a yellow/orange solid. Trituration with ether/hexanes (1:3, 4 mL) resulted in a yellow powder, which was collected, washed with hexanes (3×2 mL) and dried in vacuo (1.71 g, 83%, pure by TLC and ¹H NMR); mp 144°–145° C.;

¹H NMR (CDCl₃) δ1.27 (d, J=7.2 Hz, 4H), 1.71 (d, J=7.5 Hz, 4H), 3.33 (m, 1H), 3.37 (m, 1H), 3.80 (s, 3H), 5.82 (s, 1H); IR (KBr) 2959 (m), 2870 (m), 1667 (s), 1641 (s), 1592 (s), 1229 (s).

Example 50

Preparation of 6,9-Ethano-3-methoxy-6,7,8,9-tetrahydro-1H-1-benzazepine-2,5-dione (86)

To stirred, ice bath cold, concd H₂SO₄ (22 mL, Baker), there was added 1,4-ethano-6-methoxy-1,2,3,4-tetrahydronaphthalene-5,8-dione (1.40 g, 6.41 mmol) in portions. A burgundy solution resulted. To this cold solution, NaN₃ (833 mg, 12.8 mmol, Aldrich) was added in portions over one min. The ice bath was removed and the reaction was allowed to stir at rt for 1h under N₂. Nitrogen evolution was noted. The reaction color changed to grey during this period. The reaction was added to crushed ice (150 mL) to give a red solution. This was extracted with CHCl₃ (3×50 mL). The extract was washed with water (1×50 mL), saturated NaHCO₃ (1×50 mL) and brine (1×50 mL), filtered through cotton and the solvent removed in vacuo to give a yellow solid (940 mg). Crystallization from 95% EtOH (dissolved in 40 mL, hot filtered, concd to 25 mL, allowed to cool to rt) gave very pale yellow flakes (471 mg, 31%, >95% pure by ¹H NMR); mp 276°–278° C.; ¹H NMR (CDCl₃) δ1.35 (m, 2H), 1.55 (m, 2H), 1.69 (m, 4H), 2.57 (m, 1H), 3.65 (m, 1H), 3.84 (s, 3H), 6.46 (s, 1H), 8.67 (bs, 1H); IR (KBr) 3211 (m), 3096 (m), 2944 (m), 1691 (s), 1610 (s), 1545 (s), 888 (m); MS (m/z) 233 (M⁺, 25), 205 (M⁺–28 (CO or C₂H₄), 100), 177 (M⁺–56 (CO and C₂H₄), 40).

Example 51

Preparation of 6,9-Ethano-3-hydroxy-6,7,8,9-tetrahydro-1H-1-benzazepine-2,5-dione (87)

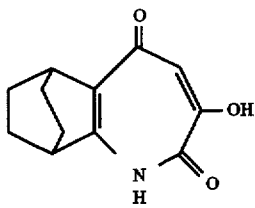

To a stirred suspension of 6,9-ethano-3-methoxy-6,7,8,9-tetrahydro-1H-1-benzazepine-2,5-dione (350 mg, 1.50 mmol) in dry CH₂Cl₂ (3.5 mL, distilled from CaH2) under N₂, there was added a solution of BBr₃ in CH₂Cl₂ (3.5 mL, 1M, Aldrich) in one portion over 5 seconds at rt. The suspension immediately yellowed. The reaction was allowed to stir under N₂ at rt for 45 min. The reaction was added to saturated NaHCO₃ (45 mL) and the resulting pale yellow suspension was vigorously stirred for 15 min to give a pale yellow solution. The solution was washed with CH₂Cl₂ (3×4 mL) to remove aqueous base insoluble impurities. The aqueous portion was filtered through glass wool and acidified with concd HCl (pH 2). The resulting precipitate was collected by filtration, washed to neutrality with water (6×2 mL) and air dried to yield a colorless powder (290 mg). Crystallization from 95% EtOH (dissolved in 15 mL, hot filtered, concd to 10 mL, allowed to cool to rt) yielded colorless, fine needles (169 mg, 49%, pure by ¹H NMR); mp 252°–254° C. (dec.); ¹H NMR (DMSO-d₆) δ1.43 (m, 2H), 1.37 (m, 2H), 1.57 (m, 4H), 2.96 (m, 1H), 3.46 (m, 1H), 6.35 (s, 1H), 10.04 (bs, 1H), 11.46 (bs, 1H); IR (KBr) 3328 (m), 1663 (m), 1631 (m), 1606 (m), 1540 (s), 1231 (m); Anal. Calcd for C₁₂H₁₃NO₃: C, 65.74, H, 5.98, N, 6.39. Found: C, 65.38; H, 5.79; N, 6.27.

Example 52

Preparation of 2-Bromo-5-methoxyhydroquinone (88)

To a stirred, water bath cooled (15°–20° C.) solution of 2-methoxyhydroquinone (20.0 g, 143 mmol) in glacial AcOH (400 mL) there was added in a drop wise manner, neat bromine (23.3 g, 7.5 mL, 146 mmol, Baker) over a period of 20 min. The color of the reaction mixture darkened during the addition. Analysis (TLC) of the reaction mixture immediately after addition indicated complete consumption of the starting material and the formation of one major higher R_f spot and one minor higher R_f spot. The solvent was removed in vacuo at 35° C. to give a dark brown solid. The solid was dissolved in hot CHCl₃ (400 mL) and the resulting solution was filtered through a pad of silica gel (8×8 cm). The product was eluted from the silica gel with CHCl₃. Solvent removal gave a brown solid. Crystallization from benzene (dissolved in 225 mL, hot filtered (glass wool) and allowed to cool to rt) yielded brown/purple needles (24.5 g, 78%); mp 127°–127.5° C. (This compound was reported by Murphy, W. S.; O'Sullivan, R. J., Tetrahedron Lett. 33:531–534 (1992) but no analytical data was given.); ¹H NMR (CDCl₃) δ3.96 (s, 3H), 5.12 (bs, 1H), 5.23 Cos, 1H), 6.60 (s, 1H), 7.00 (s, 1H); IR (KBr) 3287 (s), 2932, (w), 1614 (m), 1513 (s), 820 (s).

Example 53

Preparation of 2-Bromo-5-methoxybenzoquinone (89)

To a vigorously stirred solution of NaIO₄ (7.81 g, 36.5 mmol, Baker) in H₂O (200 mL) there was added a solution of 2-bromo-5-methoxyhydroquinone (4.00 g, 18.3 mmol) in CHCl₃ (150 mL, prepared with warming). The reaction immediately turned dark and then became orange over a period of time. The reaction was allowed to stir at rt for 30 min. The layers were separated and the aqueous portion extracted with CHCl₃ (1×30 mL). The combined CHCl₃ portion was washed with brine (1×30 mL), filtered through cotton, and the solvent removed in vacuo to give a mustard yellow solid (4.0 g, 100%, pure by TLC); mp 184°–186° C. Crystallization of a 50 mg sample from MeOH (dissolved in 5 mL of MeOH, allowed to cool to rt) yielded orange needles (43 mg, 86% recovery); mp 186°–187° C., lit 190°–191° C. (Blatchly, J. M.; Green, R. J. S.; McOmie, J. F. W.; Searle, J. B. J. Chem. Soc. (C),1353–1355 (1969)); ¹H NMR (CDCl₃) δ3.86 (s, 3H), 6.12 (s, 1H), 7.24 (s, 1H); IR (KBr) 3044 (m), 1669 (s), 1649 (s), 1623 (s), 1584 (s), 1197 (s), 1169 (s).

Example 54

Preparation of 5,8-Dihydro-2-methoxy-5-methylnaphthalene-1,4-dione (90)

To a stirred suspension of 2-bromo-5-methoxybenzoquinone (4.0 g, 18 mmol) in toluene (100 mL) there was added trans-piperylene (5.46 mL, 3.73 g, 47 mmol, Aldrich, 90%) in one portion. The reaction mixture was allowed to stir in a 60°–70° C. oil bath for 4 days. A homogeneous solution was present. The status of the reaction was determined by ¹H NMR. Since the adduct was not stable once the reaction solvent was evaporated, an aliquot was diluted in half with MeOH and treated with an excess of Et₃N. After one min, dilute HCl (10% concd HCl/90% H₂O) was added and the mixture extracted with CHCl₃. The extract was washed with H₂O, filtered through cotton and the solvent removed in vacuo. The ¹H NMR was then determined in CDCl₃. The absence of a resonance at 7.24 ppm indicated that the starting quinone was totally consumed. The remaining reaction mixture was allowed to cool to rt and was diluted in half with MeOH. The reaction was purged with N₂ for 5 min with stirring and Et₃N (3.69 g, 36.5 mmol, EM) was added. The reaction mixture darkened. The reaction was allowed to stir for 5 min under N₂. Dilute HCl (vide supra, 150 mL) was then vigorously stirred in to give a lighter yellow/orange mixture. The layers were separated and the aqueous extracted with toluene (1×30 mL). The combined toluene portion was washed with H₂O and brine (30 mL each), filtered through cotton and the solvent removed in vacuo to give an orange solid (4.2 g). Crystallization from 95% EtOH (dissolved in 25 mL boiling solvent, hot filtered, allowed to cool to rt, cooled in a cold room) yielded an orange crystalline solid (2.87 g, 77% for the two steps, pure by TLC and ¹H NMR); mp 115.5–116.5 (compound reported by Tegmo-Larsson, I. M.; Rozeboom, M. D.; Houk, K. N., Tetrahedron Lett. 22:2043–2046 (1981), but no analytical data was reported); ¹H NMR δ1.17 (d, J=6.9 Hz, 3H), 2.94 (m, 1H), 3.15 (m, 1H), 3.44 (m, 1H), 3.80 (s, 3H), 5.77 (m, 2H), 5.88 (s, 1H); IR (KBr) 3056 (w), 3033 (w), 2973 (w), 1667 (s), 1634 (s), 1602 (s), 1218 (s), 1018 (m), 976 (m), 871 (m), 717 (m).

Example 55

Preparation of 2-Methoxy-5-methylnaphthalene-1,4-dione (91)

To a solution of 5,8-dihydro-2-methoxy-5-methylnaphthalene-1,4-dione (100 mg, 490 µmol) in CHCl$_3$ (5 mL), there was added MnO$_2$ (213 mg, 2.45 mmol, Fluka). The stirred suspension was heated at reflux for 45 min (progress of the reaction may best be monitored by $^1$H NMR since TLC gives ambiguous results). The reaction was allowed to cool to rt and was filtered through a pad of Celite (the pad was washed with CHCl$_3$ (3×3 mL)). Solvent removal yielded a yellow powder (99 mg, 100%, pure by TLC and $^1$H NMR); mp 138.5°–140° C.; $^1$H NMR δ (CDCl$_3$) 2.76 (s, 3H), 3.88 (s, 3H), 6.11 (s, 1H), 7.54 (m, 2H), 8.07 (dd, J=1.8, 6.6 Hz, 1H); IR (KBr) 2984 (w), 2949 (w), 2927 (w), 2849 (w), 1677 (s), 1646 (s), 1619 (s), 1231 (s), 1078 (m), 1060 (m), 861 (m), 776 (m). Crystallization from MeOH yielded orange needles (mp 140°–141° C.). A 1.8 g run performed in an analogous manner yielded 1.68 g (94%) of product (>95% pure by $^1$H NMR with the impurity being unreacted starting material).

Example 56

Preparation of 3-Methoxy-6-methyl-1H-1-benzazepine-2,5-dione (92)

To stirred, ice bath cold, concd H$_2$SO$_4$ (12 mL, Baker), there was added 2-methoxy-5-methylnaphthalene-1,4-dione (800 mg, 3.96 mmol) in portions. A deep red solution resulted. To this cold solution, NaN$_3$ (515 mg, 7.92 mmol, Aldrich) was added in portions over one min. The ice bath was removed and the reaction was allowed to stir at rt for 18 h under N$_2$. Nitrogen evolution was noted. The reaction was added to crushed ice (50 mL) to give a thick green suspension. This was diluted with H$_2$O (30 mL) and vigorously stirred with 30% MeOH/70% CHCl$_3$ (60 mL) until all the solid had dissolved. The layers were separated and the aqueous portion was extracted with 30% MeOH/70% CHCl$_3$ (2×30 mL). The combined red organic portion was washed with water (1×30 mL), saturated NaHCO$_3$ (1×30 mL) and brine (1×30 mL), filtered through cotton and the solvent removed in vacuo to give a red solid (800 mg). Crystallization from 95% EtOH (dissolved in 30 mL, hot filtered, concd to 20 mL, allowed to cool to rt then in an ice bath) a gave colorless fluffy needles (564 mg, 66%, pure by $^1$H NMR); mp 215.5°–217° C.; $^1$H NMR (DMSO-d$_6$) δ2.32 (s, 3H), 3.71 (s, 3H), 6.32 (s, 1H), 7.08 (d, J=7.5 Hz, 1H), 7.15 (d, J=8.1 Hz, 1H), 7.36 (t, J=7.8 Hz, 1H), 11.00 (s, 1H); IR (KBr) 3195 (m), 3134 (m), 3061 (m), 2999 (m), 2967 (m), 2939 (m), 1691 (s), 1649 (s), 1616 (s), 1212 (m), 834 (m), 783 (m); MS (m/z) 217 (M$^+$, 100).

Example 57

Preparation of 3-Hydroxy-6-methyl-1H-1-benzazepine-2,5-dione (93)

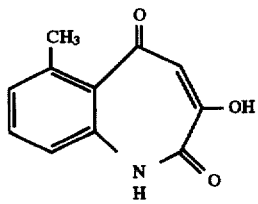

To a stirred solution of 3-methoxy-6-methyl-1H-1-benzazepine-2,5-dione (350 mg, 1.61 mmol) in dry CH$_2$Cl$_2$ (25 mL, distilled from CaH$_2$) under N$_2$, there was added a solution of BBr$_3$ in CH$_2$Cl$_2$ (5 mL, 1M, Aldrich) in one portion over 30 seconds at rt. The reaction solution immediately became orange, then an orange precipitate formed during the addition. The reaction was allowed to stir under N$_2$ at rt for 65 min. The reaction was added to saturated NaHCO$_3$ (50 mL) and the resulting mixture was vigorously stirred for 15 min to give biphasic system containing some solid material. The phases were separated and the aqueous portion vacuum filtered. The clear, pale yellow, aqueous portion was extracted with CH$_2$Cl$_2$ (1×10 mL). The aqueous portion was acidified with concd HCl (pH 2). The resulting precipitate was collected by filtration, washed to neutrality with water (6×2 mL) and dried in vacuo to yield a highly electrostatic, colorless powder (mass could not be determined). Crystallization from EtOAc (dissolved in 15 mL, hot filtered, concd to 7 mL, allowed to cool to rt) initially yielded near colorless needles, which upon standing overnight at rt, transformed into beige cubes (146 mg, 45%, pure by $^1$H NMR); mp 187.5°–188.5° C. (dec.); $^1$H NMR (DMSO-d$_6$) δ2.34 (s, 3H), 6.30 (s, 1H), 7.09 (d, J=7.2 Hz, 1H), 7.21 (d, J=8.1 Hz, 1H), 7.37 (t, J=7.8 Hz, 1H), 10.39 (s, 1H), 11.20 (s, 1H); IR (KBr) 3207 (m), 3047 (m), 1642 (s), 1607 (s), 1598 (s), 1348 (m), 789 (m); Anal. Calcd for C$_{11}$H$_9$NO$_3$: C, 65.02, H, 4.46, N, 6.89. Found: C, 65.26; H, 4.54; N, 6.89. Concentration of the mother liquor yielded an additional portion of orange cubes (30 mg, 9%, pure by $^1$H NMR); mp 184.5°–188° C. In one crystallization, the above mentioned needles were collected; mp 177°–179° C. (dec); IR (KBr) 3389 (m), 3193 (m), 1661 (s), 1646 (s), 1601 (m), 1580 (m), 1350 (m), 1204 (m).

Example 58

Preparation of 5,8-Dihydro-2-methoxy-5,7-dimethylnaphthalene-1,4-dione (94)

To a stirred suspension of 2-bromo-5-methoxybenzoquinone (9.8 g, 44.7 mmol) in toluene (250 mL) there was added trans-2-methyl-1,3-pentadiene (31 mL Aldrich, 75%) in one portion. The reaction mixture was allowed to stir in a 60°–70° C. oil bath for 18 h. A homogeneous solution was present. The status of the reaction was determined by $^1$H NMR. Since the adduct was not stable once the reaction solvent was evaporated, an aliquot was diluted in half with MeOH and treated with an excess of Et$_3$N. After one min, dilute HCl (10% concd HCl/90% H$_2$O) was added and the mixture extracted with CHCl$_3$. The extract was washed with H$_2$O, filtered through cotton and the solvent removed in vacuo. The $^1$H NMR was then determined in CDCl$_3$. The absence of a resonance at 7.24 ppm indicated that the stating quinone was totally consumed. The remaining reaction mixture was allowed to cool to rt and was diluted in half with MeOH. The reaction was purged with N$_2$ for 5 min with stirring and Et$_3$N (9.22 g, 12.7 mL, 91.2 mmol, EM) was added. The reaction mixture darkened. The reaction was allowed to stir for 5 min under N$_2$. Dilute HCl (vide supra, 200 mL) was then vigorously stirred in to give a lighter yellow/orange mixture. The layers were separated and the aqueous layer was extracted with toluene (1×20 mL). The combined toluene portion was washed with H$_2$O and brine (50 mL each), filtered through cotton and the solvent removed in vacuo to give an orange solid (10.3 g). Crystallization from 95% EtOH (dissolved in 50 mL boiling solvent, hot filtered, allowed to cool to rt) yielded an orange/yellow crystalline solid (7.80 g, 78% for the two steps, pure by TLC and $^1$H NMR); mp 118.5–120.5;

$^1$H NMR δ1.15 (d, J=6.9 Hz, 3H), 1.77 (s, 3H), 2.90 (dd, J=5.7, 23.4 Hz, 1H), 3.00 (dd, J=5.1, 23.7 Hz, 1H), 3.41 (m, 1H), 3.81 (s, 3H), 5.47 (m, 1H), 5.87 (s, 1H); IR (KBr) 2975 (w), 2959 (w), 2856 (w), 1667 (s), 1645 (s), 1634 (s), 1607 (s), 1223 (s), 10$_{16}$ (m), 862 (m), 844 (m).

Example 59

Preparation of 2-Methoxy-5,7-dimethylnaphthalene-1,4-dione (95)

To a solution of 5,8-dihydro-2-methoxy-5,6-dimethylnaphthalene-1,4-dione (4.00 g, 18.3 mmol) in CHCl$_3$ (150 mL), there was added MnO$_2$ (9.49 g, 110 mmol, Fluka). The stirred suspension was heated at reflux and monitored by $^1$H NMR (filtered aliquot through celite and removed solvent in vacuo). After 4.5 h, an additional portion of MnO$_2$ (4.8 g, 55 mmol) was added and the reaction was allowed to reflux for an additional 3 h (7.5 h total). The reaction was allowed to stir overnight at rt and was filtered through Celite. The pad was washed with CHCl$_3$ (3×30 mL). Solvent removal yielded a yellow powder (3.80 g, 95%, pure by TLC and $^1$H NMR); mp 146°–148° C.; $^1$H NMR (CDCl$_3$) δ2.43 (s, 3H), 2.71 (s, 3H), 3.87 (s, 3H), 6.07 (s, 1H), 7.33 (s, 1H), 7.87 (s, 1H); IR (KBr) 3070 (w), 2982 (w), 2968 (w), 2946 (w), 2926 (w), 2850 (w), 1676 (s), 1646 (s), 1636 (s), 1619 (s), 1601 (s), 1247 (s), 1243 (s), 1236 (s), 1105 (s), 865 (m), 705 (m). Crystallization from EtOH yielded yellow needles (mp 147.5°–149° C.).

Example 60

Preparation of 6,8-Dimethyl-3-methoxy-1H-1-benzazepine-2,5-dione (96)

To stirred, ice bath cold, concd H$_2$SO$_4$ (14 mL, Baker), there was added 5,7-dimethyl-2-methoxynaphthalene-1,4-dione (1.00 g, 4.63 mmol) in portions. A deep red solution resulted. To this cold solution, NaN$_3$ (601 mg, 9.24 mmol, Aldrich) was added in portions over one min. The ice bath was removed and the reaction was allowed to stir at rt for 18 h under N$_2$. Nitrogen evolution was noted. The reaction was added to crushed ice (100 mL) to give a brown suspension. A solution of 30% MeOH/70% CHCl$_3$ (90 mL) was added and vigorously stirred until all the solid had dissolved. The layers were separated and the aqueous portion was extracted with 30% MeOH/70% CHCl$_3$ (2×30 mL). The combined red organic portion was washed with water (1×30 mL), saturated NaHCO$_3$ (1×30 mL) and brine (1×30 mL), filtered through cotton and the solvent removed in vacuo to give a red solid (~1 g). Crystallization from 95% EtOH (dissolved in 40 mL, hot filtered, concd to 25 mL, allowed to cool to rt then in an ice bath) a gave colorless fluffy needles (678 mg, 63%, pure by $^1$H NMR); mp 237°–238° C.; $^1$H NMR (DMSO-d$_6$) δ2.25 (s, 3H), 2.29 (s, 3H), 3.70 (s, 3H), 6.28 (s, 1H), 6.90 (s, 1H), 6.94 (s, 1H), 10.94 (s, 1H); $^{13}$C NMR (DMSO-d$_6$) δ 20.66, 56.04, 113.58, 118.69, 127.47, 128.10, 135.44, 137.45, 141.20, 153.83, 160.10, 190.53; IR (KBr) 3207 (m), 3003 (m), 2920 (m), 1682 (s), 1645 (s), 1619 (s), 1241 (m), 1224 (m), 855 (m); MS (m/z) 231 (M$^+$, 100).

Example 61

Preparation of 6,8-Dimethyl-3-hydroxy-1H-1-benzazepine-2,5-dione (97)

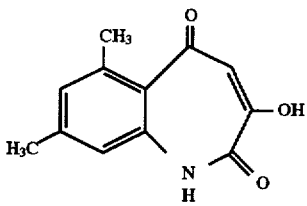

To a stirred solution of 6,8-dimethyl-3-methoxy-1H-1-benzazepine-2,5-dione (600 mg, 2.59 mmol) in dry CH$_2$Cl$_2$ (50 mL, distilled from CaH$_2$) under N$_2$, there was added a solution of BBr$_3$ in CH$_2$Cl$_2$ (10 mL, 1M, Aldrich) in one portion over 2 min at rt. The reaction solution immediately became orange, then an orange precipitate formed during the addition. The reaction was allowed to stir under N$_2$ at rt for 60 min. The reaction was added to saturated NaHCO$_3$ (50 mL) and the resulting mixture was vigorously stirred for 15 min to give a triphasic system (CH$_2$Cl$_2$, aqueous, solid). The CH$_2$Cl$_2$ portion was removed with a pipet. The combined solid and aqueous portion was acidified with concd HCl (pH 2) and the resulting mixture allowed to stir for 10 min. A solution of 30%MeOH/70% CHCl$_3$ (90 mL) was added and the mixture vigorously stirred until the solid dissolved. The layers were separated and the aqueous layer was extracted with 30%MeOH/70% CHCl$_3$ (2×30 mL). The CHCl$_3$ portions was washed with H$_2$O (2×30 mL) and brine (1×30 mL), filtered through cotton and the solvent removed in vacuo to give a beige solid (453 mg). Crystallization from EtOAc (dissolved in 15 mL, hot filtered, concd to 7 mL, allowed to cool to rt) yielded near colorless leafs (277 mg, 49%, pure by $^1$H NMR); mp 189°–190.5° C. (dec.); $^1$H NMR (DMSO-d$_6$) δ2.26 (s, 3H), 2.31 (s, 3H), 6.28 (s, 1H), 6.92 (s, 1H), 7.01 (s, 1H), 10.29 (s, 1H), 11.12 (s, 1H); IR (KBr) 3319 (m), 3204 (m), 3010 (m), 1647 (s), 1607 (s), 1575 (m), 1403 (m), 1358 (m), 1219 (m), 867 (m); Anal. Calcd for C$_{12}$H$_{11}$NO$_3$: C, 66.35, H, 5.10, N, 6.45. Found: C, 66.09; H, 5.06; N, 6.38. Concentration of the mother liquor yielded an additional portion of a beige granular solid (100 mg, 18%, pure by $^1$H NMR); mp 191°–195° C.

Example 62

Preparation of 6,8-Dimethyl-3-methoxy-7-nitro-1H-1-benzazepine-2,5-dione (98)

To stirred, ice bath cold, concd H$_2$SO$_4$ (14 mL, Baker), there was added 5,7-dimethyl-2-methoxy-naphthalene-1,4-dione (1.00 g, 4.63 mmol) in portions. A deep red solution resulted. To this cold solution, NaN$_3$ (601 mg, 9.24 mmol, Aldrich) was added in portions over one min. The ice bath was removed and the reaction was allowed to stir at rt for 18 h under N$_2$. Nitrogen evolution was noted. Analysis (TLC, 5% MeOH/95% CHCl$_3$) of an aliquot (added to H$_2$O and extracted with CHCl$_3$) indicated total conversion of the quinone to the lower R$_f$ benzazepine. The reaction was recooled in an ice bath for 5 min. Solid KNO$_3$ (514 mg, 5.08 mmol, Baker) was added very slowly to the stirred reaction mixture. The reaction frothed vigorously during the addition (it could froth out of the reaction vessel if the addition is made too quickly). After addition, the ice bath was removed and the reaction was allowed to stir at rt under N$_2$. The reaction was monitored by TLC (as above). The analysis showed the formation of a very slightly lower (easily missed) R$_f$ spot. No change in the reaction was noted between 1 and 1.5 h after the addition of the KNO$_3$. Therefore, the reaction was recooled in an ice bath and a second portion of KNO$_3$ (233 mg, 2.31 mmol) was carefully added (little frothing this time). The ice bath was removed and the reaction was allowed to stir at rt under $N_2$. After an additional 40 min, the analysis showed the reaction to be complete. The reaction was added to crushed ice (100 mL) to give an orange suspension. A solution of 30% MeOH/70% $CHCl_3$ (90 mL) was added and vigorously stirred until all the solid had dissolved. The layers were separated and the aqueous portion was extracted with 30% MeOH/70% $CHCl_3$ (2×30 mL). The combined orange organic portion was washed with water (1×50 mL), saturated $NaHCO_3$ (2×50 mL) and brine (1×50 mL), filtered through cotton and the solvent removed in vacuo to give an orange solid (~1.1 g). Precipitation from 95% EtOH (dissolved in 110 mL, hot filtered, concd to 50 mL, allowed to cool to rt) gave an orange powder (668 mg, 52%, ~95% pure by $^1H$ NMR with the impurity possibly being the 9-nitro isomer); mp 262°–266° C. A portion of this material (50 mg) was reprecipitated from 95% EtOH (dissolved in boiling solvent (5 mL), hot filtered, concd to 3 mL, allowed to cool to rt) to yield a beige powder (40 mg, 80% recovery, pure by $^1H$ NMR); mp 268°–271° C.; $^1H$ NMR (DMSO-$d_6$) δ2.17 (s, 3H), 2.23 (s, 3H), 3.73(s, 3H), 6.38 (s, 1H), 7.18 (s, 1H), 11.25 (s, 1H); $^{13}C$ NMR (DMSO-$d_6$) δ14.88, 16.85, 56.35, 113.24, 120.70, 128.58, 128.77, 132.20, 136.00, 148.91, 154.43, 160.06, 189.60; IR (KBr) 3382 (w), 3207 (w), 3127 (w), 3095 (w), 3046 (w), 2984 (w), 2945 (w), 1687 (s), 1644 (s), 1615 (s), 1574 (m), 1528 (m), 1511 (m), 1445 (m), 1427 (m), 1386 (m), 1364 (m), 1286 (m), 1240 (m), 1230 (m), 1094 (m), 1035 (w), 992 (m), 880 (m), 853 (m), 824 (w), 666 (w), 464 (w); MS (m/z) 276 ($M^+$, 100).

Example 63

Preparation of 6,8-Dimethyl-3-hydroxy-7-nitro-1H-1-benzazepine-2,5-dione (99)

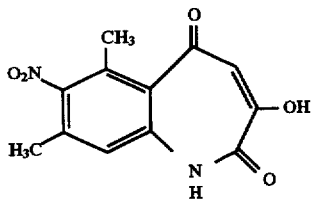

To a stirred suspension of 6,8-dimethyl-3-methoxy-7-nitro-1H-1-benzazepine-2,5-dione (460 mg, 1.66 mmol) in dry $CH_2Cl_2$ (50 mL, distilled from $CaH_2$) under $N_2$, there was added a solution of $BBr_3$ in $CH_2Cl_2$ (6 mL, 1M, Aldrich) in one portion over 2 min at rt. The reaction suspension immediately became orange. The reaction was allowed to stir under $N_2$ at rt for 60 min. The reaction was added to saturated $NaHCO_3$ (60 mL) and the resulting mixture was vigorously stirred for 15 min. An orange aqueous portion and an organic emulsion were present. The mixture was vacuum filtered and the collected solid washed with $CH_2Cl_2$ (3×5 mL). The aqueous portion was washed with $CH_2Cl_2$ (1×10 mL). Analysis (TLC, 20% dioxane, 57% 2-propanol, 11.5% $H_2O$, 11.5% $NH_4OH$) showed the solid and aqueous portions to be identical. Therefore, they were combined and the resulting suspension acidified (pH 2) with concd HCl. The resulting suspension was allowed to stir for 10 min at rt and the solid collected by filtration. The collected solid was washed to neutrality with $H_2O$ (6×2 mL). Crystallization from 95% EtOH (dissolved in boiling solvent (15 mL), hot filtered, concd to 7 mL, allowed to cool to rt) yielded a beige crystalline solid (186 mg, 43%, pure by $^1H$ NMR and TLC); mp 229.5–230.5 (dec); $^1H$ NMR (DMSO-$d_6$) δ2.17 (s, 3H), 2.23 (s, 3H), 6.34 (s, 1H), 7.23 (s, 1H), 10.72 (s, 1H), 11.40 (s, 1H); IR (KBr) 3208 (m), 3091 (w), 3061 (w), 3003 (w), 1672 (m), 1646 (s), 1616 (s), 1572 (m), 1532 (m), 1443 (w), 1398 (m), 1364 (m), 1350 (m), 1320 (m), 1271 (m), 1219 (m), 883 (m), 862 (w), 815 (w), 785 (w), 727 (w), 682 (w), 636 (w), 601 (w), 565 (w), 520 (w), 458 (m); Anal. Calcd for $C_{12}H_{10}NO_5$: C, 54.97; H, 3.84; N, 10.68. Found: C, 54.89; H, 3.70; N, 10.65.

Example 64

Preparation of 5,6-Dimethyl-2-methoxynaphthalene-1,4-dione (100)

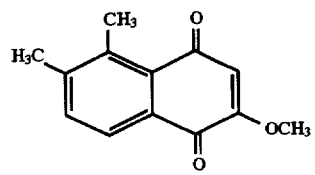

To a stirred suspension of 2-bromo-5-methoxybenzoquinone (8.70 g, 40.1 mmol) in toluene (225 mL) there was added trans-3-methyl-1,3-pentadiene (5.00 g, 61.0 mmol, Aldrich) in one portion. The reaction mixture was allowed to stir in a 60°–70° C. oil bath for 3 days. A homogeneous solution was present. The status of the reaction was determined by $^1H$ NMR. Since the adduct was not stable once the reaction solvent was evaporated, an aliquot was diluted in half with MeOH and treated with an excess of $Et_3N$. After one min, dilute HCl (10% concd HCl/90% $H_2O$) was added and the mixture extracted with $CHCl_3$. The extract was washed with $H_2O$, filtered through cotton and the solvent removed in vacuo. The $^1H$ NMR was then determined in $CDCl_3$. The absence of a resonance at 7.24 ppm indicated that the starting quinone was totally consumed. This analysis also indicated that 2 major products were present with a ratio of approximately 7 to 3. The remaining reaction mixture was allowed to cool to rt and was diluted in half with MeOH. The reaction was purged with $N_2$ for 5 min with stirring and $Et_3N$ (8.11 g, 11.2 mL, 80.2 mmol, EM) was added. The reaction mixture darkened. The reaction was allowed to stir for 15 min under $N_2$. Dilute HCl (vide supra, 200 mL) was then vigorously stirred in to give a lighter yellow/orange mixture. After stirring for 5 min, the layers were separated and the aqueous extracted with toluene (1×50 mL). The combined toluene portion was washed with $H_2O$ and brine (50 mL each), filtered through cotton and the solvent removed in vacuo to give an orange oil (~9.2 g). Without further purification, the oil was dissolved in $CHCl_3$ (400 mL) and $MnO_2$ (17.4 g, 200 mmol, Fluka) was added. The stirred suspension was heated at reflux for one h. Analysis ($^1H$ NMR) showed approximately 33% reaction. An identical portion of $MnO_2$ was added and reflux was continued for an additional 2 h. The analysis now showed approximately 70% conversion. A third identical portion of $MnO_2$ was then added and the reaction was heated at reflux for an additional 2 h and then allowed to stir overnight at rt. The analysis now showed total conversion to the title compound (~70%) and the 7,8-dimethyl isomer (~30%) with a trace amount of unknown side product also being present. The inorganic portion was removed by filtration through Celite. The filter pad was exhaustively washed with $CHCl_3$ (4×500 mL). Solvent removal from the combined filtrate and wash yielded a yellow solid (7.1 g). Washing the filter pad with additional $CHCl_3$ failed to yield any additional product. The yellow solid was crystallized from 95%

EtOH (dissolved in boiling solvent (225 mL), hot filtered, concd to 150 mL, allowed to cool to rt) to yield yellow needles (4.8 g, 55%, ~90 to 95% pure by TLC (5% EtOAc/ 95% CHCl₃) and ¹H NMR); mp 165.5°–168.5° C. Recrystallization from 95% EtOH (dissolved in boiling solvent (175 mL), concd to 150 mL, allowed to cool to rt) yielded yellow needles (4.20 g, 48% for the three steps, >95% pure by TLC and ¹H NMR); mp 169–171; ¹H NMR (CDCl₃) δ2.42 (s, 3H), 2.67 (s, 3H), 3.86 (s, 3H), 6.07 (s, 1H), 7.45 (d, J=7.8 Hz, 1H), 7.95 (d, J=7.8 Hz, 1H); IR (KBr) 3060 (w), 3007 (w), 2944 (w), 2848 (w), 1674 (s), 1640 (s), 1620 (s), 1582 (m), 1572 (m), 1460 (w), 1451 (w), 1437 (w), 1405 (w), 1377 (w), 1368 (m), 1314 (m), 1279 (m), 1270 (w), 1236 (s), 1186 (w), 1174 (w), 1145 (m), 1078 (s), 1038 (w), 1023 (w), 1006 (m), 955 (m), 909 (w), 888 (m), 862 (m), 839 (w), 801 (m), 750 (w), 694 (w), 635 (w), 586 (w), 508 (w), 480 (w), 451 (w).

Example 65

Preparation of 2-Methoxy-6-tosylate-1,4-naphthoquinone (101)

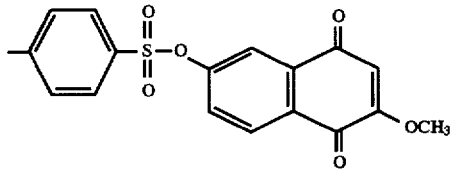

In a 50 mL round bottom flask 2-methoxy-6-hydroxy-1, 4-naphthoquinone (1.3 g, 6.4 mmol) was suspended in dry CH₂Cl₂ (40 mL). Triethylamine (Aldrich, 5 mL) was added to the suspension resulting in a red solution. p-Toluenesulfonyl chloride (Aldrich, 2.4 g, 12.8 mmol) was added all at once and allowed to stir for 2 h under N₂ at rt. The light brown mixture was then extracted with 10% HCl (3×20 mL), sat. NaHCO₃ (3×20 mL), then water (1×20 mL). The light brown organic phase was dried over MgSO₄ then evaporated to dryness (roto-vap). The resulting solid was passed through a silica-gel column (10×2.5 cm) using CHCl₃/CH₃OH (20:1) as solvent. 2-Methoxy-6-tosylate-1, 4-naphthoquinone was isolated as a light green solid (1.4 g, 61%), m.p. 124°–134° C.; ¹H NMR (CDCl₃) δ2.48 (s, 3H), 3.90 (s, 3H), 6.22 (s, 1H), 7.35 (d, J=8.1 Hz, 2H), 7.38 (dd, J=8.4, 2.1 Hz, 1H), 7.65 (d, J=2.1 Hz, 1H), 7.74 (d, J=8.1 Hz, 2H), 8.09 (d, J=8.4 Hz, 1H).

Example 66

Preparation of 4-Methoxy-8-hydroxy-1H-1-benzazepine-2, 5-dione (102)

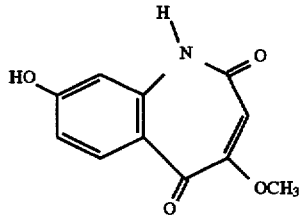

In a 50 mL round bottom flask 2-methoxy-6-tosylate-1, 4-naphthoquinone (1.0 g, 2.79 mmol) was dissolved in cold (5° C.) sulfuric acid (conc., 10 mL) stirred and suspended in an ice bath. Sodium azide (Aldrich, 907 mg, 14.0 mmol) was added in 30 mg portions over 10 min. Gas evolution was noted. The red solution was allowed to stir under N₂ at rt for 48 hours. The reaction was added to swirled ice/water (200 mL) giving a red solution. This was extracted with CHCl₃/ CH₃OH (4:1) (15×35 mL) giving a light brown solution. This was filtered through cotton and the solvent removed (roto-vap) giving a brown solid (500 mg). This was passed through a silica-gel column (2.5×15 cm) using CHCl₃/ CH₃OH (9:1) as solvent. This compound was judged to be greater than 95% pure by ¹H NMR (350 mg, 58%), mp 273°–275° C., ¹H NMR (DMSO-d₆) δ3.72 (s, 3H), 5.97 (s, 1H), 6.60 (d, J=8.9 Hz, 1H), 6.66 (s, 1H), 7.75 (d, J=8.9 Hz, 1H), 10.63 (s, 1H), 10.80 (s, 1H).

Example 67

Preparation of 4,8-Dihydroxy-1H-1-benzazepine-2,5-dione (103)

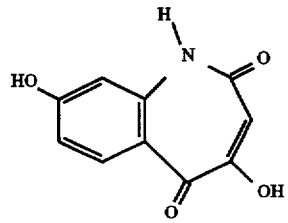

In a 25 mL round bottom flask 4-methoxy-8-hydroxy-1H-1benzazepine-1,5-dione (150 mg, 0.68 mmol) was suspended in dry CH₂Cl₂ (8 mL) then a solution of BBr₃ in CH₂Cl₂ (3.5 mL, 1M, Aldrich) in 3 portions over 1 min at rt. The reaction became orange but remained a suspension. The reaction was stirred under N₂ for 45 min. The reaction was added to saturated NaHCO₃ (30 mL) and was allowed to stir for 15 min at rt giving a yellow solution. The solution was extracted with CHCl₃ (1×15 mL) and discarded. The aqueous yellow solution was acidified with 10% HCl to pH 2, then stirred for 10 min at rt. The solid was collected by filtration and washed with water (25 mL), giving a brown solid (81 mg, 58% yield, 95% pure by ¹H NMR). mp>350° C.; ¹H NMR (DMSO-d₆) δ6.10 (d, J=1 Hz, 1H), 6.63 (dd, J=9.0, 2.0 Hz, 1H), 6.71 (d, J=2.0 Hz 1H), 8.00 (d, J=9.0 Hz, 1H), 10.21 (s, 1H), 10.76 (s, 1H), 10.86 (s, 1H).

Example 68

Preparation of 5-Bromovanillin (104)

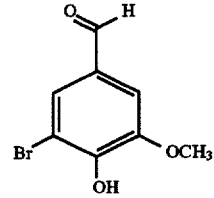

In a 250 mL round bottom flask vanillin (Aldrich, 33.3 g, 0.22 moles) was dissolved in glacial acetic acid (100 mL) with stirring. A solution of bromine (Baker, 35.0 g, 0.43 mol, 11.2 mL) in glacial acetic acid (100 mL) was added to the solution of vanillin. After 5 min a precipitate formed but the reaction was allowed to stir for an additional 15 min. The solid was collected by filtration giving 18.2 g, 35%. The filtrate was then slowly added to water (300 mL) and allowed to stand overnight. The resulting solid was filtered and dried under vacuum giving additional product (18.4 g, 35%, total yield 36.6 g, 70%), mp 159°–163° C. (lit. 163°–164° C.), ¹H NMR (CDCl₃) δ3.99 (s, 3H), 6.61 (bs, 1H), 7.36 (d, J=1.3 Hz, 1H), 7.64 (d, J=1.3 Hz, 1H), 9.79 (s, 1H).

Example 69

Preparation of 2-Bromo-6-methoxy-1,4-benzoquinone (105)

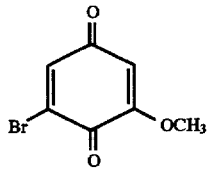

In a 500 ml Erlenmyer flask 5-bromovanillin (6.3 g, 26.8 mmol) was dissolved in 4% NaOH (40 mL) and degassed with N₂ for 20 min. Hydrogen peroxide (Baker, 30%, 5 mL diluted with 40 mL of water) was added to the stirring 5-bromovanillin solution. Heating was observed but the reaction did not reflux. The reaction was allowed to stir under N₂ for 1 h. HCl (concd, 10 mL) was added in portions to prevent over foaming. Ferric chloride, hydrated (Baker, 8 g) dissolved in water (20 mL), was added all at once and the reaction was allowed to stir for 1 h. The resulting precipitate was collected and washed with water (20 mL). The dark solid was filtered through a pad of silica gel (5×3 cm) using CHCl₃ as solvent. The resulting yellow solid was crystallized from methanol giving orange needles, (4.2 g, 72%, one spot on TLC and >95% pure by ¹H NMR), mp 157°–158° C. (lit, 161°–162° C.), ¹H NMR (CDCl₃) δ3.86 (s, 3H), 5.96 (d, J=2 Hz, 1H), 7.21 (d, J=2 Hz, 1H).

Example 70

Preparation of 7-Methoxy-2-methylquinoline-5,8-dione (106)

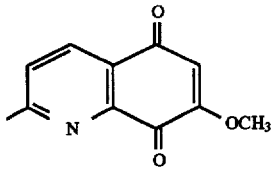

In a 50 mL round bottom flask 2-bromo-6-methoxy-1,4-benzoquinone (282 mg, 1.3 mmol) was dissolved in dry chlorobenzene (28 mL) along with 1-(tert-butyldimethyl silyloxy)-2-methyl-1-aza-1,3-butadiene (130 mg, 0.65 mmol). The solution was stirred and heated to reflux for 22 h under N₂. The dark reaction was allowed to cool and was added to a silica gel column (2.5×9 cm). The column was eluted with EtOAc/hexane (5:1) then EtOAc and finally ethanol. The solvent was removed, benzene was added, and the resulting mixture was heated and filtered to remove insoluble impurities. Evaporation of the filtrate gave 75 mg, 57% of the crude product. ¹H NMR (CDCl₃) δ2.81 (s, 3H), 3.92 (s, 3H), 6.18 (s, 1H), 7.44 (d, J=5 Hz, 1H), 8.80 (d, J=5 Hz, 1H).

Example 71

Preparation of 7-Methoxy-4-methylquinoline-5,8-dione (107)

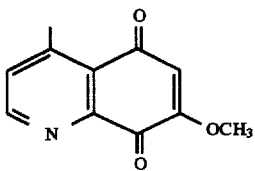

In a 50 mL round bottom flask 2-bromo-6-methoxy-1,4-benzoquinone (282 mg, 1.3 mmol) was dissolved in dry chlorobenzene (28 mL) along with 1-(tert-butyldimethylsilyloxy)-1-aza-1,3-pentadiene (130 mg, 0.65 mmol). The solution was stirred and heated to reflux for 4 days under N₂. The dark reaction was allowed to cool and was added to a silica gel column (2.5×9 cm). The column was eluted with EtOAc/hexane (5:1) then EtOAc and finally ethanol. The solvent was removed, benzene was added, and the resulting mixture was heated and filtered to remove insoluble impurities. Evaporation of the filtrate gave 62 mg, 47% of the crude product. ¹H NMR (CDCl₃) δ2.76 (s, 3H), 3.93 (s, 3H), 6.20 (s, 1H), 7.52 (d, J=8 Hz, 1H), 8.30 (d, J=8 Hz, 1H).

Example 72

Preparation of 6,7-dimethyl-3-methoxy-1H-1-benzazepine-2,5-dione (108)

To stirred, ice bath cold, concd H₂SO₄ (14 mL, Baker), there was added 5,6-dimethyl-2-methoxynaphthalene-1,4-dione (1.00 g, 4.63 mmol) in portions. A deep red solution resulted. To this cold solution, NaN₃ (601 mg, 9.24 mmol, Aldrich) was added in portions over one min. The ice bath was removed and the reaction was allowed to stir at rt for 18 h under N₂. Nitrogen evolution was noted. The reaction was added to crushed ice (100 mL) to give a green suspension. A solution of 30% MeOH/70% CHCl₃ (60 mL) was added and vigorously stirred until all the solid had dissolved. The layers were separated and the aqueous portion was extracted with 30% MeOH/70% CHCl₃ (2×30 mL). The combined red organic portion was washed with water (1×30 mL), saturated NaHCO₃ (1×30 mL) and brine (1×30 mL), filtered through cotton and the solvent removed in vacuo to give a red solid (~1 g). Crystallization from 95% EtOH (dissolved in 25 mL, hot filtered, concd to 20 mL, allowed to cool to rt) gave beige needles (689 mg, 64%, ~85 pure by ¹H NMR and TLC). Recrystallization from 95% EtOH (dissolved in boiling solvent (19 mL), allowed to cool to rt) gave near colorless needles (476 mg, 44%, pure by ¹H NMR and TLC); mp 218°–220° C., lit. none; ¹H NMR (DMSO-d₆) δ2.16 (s, 3H), 2.22 (s, 3H), 3.69 (s, 3H), 6.33 (s, 1H), 7.03 (d, J=8.1 Hz, 1H), 7.27 (d, J=8.1 Hz, 1H), 10.88 (s, 1H); ¹³C NMR (DMSO-d₆) δ16.33, 19.49, 55.96, 113.22, 117.79, 131.31, 132.39, 132.73, 133.34, 134.49, 153.70, 160.13, 192.25; IR (KBr) 3196 (m), 3124 (m), 2983 (m), 1688 (s), 1646 (s), 1616 (s), 1507 (w), 1483 (m), 1443 (m), 1421 (m), 1400 (m), 1384 (m), 1371 (w), 1332 (m), 1300 (m), 1282 (m), 1247 (m), 1219 (m), 1176 (m), 1152 (m), 1108 (w), 1056 (m), 1035 (w), 1017 (w), 999 (m), 983 (m), 941 (w), 889 (m), 859 (m), 832 (m), 821 (m), 808 (m), 775 (w), 761 (m), 747 (w), 711 (w), 661 (m), 641 (w), 618 (w), 585 (w), 565 (w), 516 (w), 476 (w), 451 (w); MS (m/z) 231 (M⁺, 100), 202 (40), 188 (30), 174 (40), 160 (50).

Example 73

Preparation of 6,7-dimethyl-3-hydroxy-1H-1-benzazepine-2,5-dione (109)

To a stirred solution of 6,7-dimethyl-3-methoxy-1H-1-benzazepine-2,5-dione (300 mg, 1.30 mmol) in dry $CH_2Cl_2$ (40 mL, distilled from $CaH_2$) under $N_2$, there was added a solution of $BBr_3$ in $CH_2Cl_2$ (6 mL, 1M, Aldrich) in one portion over 1 min at rt. The reaction solution immediately became orange, then an orange precipitate formed during the addition. The reaction was allowed to stir under $N_2$ at rt for 45 min. The reaction was added to saturated $NaHCO_3$ (50 mL) and the resulting mixture was vigorously stirred for 15 min to give a yellow aqueous phase and a near colorless organic phase. The phases were separated and the aqueous phase washed with $CH_2Cl_2$ (1×10 mL). The aqueous portion was acidified with concd HCl (pH 2). The resulting precipitate was collected by vacuum filtration, washed to neutrality with $H_2O$ (6×2 mL) and dried in vacuo to give a yellow powder. Crystallization from EtOAc (dissolved in 20 mL, hot filtered, concd to 10 mL, allowed to cool to rt) yielded fine green needles (154 mg, 55%, pure by $^1H$ NMR); mp 206°–208° C. (dec.); $^1H$ NMR (DMSO-$d_6$) δ2.16 (s, 3H), 2.23 (s, 3H), 6.30 (s, 1H), 7.09 (d, J=8.1 Hz, 1H), 7.28 (d, J=8.4 Hz, 1H), 10.31 (bs, 1H), 11.08 (s, 1H); IR (KBr) 3260 (m), 3194 (m), 3078 (m), 2989 (m), 1643 (s), 1614 (s), 1581 (m), 1503 (m), 1479 (m), 1449 (m), 1393 (s), 1374 (m), 1347 (m), 1310 (m), 1284 (m), 1259 (m), 1238 (w), 1212 (s), 1145 (m), 1047 (m), 992 (m), 969 (w), 883 (m), 871 (m), 851 (m), 833 (m), 824 (m), 771 (m), 755 (w), 705 (m), 658 (m), 633 (m), 613 (m), 571 (m), 501 (m), 473 (m), 406 (m); Anal. Calcd for $C_{12}H_{11}NO_3$; C, 66.35, H, 5.10, N, 6.45. Found: C, 66.65; H, 4.81; N, 6.44.

Example 74

Preparation of 6,7-dichloro-2-methoxy-5-methyl-5,6,7,8-tetrahydronapthalene-1,4-dione (110)

A solution of $Cl_2$ in $CHCl_3$ (freed of inhibitor by passing through a silica gel column) was prepared by adding concd HCl to stirred $MnO_2$ and bubbling the resulting effluent through inhibitor free $CHCl_3$. The resulting green solution was passed through a small silica gel column prior to use to remove $H_2O$. The $Cl_2$ concentration was not determined. To a stirred solution of 5,8-dihydro-2-methoxy-5-methylnaphthalene-1,4-dione (950 mg, 4.65 mmol) in inhibitor free $CHCl_3$ (20 mL) the above described $Cl_2$ solution was added in portions with stirring. The reaction was monitored by TLC ($CHCl_3$). When the analysis indicated the total consumption of the starting material, the solvent was removed from the reaction mixture in vacuo to give a yellow oil. This was subject to column chromatography (silica gel, 2.5×25 cm column, 50% hexanes/50% $CHCl_3$ elution). Some impurities eluted initially. The desired product eluted next as a yellow band followed closely by impurities. Solvent removal from the purest fractions yielded a yellow oil (293 mg, 80–90% pure by TLC and $^1H$ NMR). The mixed product fraction was stripped of solvent in vacuo and the resulting yellow oil re-chromatographed in a manner similar to that described above (employed 2.5×50 cm column). Solvent removal from the purest fractions yielded an additional portion of a yellow oil (132 mg, 80–90% pure by TLC and $^1H$ NMR; total yield 425 mg, 33%); $^1H$ NMR (CDCl$_3$) δ1.53 (d, J=7.5 Hz, 3H), 2.98 (m, 1H), 3.28 (m, 2H), 3.82 (s, 3H), 4.22 (m, 1H), 4.39 (dd, J$_1$=5.1 Hz, J$_2$=9.9 Hz, 1H), 6.92 (s, 1H); IR (KBr) 3325 (w), 3255 (w), 3077 (w), 2981 (m), 2940 (m), 2879 (w), 2848 (m), 1677 (s), 1674 (s), 1651 (s), 1637 (s), 1634 (s), 1609 (s), 1455 (m), 1412 (w), 1387 (w), 1372 (w), 1347 (m), 1304 (m), 1289 (m), 1226 (s), 1185 (w), 1147 (m), 1118 (m), 1089 (w), 1056 (w), 1044 (m), 1017 (m), 978 (m), 954 (m), 941 (w), 918 (m), 896 (w), 850 (m), 805 (m), 793 (m), 786 (m), 763 (m), 712 (m), 687 (m), 654 (m) cm$^{-1}$.

Example 75

Preparation of 7,8-dichloro-6-methyl-3-methoxy-6,7,8,9-tetrahydro-1H-1-benzazepine-2,5-dione (111)

To stirred, ice bath cold triflic acid (20 mL, Aldrich) there was added a solution of 6,7-dichloro-2-methoxy-5-methyl-5,6,7,8-tetrahydronapthalene-1,4-dione (410 mg, 1.49 mmol) in TFA (2 mL, Aldrich) over one min to give a red solution. To this there was added solid $NaN_3$ (387 mg, 5.96 mmol, Baker) in portions over 2 min with stirring. The ice bath was removed and the reaction was allowed to stir at rt under $N_2$. After 2.5 h, a small aliquot was removed, added to $H_2O$ and extracted with $CHCl_3$. TLC (5% EtOAc/95% $CHCl_3$) of the extract indicated >90% conversion of the starting quinone to two major lower R$_f$ products (overlapping spots) with an estimated ratio of 9 to 1. The reaction was carefully added to crushed ice to give a brown suspension. This was extracted with 30% MeOH/70% $CHCl_3$ (3×30 mL). The extract was washed with $H_2O$, saturated $NaHCO_3$ and saturated brine (1×30 mL each), filtered through cotton and the solvent removed in vacuo to give a brown solid (~300 mg). Crystallization from 95% EtOH (dissolved in boiling solvent (30 mL), hot filtered, concd to 20 mL, allowed to cool to rt then cooled in an ice bath) yielded a brown solid (135 mg, 31%, purity >95% by TLC and $^1H$ NMR, probable mixture of diastereomers (9 to 1)); mp 165° C. (dec., preheated oil bath); $^1H$ NMR (DMSO-$d_6$ and $D_2O$) δ1.19 (d, J=6.9 Hz, 3H), 2.97 (dd, J$_1$=17.7 Hz, J$_2$=9.6 Hz, 1H), 3.13 (dd, J$_1$=17.7 Hz, J$_2$=4.8 Hz, 1H), 3.21 (m, 1H), 3.70 (s, 3H), 4.15 (dd, J$_1$=9.6 Hz, J$_2$=6.9 Hz, 1H), 4.40 (m, 1H), 6.24 (s, 1H), the spectrum without $D_2O$ shows an additional resonance δ10.77 (s, 1H); IR (KBr) 3220 (m), 3146 (w), 3107 (m), 2989 (m), 1693 (s), 1623 (s), 1552 (s), 1501 (w), 1462 (m), 1454 (w), 1442 (w), 1416 (m), 1402 (m), 1381 (m), 1353 (w), 1327 (w), 1295 (m), 1286 (m), 1244 (m), 1221 (m), 1197 (m), 1177 (m), 1162 (m), 1118 (m), 1095 (w), 1071 (w), 1031 (m), 997 (m), 984 (m), 936 (w), 909 (w), 892 (m), 818 (m), 762 (m), 752 (w), 676 (m), 622 (m), 494 (m) cm$^{-1}$.

Example 76

Preparation of 7,8-dichloro-3-hydroxy-6-methyl-6,7,8,9-tetrahydro-1H-1-benzazepine-2,5-dione (112)

To a stirred suspension of 7,8-dichloro-3-methoxy-6-methyl-6,7,8,9-tetrahydro-1H-1-benzazepine-2,5-dione (120 mg, 413 μmol) in dry $CH_2Cl_2$ (20 mL, distilled from $CaH_2$) under $N_2$, there was added a solution of $BBr_3$ in $CH_2Cl_2$ (2.5 mL, 1M, Aldrich) in one portion over 5 seconds at rt. The suspension immediately turned green. The reaction was allowed to stir under $N_2$ at rt for 1 h. The reaction was added to saturated $NaHCO_3$ (50 mL) and the resulting pale pink suspension was vigorously stirred for 15 min to give an emulsion. The emulsion was vacuum filtered and the resulting pink aqueous solution washed with $CH_2Cl_2$ (1×10 mL). The aqueous portion was acidified with concd HCl (pH 2). The resulting precipitate was collected by filtration and washed to neutrality with water (6×2 mL). Crystallization of the damp filter cake from 95% EtOH (dissolved in boiling solvent (45 mL), hot filtered, allowed to cool to rt) yielded a colorless, fluffy solid (67 mg, 59%, pure by $^1H$ NMR, probable mixture of diastereomers (9 to 1)); mp 180°–181°

C. (dec.); $^1$H NMR (DMSO-d$_6$ and D$_2$O) δ1.17 (d, J=6.9 Hz, 3H), 2.97 (dd, J$_1$=17.4 Hz, J$_2$=9.6 Hz, 1H), 3.13 (dd, J$_1$=17.4 Hz, J$_2$=4.8 Hz, 1H), 3.22 (m, 1H), 4.13 (dd, J$_1$=9.3 Hz, J$_2$=6.6 Hz, 1H), 4.38 (m, 1H), 6.32 (s, 1H), the spectrum without D2O shows additional resonances δ10.47 (bs, 1H), 11.01 (s, 1H); IR (KBr) 3301 (m), 3207 (w), 3165 (w), 3093 (m), 2987 (m), 1680 (m), 1648 (m), 1613 (m), 1553 (s), 1463 (w), 1447 (w), 1425 (w), 1401 (m), 1345 (m), 1319 (w), 1285 (m), 1227 (m), 1164 (w), 1123 (w), 1054 (w), 1020 (w), 934 (w), 911 (m), 861 (w), 810 (m), 770 (m), 754 (m), 717 (m), 667 (w), 656 (w), 621 (w), 494 (w) cm$^{-1}$; Anal. Calcd for C$_{11}$H$_{11}$Cl$_2$NO$_3$: C, 47.85, H, 4.02, N, 5.07. Found: C, 48.00; H, 3.85; N, 5.20.

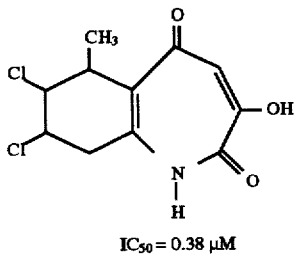

IC$_{50}$ = 0.38 μM

The binding data imply that compounds of Formula IX having a combination of substituents other than H at R$_1$, R$_3$ and R$_4$ are preferred.

Example 77

Preparation of 6,7,8,9-Tetrahydro-7,8-dichloro-6-ethyl-3-hydroxy-1H-1-benzazepine-2,5-dione 5,8-Dihydro-5-ethyl-2-methoxynaphthalene-1,4-dione. To a stirred suspension of 2-bromo-5-methoxybenzoquinone (8.7 g, 40 mmol) in toluene (200 mL) there was added 1,3-hexadiene (5.0 g, 61 mmol) in one portion. The reaction mixture was allowed to stir in a 60°–70° C. oil bath under N$_2$ for 7 days. A homogeneous solution was present. The status of the reaction was determined by $^1$H NMR. Since this type of bromo adduct may not be stable once the reaction solvent is evaporated, an aliquot was diluted in half with MeOH and treated with an excess of Et$_3$N. After 5 min, dilute HCl (10% concd HCl/90% H$_2$O) was added and the mixture extracted with CHCl$_3$. The extract was washed with H$_2$O, filtered through cotton and the solvent was removed in vacuo. The $^1$H NMR was then determined in CDCl$_3$. The absence of a resonance at 7.24 ppm indicated that the starting quinone was totally consumed. The remaining reaction mixture was allowed to cool to 25° C. and was diluted in half with MeOH. The reaction was purged with N$_2$ for 5 min with stirring then Et$_3$N (8.32 g, 82.2 mmol, EM) was added. The reaction mixture darkened. The reaction was allowed to stir for 5 min under N$_2$ at 25° C. Dilute HCl (vide supra, 500 mL) was then vigorously stirred in to give a lighter yellow/orange mixture. The layers were separated and the aqueous layer was extracted with toluene (1×50 mL). The toluene portion was washed with H$_2$O (2×200 mL), and brine (1×200 mL), filtered through cotton and the solvent removed in vacuo to give a green solid (8.7 g). Crystallization from 95% EtOH (dissolved in 60 mL boiling solvent, hot filtered, allowed to cool to rt) yielded a yellow/green solid (4.8 g, purity –85% by NMR). Re, crystallization from 95% EtOH (dissolved in boiling solvent (15 mL), allowed to cool to rt) yielded a yellow/green crystalline solid (4.12 g, 46% for the two steps, ~95% pure by TLC and $^1$H NMR); mp 99°–101° C.; $^1$H NMR (CDCl$_3$) δ0.81 (t, J=7.5 Hz, 3H), 1.64 (m, 2H), 2.91 (m, 1H), 3.18 (m, 1H), 3.45 (m, 1H), 3.81 (s, 3H), 5.83 (m, 2H), 5.88 (s, 1H); IR (KBr) 2957, 1668, 1633, 1602, 1218, 101210, 870, 719, 659, 630 cm$^{-1}$.

5,6,7,8-Tetrahydro-6,7-dichloro-5-ethyl-2-methoxynaphthalene-1,4-dione. To a stirred solution of 5,8-dihydro-5-ethyl-2-methoxynaphthalene-1,4-dione (2.00 g, 9.16 mmol) in CHCl$_3$ (100 mL, passed through silica gel prior to use), a solution of Cl$_2$ in CCl$_4$ (8.3 mL, ~1.1M) was added dropwise over a 5 min period. After addition, the reaction was allowed to stir an additional 30 min at 25° C. Analysis (NMR) indicated partial consumption of the starting material. An additional portion of the Cl$_2$ solution (4 mL) was added. The reaction was allowed to stir at 25° C. for 1 hr. The analysis now indicated the absence of starting material. The solvent was removed in vacuo to give an orange syrup. The addition of 95% EtOH (10 mL) and steam bath warming prompted solidification. The solvent was removed in vacuo to given an orange solid. Crystallization from 95% EtOH (dissolved in boiling solvent (10 mL), hot filtered, allowed to cool to rt) yielded a yellow granular solid (1.37 g, 52%, pure by TLC (5% EtOAc/95% CHCl$_3$), approximately a 2:1 mixture of diastereomers by NMR); mp 115°–118° C.; $^1$H NMR (CDCl$_3$) δ1.03 (overlapping t, 3H), 1.90 (m, 2H), 2.93 (m, 1H), 3.27 (m, 2H), 3.82 (s, 3H), 4.40 (m, 2H), 5.90 and 5.92 (overlapping s, 1H); IR (KBr) 2970, 2938, 1675, 1652, 1633, 1609, 1226, 855 cm$^{-1}$.

6,7,8,9-Tetrahydro-7,8-dichloro-6-ethyl-3-methoxy-1H-1-benzazepine-2,5-dione. To stirred, ice bath cold CF$_3$SO$_3$H (10 g, 6 mL, Lancaster), solid 5,6,7,8-tetrahydro-5,6-dichloro-2-methoxynaphthalene-1,4-dione (1.30 g, 4.50 mmol) was added in portions over 3 min to give a deep red solution. Solid NaN$_3$ (585 mg, 9.00 mmol, Aldrich) was added in portions with stirring over 3 min. The ice bath was removed and the reaction was allowed to stir under N$_2$. After 4 h, an aliquot was removed for analysis (added to water, extracted with CHCl$_3$). TLC (5% EtOAc/95% CHCl$_3$) indicated near total consumption of the organic starting material and the formation of a much lower Rf product. The extremely thick reaction mixture was added to ice water (100 mL) to yield a brown precipitate. The suspension was vigorously stirred with 30% MeOH/70% CHCl$_3$ (100 mL). The layers were separated (not all the solid dissolved) and the aqueous portion was extracted with 30% MeOH/70% CHCl$_3$ (6×40 mL, all solid now dissolved). The extract was washed with water, saturated NaHCO$_3$ and brine (100 mL each), filtered through cotton and the solvent removed in vacuo to give a brown solid. Crystallization from 95% EtOH (dissolved in boiling solvent (200 mL), boiled with activated charcoal (2 spatula tips) for 5 min, hot filtered (Whatman #2), concd to 80 mL, allowed to cool to rt, allowed to stand at 4° C. overnight) yielded a yellow powder (563 mg, 41%, a diastereomeric mixture by NMR (8:2)); mp, transforms to a denser solid above 140° C. then melts 196°–200° C.; $^1$H NMR (DMSO-d$_6$ and D$_2$O) δ0.76 (overlapping t, 3H), 1.27–1.78 (overlapping m, 2H), 2.93 (m, 1H), 3.11 (dd, J$_1$=4.5 Hz, J$_2$=17.4 Hz, 1H), 3.35 (m, 1H), 3.71 (s, 3H), 4.21 (dd, J$_1$=6.3 Hz, J$_2$=9.0 Hz, 1H), 4.36–4.62 (overlapping m, 1H), 6.24 (s, 1H), the spectrum without D$_2$O displays an additional resonance at 10.76 and 10.82 (overlapping s, 1H); IR (KBr) 3230, 3118, 3005, 1693, 1618, 1555, 1417, 1241, 1223, 1178, 890 cm$^{-1}$.

6,7,8,9-Tetrahydro-7,8-dichloro-6-ethyl-3-hydroxy-1H-1-benzazepine-2,5-dione. To a stirred suspension of 6,7,8,9-tetrahydro-7,8-dichloro-6-ethyl-3-methoxy-1H-1-benzazepine-2,5-dione (525 mg, 1.73 mmol) in dry CH$_2$Cl$_2$ (60 mL, from CaH$_2$) under N$_2$, a solution of BBr$_3$ in CH$_2$Cl$_2$ (10 mL, 1M, Aldrich) was added over 10 s. The suspension turned orange, then a yellow solution was observed which transformed to a yellow suspension. The suspension was allowed to stir under $N_2$ for 1 h. The reaction was added to saturated $NaHCO_3$ (200 mL) and was allowed to stir for 10 min. A pink emulsion was obtained. The emulsion was vacuum filtered (changed filter papers frequently, saved) to give a pink solution. The solution was washed with $CH_2Cl_2$ (2×50 mL). The pH of the aqueous portion was adjusted to 2 with concd HCl. The resulting precipitate was collected and washed with water (6×2 mL). The damp filter cake was crystallized from 95% EtOH (dissolved in boiling solvent (100 mL), hot filtered, concd to 40 mL, allowed to cool to rt) to give a pale beige solid (62 mg, 12%, a mixture of diastereomers by NMR (8:2)); mp 197° C. (dec, preheat to 195° C.); $^1$H NMR (DMSO-$d_6$ and $D_2O$) δ0.75 (overlapping t, 3H), 1.22–1.77 (overlapping m, 2H), 2.94 (m, 1H), 3.11 (dd, $J_1$=4.8 Hz, $J_2$=17.1 Hz, 1H), 3.37 (overlapping m, 1H), 4.20 (dd, $J_1$=5.7 Hz, $J_2$=9.3 Hz, 1H), 4.34–4.61 (overlapping m, 1H), 6.32 and 6.33 (overlapping s, 1H), the spectrum without $D_2O$ displayed additional resonances at 10.45 (bs, 1H), 10.99 and 11.05 (overlapping s, 1H); IR (KBr) 3305, 3207, 3097, 2990, 1679, 1647, 1612, 1553, 1399, 1284, 1229, 912 cm$^{-1}$.

An additional portion was obtained as described below. The above mentioned filter papers were suspended in water (100 mL). The pH was adjusted to 2 with concd HCl. The suspension was allowed to stir for 5 min. The mass was collected by vacuum filtration. The collected mass was washed with water (6×20 mL). The damp mass was stirred in boiling 95% EtOH (250 mL) for 5 min. The hot suspension was vacuum filtered and the collected mass washed with 95% EtOH (20 mL). The cloudy filtrate was heated to boiling which resulted in a clear solution. This was hot filtered, concd to 75 mL and allowed to cool to rt. The resulting solid was collected, washed with 95% EtOH and dried in vacuo to give a colorless solid (174 mg, 35%, a mixture of diastereomers by NMR (8:2)); mp 198° C. (dec, preheat to 195° C.). The $^1$H NMR and IR spectra are identical to those described above.

Example 78

Binding Assays and In Vivo Studies

As described above, $IC_{50}$ values were determined for compounds active in inhibiting 1 µM glycine-stimulated [$^3$H]-MK-801 binding by computer-assisted plotting of inhibition curves and interpolation. The results are shown in Table 1.

TABLE 1

| Drug | $IC_{50}$ (µM) |
|---|---|
| 43 | inactive |
| 44 | inactive |
| 45 | inactive |
| 46 | 7.3 |
| 61 | 34 |
| 70 | 8.4 |
| 74 | 3.6 |
| 81 | 9.28 |
| 87 | 6.7 |
| 93 | 196 |
| 97 | 26 |
| 99 | 69.5 |
| 109 | inactive |
| 112 | 0.38 |

A number of 6,7,8,9-tetrahydrobenzazepines were tested for binding affinity to the glycine site and for anticonvulsant activity in the maximum-induced seizure (MES) assay in mice. The results are shown in Table 2.

TABLE 2

Structure and Activity of 3-Hydroxy-6,7,8,9-tetrahydro-1-benzazepine-2,5-diones

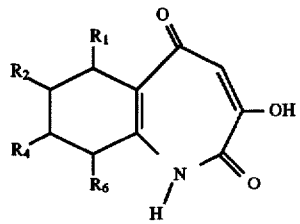

| $R_1$ | $R_6$ | $R_3$ | $R_4$ | $K_i$ (nM)[a] | $ED_{50}$ (MES) (mg/kg) |
|---|---|---|---|---|---|
| Me | H | Cl | Cl | 7 | ND[b] |
| H | H | Cl | Cl | 30 | 30[c] |
| H | H | Me | Me | 177 | 6 |
| H | H | H | H | 1650 | 8 |
| | $CH_2CH_2$ | H | H | 332 | 8 |
| | $CH_2$ | H | H | 760[d] | ND |

[a]From electrophysiology using Xenopus oocytes unless otherwise noted.
[b]Not determined.
[c]Possibly due to elimination of HCl.
[d]From binding assays.

The results show that 7,8-dichloro-6-methyl-3-hydroxy-6,7,8,9-tetrahydro-1H-benzazepine-2,5-dione has a $K_i$=7 nM from electrophysiology, which is approaching that of 6,7-dichloro-5-nitro-1,4-dihydroquinoxaline-2,3-dione ($K_i$= 3.3 nM), one of the most active NMDA/glycine site antagonists that have been discovered. All of the compounds tested showed good activity in preventing seizures in mice.

Having now fully described this invention, it will be understood to those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:
1. A compound of the Formula

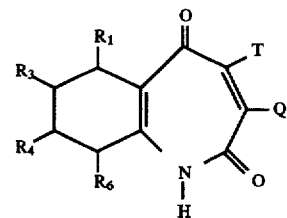

or a tautomer thereof or a pharmaceutically acceptable salt thereof; wherein $R_1$, $R_3$, $R_4$ and $R_6$ are independently hydrogen, halo, $C_1$–$C_4$ haloalkyl, $C_6$–$C_{14}$ aryl, $C_1$–$C_4$ alkyl, $C_2$–$C_4$ alkenyl, $C_2$–$C_4$ alkynyl, $C_6$–$C_{14}$ aryl($C_1$–$C_4$)alkyl, ($C_6$–$C_{14}$)aryl($C_1$–$C_4$)alkenyl, $C_6$–$C_{14}$ aryl($C_1$–$C_4$) alkynyl, $C_1$–$C_4$ hydroxyalkyl, nitro, amino, cyano, $C_1$–$C_6$ alkanoylamino, hydroxy, thiol, $C_1$–$C_6$ alkanoyloxy, azido, $C_1$–$C_4$ alkoxy, carboxy, carbonylamido, $C_1$–$C_4$ alkylthiol, $C_3$–$C_{18}$ trialkylsilyloxy, or $C_8$–$C_{18}$ phenyldialkylsilyloxy;

Q is $OR_7$ or $NR_{12}R_{13}$, wherein $R_{12}$ and $R_{13}$ are independently selected from hydrogen, $C_1$–$C_6$ alkyl, $C_3$–$C_7$ cycloalkyl($C_1$–$C_6$)alkyl, $C_6$–$C_{14}$ aryl, $C_6$–$C_{14}$ aryl ($C_1$–$C_6$)alkyl, and $CH_2Y$ wherein Y is selected from $(CHOH)_nCH_2OH$ and $(CH_2)_mR^c$ where m is 0 to 5, n is 1 to 5 and $R^c$ is selected from hydroxy, $C_1$–$C_6$ alkoxycarbonyl, and $NR^dR^e$ in which $R^d$ and $R^e$ are independently selected from hydrogen and $C_1$–$C_6$ alkyl or $R^d$ and $R^e$, together with the nitrogen atom to which they are attached, form a 5-, 6- or 7-membered heterocyclic ring which, in addition to said nitrogen atom, optionally contains one additional heteroatom selected from nitrogen, oxygen and sulfur; or $R_{12}$ and $R_{13}$, together with the nitrogen atom to which they are attached, form a 5-, 6- or 7-membered heterocyclic ring which is bonded to said compound through said nitrogen atom, said heterocyclic ring optionally containing, in addition to said nitrogen atom, one additional heteroatom selected from nitrogen, oxygen and sulfur; $R_7$ is hydrogen, $C_1$–$C_4$ alkyl or $C_1$–$C_6$ alkanoyl; and T is selected from hydrogen, halo, hydroxy, $C_1$–$C_6$ alkanoyloxy, $C_1$–$C_4$ alkyl which may optionally bear a substituent selected from amino, $C_1$–$C_4$ alkanoylamino, carboxy and carboxamido; and $C_6$–$C_{14}$ aryl($C_1$–$C_4$)alkyl.

2. A compound of the Formula

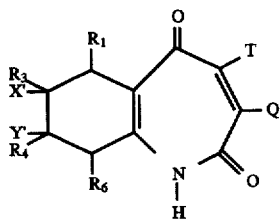

or a tautomer thereof or a pharmaceutically acceptable salt thereof; wherein $R_1$, $R_3$, $R_4$ and $R_6$ are independently hydrogen, halo, $C_1$–$C_4$ haloalkyl, $C_6$–$C_{14}$ aryl, $C_1$–$C_4$ alkyl, $C_2$–$C_4$ alkenyl, $C_2$–$C_4$ alkynyl, $C_6$–$C_{14}$ aryl($C_1$–$C_4$)alkyl, $C_6$–$C_{14}$ aryl($C_1$–$C_4$)alkenyl, $C_6$–$C_{14}$ aryl($C_1$–$C_4$)alkynyl, $C_1$–$C_4$ hydroxyalkyl, nitro, amino, cyano, $C_1$–$C_6$ alkanoylamino, hydroxy, thiol, $C_1$–$C_6$ alkanoyloxy, azido, $C_1$–$C_4$ alkoxy, carboxy, carbonylamido, $C_1$–$C_4$ alkylthiol, $C_3$–$C_{18}$ trialkylsilyloxy, or $C_8$–$C_{18}$ phenyldialkylsilyloxy;

X' and Y' are independently hydrogen, halogen; hydroxy and hydrogen; nitro and hydrogen; $C_1$–$C_6$ alkanoylamido and hydrogen; X' and Y' together form an oxirane ring; X' and Y' are vicinal $C_1$–$C_6$ alkanoylamido $C_1$–$C_6$ alkanoyloxy groups; or X' and Y' together form a double bond;

Q is $OR_7$ or $NR_{12}R_{13}$, wherein $R_{12}$ and $R_{13}$ are independently selected from hydrogen, $C_1$–$C_6$ alkyl, $C_3$–$C_7$ cycloalkyl($C_3$–$C_6$)alkyl, $C_6$–$C_{14}$ aryl, $C_6$–$C_{14}$ aryl ($C_1$–$C_6$)alkyl, and $CH_2Y$ wherein Y is selected from $(CHOH)_nCH_2OH$ and $(CH_2)_mR^c$ where m is 0 to 5, n is 1 to 5 and $R^c$ is selected from hydroxy, $C_1$–$C_6$ alkoxycarbonyl, and $NR^dR^e$ in which $R^d$ and $R^e$ are independently selected from hydrogen and $C_1$–$C_6$ alkyl or $R^d$ and $R^e$, together with the nitrogen atom to which they are attached, form a 5-, 6- or 7-membered heterocyclic ring which, in addition to said nitrogen atom, optionally contains one additional heteroatom selected from nitrogen, oxygen and sulfur; or $R_{12}$ and $R_{13}$, together with the nitrogen atom to which they are attached, form a 5-, 6- or 7-membered heterocyclic ring which is bonded to said compound through said nitrogen atom, said heterocyclic ring optionally containing, in addition to said nitrogen atom, one additional heteroatom selected from nitrogen, oxygen and sulfur; $R_7$ is hydrogen, $C_1$–$C_4$ alkyl or $C_1$–$C_6$ alkanoyl; and T is selected from hydrogen, halo, hydroxy, $C_1$–$C_6$ alkanoyloxy, $C_1$–$C_4$ alkyl which may optionally bear a substituent selected from amino, $C_1$–$C_4$ alkanoylamino, carboxy and carboxamido; and $C_6$–$C_{14}$aryl($C_1$–$C_4$)alkyl.

3. A compound of the Formula

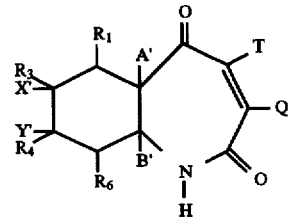

or a tautomer thereof or a pharmaceutically acceptable salt thereof; wherein $R_1$, $R_3$, $R_4$ and $R_6$ are independently hydrogen, halo, $C_1$–$C_4$ haloalkyl, $C_6$–$C_4$ aryl, $C_1$–$C_4$ alkyl, $C_2$–$C_4$ alkenyl, $C_2$–$C_4$ alkynyl, $C_6$–$C_{14}$ aryl($C_1$–$C_4$)alkyl, $C_6$–$C_{14}$ aryl($C_1$–$C_4$)alkenyl, $C_6$–$C_4$ aryl($C_1$–$C_4$) alkynyl, $C_1$–$C_4$ hydroxyalkyl, nitro, amino, cyano, $C_1$–$C_6$ alkanoylamino, hydroxy, thiol, $C_1$–$C_6$ alkanoyloxy, azido, $C_1$–$C_4$ alkoxy, carboxy, carbonylamido, $C_1$–$C_4$ alkylthiol, $C_3$–$C_{18}$ trialkylsilyloxy, or $C_8$–$C_{18}$ phenyldialkylsilyloxy;

X' and Y' are independently hydrogen, halogen; hydroxy and hydrogen; nitro and hydrogen; $C_1$–$C_6$ alkanoylamido and hydrogen; X' and Y' together form an oxirane ring; X' and Y' are vicinal $C_1$–$C_6$ alkanoylamido $C_1$–$C_6$ alkanoyloxy groups; or X' and Y' together form a double bond;

one of A' and B' is hydrogen and the other of A' and B' is $C_1$–$C_4$ alkyl or $C_6$–$C_{14}$ ar($C_1$–$C_4$)alkyl;

Q is $OR_7$ or $NR_{12}R_{13}$, wherein $R_{12}$ and $R_{13}$ are independently selected from hydrogen, $C_1$–$C_6$ alkyl, $C_3$–$C_7$ cycloalkyl($C_1$–$C_6$)alkyl, $C_6$–$C_{14}$ aryl, $C_6$–$C_{14}$ aryl ($C_1$–$C_6$)alkyl, and $CH_2Y$ wherein Y is selected from $(CHOH)_nCH_2OH$ and $(CH_2)_mR^c$ where m is 0 to 5, n is 1 to 5 and $R^c$ is selected from hydroxy, $C_1$–$C_6$ alkoxycarbonyl, and $NR^dR^e$ in which $R^d$ and $R^e$ are independently selected from hydrogen and $C_1$–$C_6$ alkyl or $R^d$ and $R^e$, together with the nitrogen atom to which they are attached, form a 5-, 6- or 7-membered heterocyclic ring which, in addition to said nitrogen atom, optionally contains one additional heteroatom selected from nitrogen, oxygen and sulfur; or $R_{12}$ and $R_{13}$, together with the nitrogen atom to which they are attached, form a 5-, 6- or 7-membered heterocyclic ring which is bonded to said compound through said nitrogen atom, said heterocyclic ring optionally containing, in addition to said nitrogen atom, one additional heteroatom selected from nitrogen, oxygen and sulfur; $R_7$ is hydrogen, $C_1$–$C_4$ alkyl or $C_1$–$C_6$ alkanoyl; and T is selected from hydrogen, halo, hydroxy, $C_1$–$C_6$ alkanoyloxy, $C_1$–$C_4$ alkyl which may optionally bear a substituent selected from amino, $C_1$–$C_4$ alkanoylamino, carboxy and carboxamido; and $C_6$–$C_{14}$ aryl($C_1$–$C_4$)alkyl.

4. A compound of the Formula

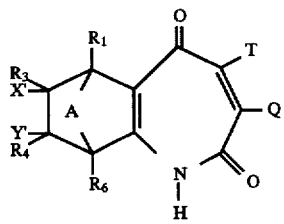

or a tautomer thereof or a pharmaceutically acceptable salt thereof; wherein $R_1$, $R_3$, $R_4$ and $R_6$ are independently hydrogen, halo, $C_1$–$C_4$ haloalkyl, $C_6$–$C_4$ aryl, $C_1$–$C_4$ alkyl, $C_2$–$C_4$ alkenyl, $C_2$–$C_4$ alkynyl, $C_6$–$C_{14}$ aryl($C_1$–$C_4$)alkyl, $C_6$–$C_{14}$ aryl($C_1$–$C_4$)alkenyl, $C_6$–$C_4$ aryl($C_1$–$C_4$) alkynyl, $C_1$–$C_4$ hydroxyalkyl, nitro, amino, cyano, $C_1$–$C_6$ alkanoylamino, hydroxy, thiol, $C_1$–$C_6$ alkanoyloxy, azido, $C_1$–$C_4$ alkoxy, carboxy, carbonylamido, $C_1$–$C_4$ alkylthiol, $C_3$–$C_{18}$ trialkylsilyloxy, or $C_8$–$C_{18}$ phenyldialkylsilyloxy;

A is $(CH_2)_n$, wherein n is 1 to 4;

X' and Y' are independently hydrogen, halogen; hydroxy and hydrogen; nitro and hydrogen; $C_1$–$C_6$ alkanoylamido and hydrogen; X' and Y' together form an oxirane ring; X' and Y' are vicinal $C_1$–$C_6$ alkanoylamido $C_1$–$C_6$ alkanoyloxy groups; or X' and Y' together form a double bond;

Q is $OR_7$ or $NR_{12}R_{13}$, wherein $R_{12}$ and $R_{13}$ are independently selected from hydrogen, $C_1$–$C_6$ alkyl, $C_3$–$C_7$ cycloalkyl($C_1$–$C_6$)alkyl, $C_6$–$C_{14}$ aryl, $C_6$–$C_{14}$ aryl ($C_1$–$C_6$)alkyl, and $CH_2Y$ wherein Y is selected from $(CHOH)_nCH_2OH$ and $(CH_2)_mR^c$ where m is 0 to 5, n is 1 to 5 and $R^c$ is selected from hydroxy, $C_1$–$C_6$ alkoxycarbonyl, and $NR^dR^e$ in which $R^d$ and $R^e$ are independently selected from hydrogen and $C_1$–$C_6$ alkyl or $R^d$ and $R^e$, together with the nitrogen atom to which they are attached, form a 5-, 6- or 7-membered heterocyclic ring which, in addition to said nitrogen atom, optionally contains one additional heteroatom selected from nitrogen, oxygen and sulfur; or $R_{12}$ and $R_{13}$, together with the nitrogen atom to which they are attached, form a 5-, 6- or 7-membered heterocyclic ring which is bonded to said compound through said nitrogen atom, said heterocyclic ring optionally containing, in addition to said nitrogen atom, one additional heteroatom selected from nitrogen, oxygen and sulfur; $R_7$ is hydrogen, $C_1$–$C_4$ alkyl or $C_1$–$C_6$ alkanoyl; and T is selected from hydrogen, halo, hydroxy, $C_1$–$C_6$ alkanoyloxy, $C_1$–$C_4$ alkyl which may optionally bear a substituent selected from amino, $C_1$–$C_4$ alkanoylamino, carboxy and carboxamido; and $C_6$–$C_{14}$ aryl($C_1$–$C_4$)alkyl.

5. A compound of any of claims 1–4, wherein T is hydrogen.

6. A compound of any of claims 1–4, wherein Q is $OR_7$ and $R_7$ is hydrogen, $C_1$–$C_4$ alkyl or $C_1$–$C_6$ alkanoyl.

7. A compound of claim 6, where $R_7$ is hydrogen.

8. A compound of any of claims 1–4, wherein Q is $NR_{12}R_{13}$, wherein $NR_{12}R_{13}$ represents a heterocyclic ring selected from the group consisting of morpholino; imidazolyl; pyrrolidinyl; pyrrolo; pyrazolyl; piperidinyl optionally substituted at the 4-position by one of $C_1$–$C_6$ alkyl, phenyl($C_1$–$C_6$)alkyl, phenoxy or phenyl; piperazinyl optionally substituted at the 4-position by one of $C_1$–$C_6$ alkyl, phenyl($C_1$–$C_6$)alkyl or phenyl; and perhydroazepinyl.

9. A compound of any of claims 1–4, wherein wherein Q is $NR_{12}R_{13}$, and $NR_{12}R_{13}$ represents amino, methylamino, dimethylamino, diethylamino, phenethylamino, 4-morpholino, allylamino, α-methylbenzylamino, t-butoxycarbonylmethylamino, 1-perhydroazepinyl, 1-pyrrolidinyl, anilino, pyrrolo, 4-phenylpiperazin-1-yl, 4-benzylpiperazin-1-yl, piperidino, 4-(N,N-diethylamino) ethylamino, glucamino, 4-phenoxypiperidine, benzylamino, cyclopropylmethylamino, 3,4-dibenzyloxyphenethylamino, 2-(4-imidazolyl)ethylamino, N,N-bis(2-hydroxyethyl) amino and N-(2-hydroxyethyl)amino.

10. A compound of any of claims 1–4, wherein $R_6$ is hydrogen.

11. A compound of claim 1, wherein $R_1$, $R_3$ and $R_4$ are other than hydrogen, and $R_6$ is hydrogen.

12. A compound of claim 1, which is one of:

3-methoxy-6,7,8,9-tetrahydro-1H-1-benzazepine-2,5-dione;

3-hydroxy-6,7,8,9-tetrahydro-1H-1-benzazepine-2,5-dione;

3-methoxy-7,8-dichloro-6,7,8,9-tetrahydro-1H-1-benzazepine-2,5-dione;

3-hydroxy-7,8-dichloro-6,7,8,9-tetrahydro-1H-1-benzazepine-2,5-dione;

7,8-dimethyl-3-methoxy-6,7, 8,9-tetrahydro-1H-1-benzazepine-2,5-dione;

7,8-dimethyl-3-hydroxy-6,7,8,9-tetrahydro-1H-1-benzazepine-2,5 , dione;

7,8-dichloro-6-methyl-3-methoxy-6,7,8,9-tetrahydro-1H-1-benzazepine-2,5-dione;

7,8-dichloro-3-hydroxy-6-methyl-6,7,8,9-tetrahydro-1H-1-benzazepine-2,5-dione; and 6,7,8,9-tetrahydro-7,8-dichloro-6-ethyl-3-hydroxy-1H-1-benzazepine-2,5-dione.

13. A compound of claim 4, which is one of:

3-hydroxy-6,9-methano-6,7,8,9-tetrahydro-1H-1-benzazepine-2,5-dione;

6,9-methano-3-methoxy-6,7,8,9-tetrahydro-1H-1-benzazepine-2,5-dione;

6,9-ethano-3-methoxy-6,7,8,9-tetrahydro-1H-1-benzazepine-2,5-diione; and 6,9-ethano-3-hydroxy-6,7,8,9-tetrahydro-1H-1-benzazepine-2,5-dione.

* * * * *